US006436703B1

(12) United States Patent
Tang et al.

(10) Patent No.: US 6,436,703 B1
(45) Date of Patent: Aug. 20, 2002

(54) NUCLEIC ACIDS AND POLYPEPTIDES

(75) Inventors: Y. Tom Tang; Chenghua Liu; Ping Zhou, all of San Jose; Vinod Asundi, Foster City; Jie Zhang, Campbell; Jian-Rui Wang, Cupertino; Aidong J. Xue, Sunnyvale; Chongjun Xu, San Jose; Radoje T. Drmanac, Palo Alto, all of CA (US)

(73) Assignee: Hyseq, Inc., Sunnyvale, CA (US)

( * ) Notice: Subject to any disclaimer, the term of this patent is extended or adjusted under 35 U.S.C. 154(b) by 0 days.

(21) Appl. No.: 09/668,680

(22) Filed: Sep. 22, 2000

Related U.S. Application Data

(63) Continuation-in-part of application No. 09/649,167, filed on Aug. 23, 2000, which is a continuation-in-part of application No. 09/540,217, filed on Mar. 31, 2000.

(51) Int. Cl.[7] .............................. C12N 15/12; C12N 5/00
(52) U.S. Cl. ...................... 435/325; 536/23.1; 536/23.5; 435/320.1
(58) Field of Search .............................. 536/23.1, 23.5; 435/325, 320.1

(56) References Cited

PUBLICATIONS

GenBank Accession No.: AK000316 (Feb. 22, 2000).
GenBank Accession No.: BAA91079 (Feb. 22, 2000).
GenBank Accession No.: AL135937 (Mar. 15, 2001).
GenBank Accession No.: AA004350 (May 7, 1997).
GenBank Accession No.: AB006141 (Aug. 7, 1997).
AF044601, GENBANK, Jul. 22, 1999.*
AF044600, GENBANK, Jul. 22, 1999.*
Tan et al. "Bloning and Characterization of a Human and Murine T–Cell Orphan G–Protein–Coupled Receptor Similar to the Growth Hormone Secretagogue and Neurotensin Receptors", GENOMICS 1998 vol. 52 pp. 223–229.*
Fujii et al. "Identification of Neuromedin U as the Cognate Ligand of the Orphan G Protein–coupled Receptor FM–3", The Journal of Biological Chemistry Jul. 14, 2000 vol. 275 No. 28 pp. 21068–21074.*

\* cited by examiner

Primary Examiner—Marianne P. Allen

(57) ABSTRACT

The present invention provides novel nucleic acids, novel polypeptide sequences encoded by these nucleic acids and uses thereof.

5 Claims, No Drawings

NUCLEIC ACIDS AND POLYPEPTIDES

1. CROSS REFERENCE TO RELATED APPLICATIONS

This application is a continuation-in-part application of U.S. application Ser. No. 09/649,167, filed Aug. 23, 2000, which in turn is a continuation-in-part application of U.S. application Ser. No. 09/540,217, filed Mar. 31, 2000, both of which are incorporated herein by reference in their entirety.

2. BACKGROUND OF THE INVENTION

2.1 Technical Field

The present invention provides novel polynucleotides and proteins encoded by such polynucleotides, along with uses for these polynucleotides and proteins, for example in therapeutic, diagnostic and research methods.

2.2 Background

Technology aimed at the discovery of protein factors (including e.g., cytokines, such as lymphokines, interferons, CSFs, chemokines, and interleukins) has matured rapidly over the past decade. The now routine hybridization cloning and expression cloning techniques clone novel polynucleotides "directly" in the sense that they rely on information directly related to the discovered protein (i.e., partial DNA/amino acid sequence of the protein in the case of hybridization cloning; activity of the protein in the case of expression cloning). More recent "indirect" cloning techniques such as signal sequence cloning, which isolates DNA sequences based on the presence of a now well-recognized secretory leader sequence motif, as well as various PCR-based or low stringency hybridization-based cloning techniques, have advanced the state of the art by making available large numbers of DNA/amino acid sequences for proteins that are known to have biological activity, for example, by virtue of their secreted nature in the case of leader sequence cloning, by virtue of their cell or tissue source in the case of PCR-based techniques, or by virtue of structural similarity to other genes of known biological activity.

Identified polynucleotide and polypeptide sequences have numerous applications in, for example, diagnostics, forensics, gene mapping; identification of mutations responsible for genetic disorders or other traits, to assess biodiversity, and to produce many other types of data and products dependent on DNA and amino acid sequences.

3. SUMMARY OF THE INVENTION

The compositions of the present invention include novel isolated polypeptides, novel isolated polynucleotides encoding such polypeptides, including recombinant DNA molecules, cloned genes or degenerate variants thereof, especially naturally occurring variants such as allelic variants, antisense polynucleotide molecules, and antibodies that specifically recognize one or more epitopes present on such polypeptides, as well as hybridomas producing such antibodies.

The compositions of the present invention additionally include vectors, including expression vectors, containing the polynucleotides of the invention, cells genetically engineered to contain such polynucleotides and cells genetically engineered to express such polynucleotides.

The present invention relates to a collection or library of at least one novel nucleic acid sequence assembled from expressed sequence tags (ESTs) isolated mainly by sequencing by hybridization (SBH), and in some cases, sequences obtained from one or more public databases. The invention relates also to the proteins encoded by such polynucleotides, along with therapeutic, diagnostic and research utilities for these polynucleotides and proteins. These nucleic acid sequences are designated as SEQ ID NO: 1–13 and are provided in the Sequence Listing. In the nucleic acids provided in the Sequence Listing, A is adenosine; C is cytosine; G is guanosine; T is thymine; and N is any of the four bases. In the amino acids provided in the Sequence Listing, * corresponds to the stop codon.

The nucleic acid sequences of the present invention also include, nucleic acid sequences that hybridize to the complement of SEQ ID NO: 1–13 under stringent hybridization conditions; nucleic acid sequences which are allelic variants or species homologues of any of the nucleic acid sequences recited above, or nucleic acid sequences that encode a peptide comprising a specific domain or truncation of the peptides encoded by SEQ ID NO: 1–13. A polynucleotide comprising a nucleotide sequence having at least 90% identity to an identifying sequence of SEQ ID NO: 1–13 or a degenerate variant or fragment thereof. The identifying sequence can be 100 base pairs in length.

The nucleic acid sequences of the present invention also include the sequence information from the nucleic acid sequences of SEQ ID NO: 1–13. The sequence information can be a segment of any one of SEQ ID NO: 1–13 that uniquely identifies or represents the sequence information of SEQ ID NO: 1–13.

A collection as used in this application can be a collection of only one polynucleotide. The collection of sequence information or identifying information of each sequence can be provided on a nucleic acid array. In one embodiment, segments of sequence information is provided on a nucleic acid array to detect the polynucleotide that contains the segment. The array can be designed to detect full-match or mismatch to the polynucleotide that contains the segment. The collection can also be provided in a computer-readable format.

This invention also includes the reverse or direct complement of any of the nucleic acid sequences recited above; cloning or expression vectors containing the nucleic acid sequences; and host cells or organisms transformed with these expression vectors. Nucleic acid sequences (or their reverse or direct complements) according to the invention have numerous applications in a variety of techniques known to those skilled in the art of molecular biology, such as use as hybridization probes, use as primers for PCR, use in an array, use in computer-readable media, use in sequencing full-length genes, use for chromosome and gene mapping, use in the recombinant production of protein, and use in the generation of anti-sense DNA or RNA, their chemical analogs and the like.

In a preferred embodiment, the nucleic acid sequences of SEQ ID NO: 1–13 or novel segments or parts of the nucleic acids of the invention are used as primers in expression assays that are well known in the art. In a particularly preferred embodiment, the nucleic acid sequences of SEQ ID NO: 1–13 or novel segments or parts of the nucleic acids provided herein are used in diagnostics for identifying expressed genes or, as well known in the art and exemplified by Vollrath et al., Science 258:52–59 (1992), as expressed sequence tags for physical mapping of the human genome.

The isolated polynucleotides of the invention include, but are not limited to, a polynucleotide comprising any one of the nucleotide sequences set forth in SEQ ID NO: 1–13; a polynucleotide comprising any of the full length protein coding sequences of SEQ ID NO: 1–13; and a polynucleotide comprising any of the nucleotide sequences of the mature protein coding sequences of SEQ ID NO: 1–13. The polynucleotides of the present invention also include, but are not limited to, a polynucleotide that hybridizes under stringent hybridization conditions to (a) the complement of any one of the nucleotide sequences set forth in SEQ ID NO: 1–13; (b) a nucleotide sequence encoding anyone of the amino acid sequences set forth in the Sequence Listing; (c) a polynucleotide which is an allelic variant of any polynucleotides recited above; (d) a polynucleotide which encodes a species homolog (e.g. orthologs) of any of the proteins recited above; or (e) a polynucleotide that encodes a polypeptide comprising a specific domain or truncation of any of the polypeptides comprising an amino acid sequence set forth in the Sequence Listing.

The isolated polypeptides of the invention include, but are not limited to, a polypeptide comprising any of the amino acid sequences set forth in the Sequence Listing; or the corresponding full length or mature protein. Polypeptides of the invention also include polypeptides with biological activity that are encoded by (a) any of the polynucleotides having a nucleotide sequence set forth in SEQ ID NO: 1–13; or (b) polynucleotides that hybridize to the complement of the polynucleotides of (a) under stringent hybridization conditions. Biologically or immunologically active variants of any of the polypeptide sequences in the Sequence Listing, and "substantial equivalents" thereof (e.g., with at least about 65%, 70%, 75%, 80%, 85%, 90%, 95%, 98% or 99% amino acid sequence identity) that preferably retain biological activity are also contemplated. The polypeptides of the invention may be wholly or partially chemically synthesized but are preferably produced by recombinant means using the genetically engineered cells (e.g. host cells) of the invention.

The invention also provides .compositions comprising a polypeptide of the invention. Polypeptide compositions of the invention may further comprise an acceptable carrier, such as a hydrophilic, e.g., pharmaceutically acceptable, carrier.

The invention also provides host cells transformed or transfected with a polynucleotide of the invention.

The invention also relates to methods for producing a polypeptide of the invention comprising growing a culture of the host cells of the invention in a suitable culture medium under conditions permitting expression of the desired polypeptide, and purifying the polypeptide from the culture or from the host cells. Preferred embodiments include those in which the protein produced by such process is a mature form of the protein.

Polynucleotides according to the invention have numerous applications in a variety of techniques known to those skilled in the art of molecular biology. These techniques include use as hybridization probes, use as oligomers, or primers, for PCR, use for chromosome and gene mapping, use in the recombinant production of protein, and use in generation of anti-sense DNA or RNA, their chemical analogs and the like. For example, when the expression of an mRNA is largely restricted to a particular cell or tissue type, polynucleotides of the invention can be used as hybridization probes to detect the presence of the particular cell or tissue mRNA in a sample using, e.g., in situ hybridization.

In other exemplary embodiments, the polynucleotides are used in diagnostics as expressed sequence tags for identifying expressed genes or, as well known in the art and exemplified by Vollrath et al., Science 258:52–59 (1992), as expressed sequence tags for physical mapping of the human genome.

The polypeptides according to the invention can be used in a variety of conventional procedures and methods that are currently applied to other proteins. For example, a polypeptide of the invention can be used to generate an antibody that specifically binds the polypeptide. Such antibodies, particularly monoclonal antibodies, are useful for detecting or quantitating the polypeptide in tissue. The polypeptides of the invention can also be used as molecular weight markers, and as a food supplement.

Methods are also provided for preventing, treating, or ameliorating a medical condition which comprises the step of administering to a mammalian subject a therapeutically effective amount of a composition comprising a polypeptide of the present invention and a pharmaceutically acceptable carrier.

In particular, the polypeptides and polynucleotides of the invention can be utilized, for example, in methods for the prevention and/or treatment of disorders involving aberrant protein expression or biological activity.

The present invention further relates to methods for detecting the presence of the polynucleotides or polypeptides of the invention in a sample. Such methods can, for example, be utilized as part of prognostic and diagnostic evaluation of disorders as recited herein and for the identification of subjects exhibiting a predisposition to such conditions. The invention provides a method for detecting the polynucleotides of the invention in a sample, comprising contacting the sample with a compound that binds to and forms a complex with the polynucleotide of interest for a period sufficient to form the complex and under conditions sufficient to form a complex and detecting the complex such that if a complex is detected, the polynucleotide of interest is detected. The invention also provides a method for detecting the polypeptides of the invention in a sample comprising contacting the sample with a compound that binds to and forms a complex with the polypeptide under conditions and for a period sufficient to form the complex and detecting the formation of the complex such that if a complex is formed, the polypeptide is detected.

The invention also provides kits comprising polynucleotide probes and/or monoclonal antibodies, and optionally quantitative standards, for carrying out methods of the invention. Furthermore, the invention provides methods for evaluating the efficacy of drugs, and monitoring the progress of patients, involved in clinical trials for the treatment of disorders as recited above.

The invention also provides methods for the identification of compounds that modulate (i.e., increase or decrease) the expression or activity of the polynucleotides and/or polypeptides of the invention. Such methods can be utilized, for example, for the identification of compounds that can ameliorate symptoms of disorders as recited herein. Such methods can include, but are not limited to, assays for identifying compounds and other substances that interact with (e.g., bind to) the polypeptides of the invention. The invention provides a method for identifying a compound that binds to the polypeptides of the invention comprising contacting the compound with a polypeptide of the invention in a cell for a time sufficient to form a polypeptide/compound complex, wherein the complex drives expression of a reporter gene sequence in the cell; and detecting the complex by detecting the reporter gene sequence expression such that if expression of the reporter gene is detected the compound the binds to a polypeptide of the invention is identified.

The methods of the invention also provides methods for treatment which involve the administration of the polynucleotides or polypeptides of the invention to individuals exhibiting symptoms or tendencies. In addition, the invention encompasses methods for treating diseases or disorders as recited herein comprising administering compounds and other substances that modulate the overall activity of the target gene products. Compounds and other substances can effect such modulation either on the level of target gene/protein expression or target protein activity.

The polypeptides of the present invention and the polynucleotides encoding them are also useful for the same functions known to one of skill in the art as the polypeptides and polynucleotides to which they have homology (set forth in Table I); for which they have a signature region (as set forth in Table 3); or for which they have homology to a gene family (as set forth in Table 4). If no homology is set forth for a sequence, then the polypeptides and polynucleotides of the present invention are useful for a variety of applications, as described herein, including use in arrays for detection.

4. DETAILED DESCRIPTION OF THE INVENTION 4.1 Definitions

It must be noted that as used herein and in the appended claims, the singular forms "a", "an" and "the" include plural references unless the context clearly dictates otherwise.

The term "active" refers to those forms of the polypeptide which retain the biologic and/or immunologic activities of any naturally occurring polypeptide. According to the invention, the terms "biologically active" or "biological activity" refer to a protein or peptide having structural, regulatory or biochemical functions of a naturally occurring molecule. Likewise "immunologically active" or "immunological activity" refers to the capability of the natural, recombinant or synthetic polypeptide to induce a specific immune response in appropriate animals or cells and to bind with specific antibodies.

The term "activated cells" as used in this application are those cells which are engaged in extracellular or intracellular membrane trafficking, including the export of secretory or enzymatic molecules as part of a normal or disease process.

The terms "complementary" or "complementarity" refer to the natural binding of polynucleotides by base pairing. For example, the sequence 5'-AGT-3' binds to the complementary sequence 3'-TCA-5'. Complementarity between two single-stranded molecules may be "partial" such that only some of the nucleic acids bind or it may be "complete" such that total complementarity exists between the single stranded molecules. The degree of complementarity between the nucleic acid strands has significant effects on the efficiency and strength of the hybridization between the nucleic acid strands.

The term "embryonic stem cells (ES)" refers to a cell that can give rise to many differentiated cell types in an embryo or an adult, including the germ cells. The term "germ line stem cells (GSCs)" refers to stem cells derived from primordial stem cells that provide a steady and continuous source of germ cells for the production of gametes. The term "primordial germ cells (PGCs)" refers to a small population of cells set aside from other cell lineages particularly from the yolk sac, mesenteries, or gonadal ridges during embryogenesis that have the potential to differentiate into germ cells and other cells. PGCs are the source from which GSCs and ES cells are derived The PGCs, the GSCs and the ES cells are capable of self-renewal. Thus these cells not only populate the germ line and give rise to a plurality of terminally differentiated cells that comprise the adult specialized organs, but are able to regenerate themselves.

The term "expression modulating fragment," EMF, means a series of nucleotides which modulates the expression of an operably linked ORF or another EMF.

As used herein, a sequence is said to "modulate the expression of an operably linked sequence" when the expression of the sequence is altered by the presence of the EMF. EMFs include, but are not limited to, promoters, and promoter modulating sequences (inducible elements). One class of EMFs are nucleic acid fragments which induce the expression of an operably linked ORF in response to a specific regulatory factor or physiological event.

The terms "nucleotide sequence" or "nucleic acid" or "polynucleotide" or "oligonculeotide" are used interchangeably and refer to a heteropolymer of nucleotides or the sequence of these nucleotides. These phrases also refer to DNA or RNA of genomic or synthetic origin which may be single-stranded or double-stranded and may represent the sense or the antisense strand, to peptide nucleic acid (PNA) or to any DNA-like or RNA-like material. It is contemplated that where the polynucleotide is RNA, the T (thymine) in the sequences provided herein is substituted with U (uracil). Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene.

The terms "oligonucleotide fragment" or a "polynucleotide fragment", "portion," or "segment" or "probe" or "primer" are used interchangeable and refer to a sequence of nucleotide residues which are at least about 5 nucleotides, more preferably at least about 7 nucleotides, more preferably at least about 9 nucleotides, more preferably at least about 11 nucleotides and most preferably at least about 17 nucleotides. The fragment is preferably less than about 500 nucleotides, preferably less than about 200 nucleotides, more preferably less than about 100 nucleotides, more preferably less than about 50 nucleotides and most preferably less than 30 nucleotides. Preferably the probe is from about 6 nucleotides to about 200 nucleotides, preferably from about 15 to about 50 nucleotides, more preferably from about 17 to 30 nucleotides and most preferably from about 20 to 25 nucleotides. Preferably the fragments can be used in polymerase chain reaction (PCR), various hybridization procedures or microarray procedures to identify or amplify identical or related parts of mRNA or DNA molecules. A fragment or segment may uniquely identify each polynucleotide sequence of the present invention. Preferably the fragment comprises a sequence substantially similar to any one of SEQ ID NOs: 1–13.

Probes may, for example, be used to determine whether specific mRNA molecules are present in a cell or tissue or to isolate similar nucleic acid sequences from chromosomal DNA as described by Walsh et al. (Walsh, P. S. et al., 1992, PCR Methods Appl 1:241–250). They may be labeled by nick translation, Klenow fill-in reaction, PCR, or other methods well known in the art. Probes of the present invention, their preparation and/or labeling are elaborated in Sambrook, J. et al., 1989, Molecular Cloning: A Laboratory Manual, Cold Spring Harbor Laboratory, NY; or Ausubel, F. M. et al., 1989, Current Protocols in Molecular Biology, John Wiley & Sons, New York N.Y., both of which are incorporated herein by reference in their entirety.

The nucleic acid sequences of the present invention also include the sequence information from the nucleic acid sequences of SEQ ID NOs: 1–13. The sequence information can be a segment of any one of SEQ ID NOs: 1–13 that uniquely identifies or represents the sequence information of that sequence of SEQ ID NO: 1–13. One such segment can be a twenty-mer nucleic acid sequence because the probability that a twenty-mer is fully matched in the human genome is 1 in 300. In the human genome, there are three billion base pairs in one set of chromosomes. Because $4^{20}$ possible twenty-mers exist, there are 300 times more twenty-mers than there are base pairs in a set of human chromosome. Using the same analysis, the probability for a seventeen-mer to be fully matched in the human genome is approximately 1 in 5. When these segments are used in arrays for expression studies, fifteen-mer segments can be used. The probability that the fifteen-mer is fully matched in the expressed sequences is also approximately one in five because expressed sequences comprise less than approximately 5% of the entire genome sequence.

Similarly, when using sequence information for detecting a single mismatch, a segment can be a twenty-five mer. The probability that the twenty-five mer would appear in a human genome with a single mismatch is calculated by multiplying the probability for a full match $(1 \div 4^{25})$ times the increased probability for mismatch at each nucleotide position ($3 \times 25$). The probability that an eighteen mer with a single mismatch can be detected in an array for expression studies is approximately one in five. The probability that a twenty-mer with a single mismatch can be detected in a human genome is approximately one in five.

The term "open reading frame," ORF, means a series of nucleotide triplets coding for amino acids without any termination codons and is a sequence translatable into protein.

The terms "operably linked" or "operably associated" refer to functionally related nucleic acid sequences. For example, a promoter is operably associated or operably linked with a coding sequence if the promoter controls the transcription of the coding sequence. While operably linked nucleic acid sequences can be contiguous and in the same reading frame, certain genetic elements e.g. repressor genes are not contiguously linked to the coding sequence but still control transcription/translation of the coding sequence.

The term "pluripotent" refers to the capability of a cell to differentiate into a number of differentiated cell types that are present in an adult organism. A pluripotent cell is restricted in its differentiation capability in comparison to a totipotent cell.

The terms "polypeptide" or "peptide" or "amino acid sequence" refer to an oligopeptide, peptide, polypeptide or protein sequence or fragment thereof and to naturally occurring or synthetic molecules. A polypeptide "fragment," "portion," or "segment" is a stretch of amino acid residues of at least about 5 amino acids, preferably at least about 7 amino acids, more preferably at least about 9 amino acids and most preferably at least about 17 or more amino acids. The peptide preferably is not greater than about 200 amino acids, more preferably less than 150 amino acids and most preferably less than 100 amino acids. Preferably the peptide is from about 5 to about 200 amino acids. To be active, any polypeptide must have sufficient length to display biological and/or immunological activity.

The term "naturally occurring polypeptide" refers to polypeptides produced by cells that have not been genetically engineered and specifically contemplates various polypeptides arising from post-translational modifications of the polypeptide including, but not limited to, acetylation, carboxylation, glycosylation, phosphorylation, lipidation and acylation.

The term "translated protein coding portion" means a sequence which encodes for the full length protein which may include any leader sequence or any processing sequence.

The term "mature protein coding sequence" means a sequence which encodes a peptide or protein without a signal or leader sequence. The peptide may have been produced by processing in the cell which removes any leader/signal sequence. The peptide may be produced synthetically or the protein may have been produced using a polynucleotide only encoding for the mature protein coding sequence.

The term "derivative" refers to polypeptides chemically modified by such techniques as ubiquitination, labeling (e.g., with radionuclides or various enzymes), covalent polymer attachment such as pegylation (derivatization with polyethylene glycol) and insertion or substitution by chemical synthesis of amino acids such as ornithine, which do not normally occur in human proteins.

The term "variant" (or "analog") refers to any polypeptide differing from naturally occurring polypeptides by amino acid insertions, deletions, and substitutions, created using, e g., recombinant DNA techniques. Guidance in determining which amino acid residues may be replaced, added or deleted without abolishing activities of interest, may be found by comparing the sequence of the particular polypeptide with that of homologous peptides and minimizing the number of amino acid sequence changes made in regions of high homology (conserved regions) or by replacing amino acids with consensus sequence.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

Preferably, amino acid "substitutions" are the result of replacing one amino acid with another amino acid having similar structural and/or chemical properties, i.e., conservative amino acid replacements. "Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Insertions" or "deletions" are preferably in the range of about 1 to 20 amino acids, more preferably 1 to 10 amino acids. The variation allowed may be experimentally determined by systematically making insertions, deletions, or substitutions of amino acids in a polypeptide molecule using recombinant DNA techniques and assaying the resulting recombinant variants for activity.

Alternatively, where alteration of function is desired, insertions, deletions or non-conservative alterations can be engineered to produce altered polypeptides. Such alterations can, for example, alter one or more of the biological functions or biochemical characteristics of the polypeptides of the invention. For example, such alterations may change polypeptide characteristics such as ligand-binding affinities, interchain affinities, or degradation/turnover rate. Further, such alterations can be selected so as to generate polypeptides that are better suited for expression, scale up and the like in the host cells chosen for expression. For example, cysteine residues can be deleted or substituted with another amino acid residue in order to eliminate disulfide bridges.

The terms "purified" or "substantially purified" as used herein denotes that the indicated nucleic acid or polypeptide is present in the substantial absence of other biological macromolecules, e.g., polynucleotides, proteins, and the like. In one embodiment, the polynucleotide or polypeptide is purified such that it constitutes at least 95% by weight, more preferably at least 99% by weight, of the indicated biological macromolecules present (but water, buffers, and other small molecules, especially molecules having a molecular weight of less than 1000 daltons, can be present).

The term "isolated" as used herein refers to a nucleic acid or polypeptide separated from at least one other component (e.g., nucleic acid or polypeptide) present with the nucleic acid or polypeptide in its natural source. In one embodiment, the nucleic acid or polypeptide is found in the presence of (if anything) only a solvent, buffer, ion, or other component normally present in a solution of the same. The terms "isolated" and "purified" do not encompass nucleic acids or polypeptides present in their natural source.

The term "recombinant," when used herein to refer to a polypeptide or protein, means that a polypeptide or protein is derived from recombinant (e.g., microbial, insect, or mammalian) expression systems. "Microbial" refers to recombinant polypeptides or proteins made in bacterial or fungal (e.g., yeast) expression systems. As a product, "recombinant microbial" defines a polypeptide or protein essentially free of native endogenous substances and unaccompanied by associated native glycosylation. Polypeptides or proteins expressed in most bacterial cultures, e.g., *E. Coli*, will be free of glycosylation modifications; polypeptides or proteins expressed in yeast will have a glycosylation pattern in general different from those expressed in mammalian cells.

The term "recombinant expression vehicle or vector" refers to a plasmid or phage or virus or vector, for expressing a polypeptide from a DNA (RNA) sequence. An expression vehicle can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an amino terminal methionine residue. This residue may or may not be subsequently cleaved from the expressed recombinant protein to provide a final product.

The term "recombinant expression system" means host cells which have stably integrated a recombinant transcriptional unit into chromosomal DNA or carry the recombinant transcriptional unit extrachromosomally. Recombinant expression systems as defined herein will express heterologous polypeptides or proteins upon induction of the regulatory elements linked to the DNA segment or synthetic gene to be expressed. This term also means host cells which have stably integrated a recombinant genetic element or elements having a regulatory role in gene expression, for example, promoters or enhancers. Recombinant expression systems as defined herein will express polypeptides or proteins endogenous to the cell upon induction of the regulatory elements linked to the endogenous DNA segment or gene to be expressed. The cells can be prokaryotic or eukaryotic.

The term "secreted" includes a protein that is transported across or through a membrane, including transport as a result of signal sequences in its amino acid sequence when it is expressed in a suitable host cell. "Secreted" proteins include without limitation proteins secreted wholly (e.g., soluble proteins) or partially (e.g., receptors) from the cell in which they are expressed. "Secreted" proteins also include without limitation proteins that are transported across the membrane of the endoplasmic reticulum. "Secreted" proteins are also intended to include proteins containing non-typical signal sequences (e.g. Interleukin-1 Beta, see Krasney, P. A. and Young, P. R. (1992) Cytokine 4(2):134–143) and factors released from damaged cells (e.g. Interleukin-1 Receptor Antagonist, see Arend, W. P. et. al. (1998) Annu. Rev. Immunol. 16:27–55)

Where desired, an expression vector may be designed to contain a "signal or leader sequence" which will direct the polypeptide through the membrane of a cell. Such a sequence may be naturally present on the polypeptides of the present invention or provided from heterologous protein sources by recombinant DNA techniques.

The term "stringent" is used to refer to conditions that are commonly understood in the art as stringent. Stringent conditions can include highly stringent conditions (i.e., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C.), and moderately stringent conditions (i.e., washing in 0.2×SSC/0.1% SDS at 42° C.). Other exemplary hybridization conditions are described herein in the examples.

In instances of hybridization of deoxyoligonucleotides, additional exemplary stringent hybridization conditions include washing in 6×SSC/0.05% sodium pyrophosphate at 37° C. (for 14-base oligonucleotides), 48° C. (for 17-base oligos), 55° C. (for 20-base oligonucleotides), and 60° C. (for 23-base oligonucleotides).

As used herein, "substantially equivalent" can refer both to nucleotide and amino acid sequences, for example a mutant sequence, that varies from a reference sequence by one or more substitutions, deletions, or additions, the net effect of which does not result in an adverse functional dissimilarity between the reference and subject sequences. Typically, such a substantially equivalent sequence varies from one of those listed herein by no more than about 35% (i.e., the number of individual residue substitutions, additions, and/or deletions in a substantially equivalent sequence, as compared to the corresponding reference sequence, divided by the total number of residues in the substantially equivalent sequence is about 0.35 or less). Such a sequence is said to have 65% sequence identity to the listed sequence. In one embodiment, a substantially equivalent, e.g., mutant, sequence of the invention varies from a listed sequence by no more than 30% (70% sequence identity); in a variation of this embodiment, by no more than 25% (75% sequence identity); and in a further variation of this embodiment, by no more than 20% (80% sequence identity) and in a further variation of this embodiment, by no more than 10% (90% sequence identity) and in a further variation of this embodiment, by no more that 5% (95% sequence identity). Substantially equivalent, e.g., mutant, amino acid sequences according to the invention preferably have at least 80% sequence identity with a listed amino acid sequence, more preferably at least 90% sequence identity. Substantially equivalent nucleotide sequences of the invention can have lower percent sequence identities, taking into account, for example, the redundancy or degeneracy of the genetic code. Preferably, nucleotide sequence has at least about 65% identity, more preferably at least about 75% identity, and most preferably at least about 95% identity. For the purposes of the present invention, sequences having substantially equivalent biological activity and substantially equivalent expression characteristics are considered substantially equivalent. For the purposes of determining equivalence, truncation of the mature sequence (e.g., via a mutation which creates a spurious stop codon) should be disregarded. Sequence identity may be determined, e.g., using the Jotun Hein method (Hein, J. (1990) Methods Enzymol. 183:626–645). Identity between sequences can also be determined by other methods known in the art, e.g. by varying hybridization conditions.

The term "totipotent" refers to the capability of a cell to differentiate into all of the cell types of an adult organism.

The term "transformation" means introducing DNA into a suitable host cell so that the DNA is replicable, either as an extrachromosomal element, or by chromosomal integration. The term "transfection" refers to the taking up of an expression vector by a suitable host cell, whether or not any coding sequences are in fact expressed. The term "infection" refers to the introduction of nucleic acids into a suitable host cell by use of a virus or viral vector.

As used herein, an "uptake modulating fragment," UMF, means a series of nucleotides which mediate the uptake of a linked DNA fragment into a cell. UMFs can be readily identified using known UMFs as a target sequence or target motif with the computer-based systems described below. The presence and activity of a UMF can be confirmed by attaching the suspected UMF to a marker sequence. The resulting nucleic acid molecule is then incubated with an appropriate host under appropriate conditions and the uptake of the marker sequence is determined. As described above, a UMF will increase the frequency of uptake of a linked marker sequence.

Each of the above terms is meant to encompass all that is described for each, unless the context dictates otherwise.

4.2 Nucleic Acids of the Invention

Nucleotide sequences of the invention are set forth in the Sequence Listing.

The isolated polynucleotides of the invention include a polynucleotide comprising the nucleotide sequences of SEQ ID NO: 1–13; a polynucleotide encoding any one of the peptide sequences of SEQ ID NO: 1–13; and a polynucleotide comprising the nucleotide sequence encoding the mature protein coding sequence of the polynucleotides of any one of SEQ ID NO: 1–13. The polynucleotides of the present invention also include, but are not limited to, a polynucleotide that hybridizes under stringent conditions to (a) the complement of any of the nucleotides sequences of SEQ ID NO: 1–13; (b) nucleotide sequences encoding any one of the amino acid sequences set forth in the Sequence Listing; (c) a polynucleotide which is an allelic variant of any polynucleotide recited above; (d) a polynucleotide which encodes a species homolog of any of the proteins recited above; or (e) a polynucleotide that encodes a polypeptide comprising a specific domain or truncation of the polypeptides of SEQ ID NO: 1–13. Domains of interest may depend on the nature of the encoded polypeptide; e.g., domains in receptor-like polypeptides include ligand-binding, extracellular, transmembrane, or cytoplasmic domains, or combinations thereof; domains in immunoglobulin-like proteins include the variable immunoglobulin-like domains; domains in enzyme-like polypeptides include catalytic and substrate binding domains; and domains in ligand polypeptides include receptor-binding domains.

The polynucleotides of the invention include naturally occurring or wholly or partially synthetic DNA, e.g., cDNA and genomic DNA, and RNA, e.g., mRNA. The polynucleotides may include all of the coding region of the cDNA or may represent a portion of the coding region of the cDNA.

The present invention also provides genes corresponding to the cDNA sequences disclosed herein. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials. Further 5' and 3' sequence can be obtained using methods known in the art. For example, full length cDNA or genomic DNA that corresponds to any of the polynucleotides of SEQ ID NO: 1–13 can be obtained by screening appropriate cDNA or genomic DNA libraries under suitable hybridization conditions using any of the polynucleotides of SEQ ID NO: 1–13 or a portion thereof as a probe. Alternatively, the polynucleotides of SEQ ID NO: 1–13 may be used as the basis for suitable primer(s) that allow identification and/or amplification of genes in appropriate genomic DNA or cDNA libraries.

The nucleic acid sequences of the invention can be assembled from ESTs and sequences (including cDNA and genomic sequences) obtained from one or more public databases, such as dbEST, gbpri, and UniGene. The EST sequences can provide identifying sequence information, representative fragment or segment information, or novel segment information for the full-length gene.

The polynucleotides of the invention also provide polynucleotides including nucleotide sequences that are substantially equivalent to the polynucleotides recited above. Polynucleotides according to the invention can have, e.g., at least about 65%, at least about 70%, at least about 75%, at least about 80%, more typically at least about 90%, and even more typically at least about 95%, sequence identity to a polynucleotide recited above.

Included within the scope of the nucleic acid sequences of the invention are nucleic acid sequence fragments that hybridize under stringent conditions to any of the nucleotide sequences of SEQ ID NO: 1–13, or complements thereof, which fragment is greater than about 5 nucleotides, preferably 7 nucleotides, more preferably greater than 9 nucleotides and most preferably greater than 17 nucleotides. Fragments of, e.g. 15, 17, or 20 nucleotides or more that are selective for (i.e. specifically hybridize to any one of the polynucleotides of the invention) are contemplated. Probes capable of specifically hybridizing to a polynucleotide can differentiate polynucleotide sequences of the invention from other polynucleotide sequences in the same family of genes or can differentiate human genes from genes of other species, and are preferably based on unique nucleotide sequences.

The sequences falling within the scope of the present invention are not limited to these specific sequences, but also include allelic and species variations thereof. Allelic and species variations can be routinely determined by comparing the sequence provided in SEQ ID NO: 1–13, a representative fragment thereof, or a nucleotide sequence at least 90% identical, preferably 95% identical, to SEQ ID NOs: 1–13 with a sequence from another isolate of the same species. Furthermore, to accommodate codon variability, the invention includes nucleic acid molecules coding for the same amino acid sequences as do the specific ORFs disclosed herein. In other words, in the coding region of an ORF, substitution of one codon for another codon that encodes the same amino acid is expressly contemplated.

The nearest neighbor or homology result for the nucleic acids of the present invention, including SEQ ID NOs: 1–13, can be obtained by searching a database using an algorithm or a program. Preferably, a BLAST which stands for Basic Local Alignment Search Tool is used to search for local sequence alignments (Altshul, S. F. J Mol. Evol. 36 290–300 (1993) and Altschul S. F. et al. J. Mol. Biol. 21:403–410 (1990)). Alternatively a FASTA version 3 search against Genpept, using Fastxy algorithm.

Species homologs (or orthologs) of the disclosed polynucleotides and proteins are also provided by the present invention. Species homologs may be isolated and identified by making suitable probes or primers from the sequences provided herein and screening a suitable nucleic acid source from the desired species.

The invention also encompasses allelic variants of the disclosed polynucleotides or proteins; that is, naturally-occurring alternative forms of the isolated polynucleotide which also encode proteins which are identical, homologous or related to that encoded by the polynucleotides.

The nucleic acid sequences of the invention are further directed to sequences which encode variants of the described nucleic acids. These amino acid sequence variants may be prepared by methods known in the art by introducing appropriate nucleotide changes into a native or variant polynucleotide. There are two variables in the construction of amino acid sequence variants: the location of the mutation and the nature of the mutation. Nucleic acids encoding the amino acid sequence variants are preferably constructed by mutating the polynucleotide to encode an amino acid sequence that does not occur in nature. These nucleic acid alterations can be made at sites that differ in the nucleic acids from different species (variable positions) or in highly conserved regions (constant regions). Sites at such locations will typically be modified in series, e.g., by substituting first with conservative choices (e.g., hydrophobic amino acid to a different hydrophobic amino acid) and then with more distant choices (e.g., hydrophobic amino acid to a charged amino acid), and then deletions or insertions may be made at the target site. Amino acid sequence deletions generally range from about 1 to 30 residues, preferably about 1 to 10 residues, and are typically contiguous. Amino acid insertions include amino- and/or carboxyl-terminal fusions ranging in length from one to one hundred or more residues, as well as intrasequence insertions of single or multiple amino acid residues. Intrasequence insertions may range generally from about 1 to 10 amino residues, preferably from 1 to 5 residues. Examples of terminal insertions include the heterologous signal sequences necessary for secretion or for intracellular targeting in different host cells and sequences such as FLAG or poly-histidine sequences useful for purifying the expressed protein.

In a preferred method, polynucleotides encoding the novel amino acid sequences are changed via site-directed mutagenesis. This method uses oligonucleotide sequences to alter a polynucleotide to encode the desired amino acid variant, as well as sufficient adjacent nucleotides on both sides of the changed amino acid to form a stable duplex on either side of the site of being changed. In general, the techniques of site-directed mutagenesis are well known to those of skill in the art and this technique is exemplified by publications such as, Edelman et al., DNA 2:183 (1983). A versatile and efficient method for producing site-specific changes in a polynucleotide sequence was published by Zoller and Smith, Nucleic Acids Res. 10:6487–6500 (1982). PCR may also be used to create amino acid sequence variants of the novel nucleic acids. When small amounts of template DNA are used as starting material, primer(s) that differs slightly in sequence from the corresponding region in the template DNA can generate the desired amino acid variant. PCR amplification results in a population of product DNA fragments that differ from the polynucleotide template encoding the polypeptide at the position specified by the primer. The product DNA fragments replace the corresponding region in the plasmid and this gives a polynucleotide encoding the desired amino acid variant.

A further technique for generating amino acid variants is the cassette mutagenesis technique described in Wells et al., Gene 34:315 (1985); and other mutagenesis techniques well known in the art, such as, for example, the techniques in Sambrook et al., supra, and Current Protocols in Molecular Biology, Ausubel et al. Due to the inherent degeneracy of the genetic code, other DNA sequences which encode substantially the same or a functionally equivalent amino acid sequence may be used in the practice of the invention for the cloning and expression of these novel nucleic acids. Such DNA sequences include those which are capable of hybridizing to the appropriate novel nucleic acid sequence under stringent conditions.

Polynucleotides encoding preferred polypeptide truncations of the invention can be used to generate polynucleotides encoding chimeric or fusion proteins comprising one or more domains of the invention and heterologous protein sequences.

The polynucleotides of the invention additionally include the complement of any of the polynucleotides recited above. The polynucleotide can be DNA (genomic, cDNA, amplified, or synthetic) or RNA. Methods and algorithms for obtaining such polynucleotides are well known to those of skill in the art and can include, for example, methods for determining hybridization conditions that can routinely isolate polynucleotides of the desired sequence identities.

In accordance with the invention, polynucleotide sequences comprising the mature protein coding sequences corresponding to any one of SEQ ID NO: 1–13, or functional equivalents thereof, may be used to generate recombinant DNA molecules that direct the expression of that nucleic acid, or a functional equivalent thereof, in appropriate host cells. Also included are the cDNA inserts of any of the clones identified herein.

A polynucleotide according to the invention can be joined to any of a variety of other nucleotide sequences by well-established recombinant DNA techniques (see Sambrook J et al. (1989) Molecular Cloning: A Laboratory Manual, Cold Spring Harbor Laboratory, NY). Useful nucleotide sequences for joining to polynucleotides include an assortment of vectors, e.g., plasmids, cosmids, lambda phage derivatives, phagemids, and the like, that are well known in the art. Accordingly, the invention also provides a vector including a polynucleotide of the invention and a host cell containing the polynucleotide. In general, the vector contains an origin of replication functional in at least one organism, convenient restriction endonuclease sites, and a selectable marker for the host cell. Vectors according to the invention include expression vectors, replication vectors, probe generation vectors, and sequencing vectors. A host cell according to the invention can be a prokaryotic or eukaryotic cell and can be a unicellular organism or part of a multicellular organism.

The present invention further provides recombinant constructs comprising a nucleic acid having any of the nucleotide sequences of SEQ ID NOs: 1–13 or a fragment thereof or any other polynucleotides of the invention. In one embodiment, the recombinant constructs of the present invention comprise a vector, such as a plasmid or viral vector, into which a nucleic acid having any of the nucleotide sequences of SEQ ID NOs: 1–13 or a fragment thereof is inserted, in a forward or reverse orientation. In the case of a vector comprising one of the ORFs of the present invention, the vector may further comprise regulatory sequences, including for example, a promoter, operably linked to the ORF. Large numbers of suitable vectors and promoters are known to those of skill in the art and are commercially available for generating the recombinant constructs of the present invention. The following vectors are provided by way of example. Bacterial: pBs, phagescript, PsiXI174, pBluescript SK, pBs KS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, PXTI, pSG (Stratagene) pSVK3, pBPV, pMSG, pSVL (Pharmacia).

The isolated polynucleotide of the invention may be operably linked to an expression control sequence such as the pMT2 or pED expression vectors disclosed in Kaufman et al., *Nucleic Acids Res.* 19, 4485–4490 (1991), in order to produce the protein recombinantly. Many suitable expression control sequences are known in the art. General methods of expressing recombinant proteins are also known and are exemplified in R. Kaufman, *Methods in Enzymology* 185, 537–566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda PR, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an amino terminal identification peptide imparting desired characteristics, e.g., stabilization or simplified purification of expressed recombinant product. Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM 1 (Promega Biotech, Madison, Wis., USA). These pBR322 "backbone" sections are combined with an appropriate promoter and the structural sequence to be expressed. Following transformation of a suitable host strain and growth of the host strain to an appropriate cell density, the selected promoter is induced or derepressed by appropriate means (e.g., temperature shift or chemical induction) and cells are cultured for an additional period. Cells are typically harvested by centrifugation, disrupted by physical or chemical means, and the resulting crude extract retained for further purification.

Polynucleotides of the invention can also be used to induce immune responses. For example, as described in Fan et al., *Nat. Biotech.* 17:870–872 (1999), incorporated herein by reference, nucleic acid sequences encoding a polypeptide may be used to generate antibodies against the encoded polypeptide following topical administration of naked plasmid DNA or following injection, and preferably intramuscular injection of the DNA. The nucleic acid sequences are preferably inserted in a recombinant expression vector and may be in the form of naked DNA.

4.3 Hosts

The present invention further provides host cells genetically engineered to contain the polynucleotides of the invention. For example, such host cells may contain nucleic acids of the invention introduced into the host cell using known transformation, transfection or infection methods. The present invention still further provides host cells genetically engineered to express the polynucleotides of the invention, wherein such polynucleotides are in operative association with a regulatory sequence heterologous to the host cell which drives expression of the polynucleotides in the cell.

Knowledge of nucleic acid sequences allows for modification of cells to permit, or increase, expression of endogenous polypeptide. Cells can be modified (e.g., by homologous recombination) to provide increased polypeptide expression by replacing, in whole or in part, the naturally occurring promoter with all or part of a heterologous promoter so that the cells express the polypeptide at higher levels. The heterologous promoter is inserted in such a manner that it is operatively linked to the encoding sequences. See, for example, PCT International Publication No. WO94/12650, PCT International Publication No. WO92/20808, and PCT International Publication No. WO91/09955. It is also contemplated that, in addition to heterologous promoter DNA, amplifiable marker DNA (e.g., ada, dhfr, and the multifunctional CAD gene which encodes carbamyl phosphate synthase, aspartate transcarbamylase, and dihydroorotase) and/or intron DNA may be inserted along with the heterologous promoter DNA. If linked to the coding sequence, amplification of the marker DNA by standard selection methods results in co-amplification of the desired protein coding sequences in the cells.

The host cell can be a higher eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected by calcium phosphate transfection, DEAE, dextran mediated transfection, or electroporation (Davis, L. et al., *Basic Methods in Molecular Biology* (1986)). The host cells containing one of the polynucleotides of the invention, can be used in conventional manners to produce the gene product encoded by the isolated fragment (in the case of an ORF) or can be used to produce a heterologous protein under the control of the EMF.

Any host/vector system can be used to express one or more of the ORFs of the present invention. These include, but are not limited to, eukaryotic hosts such as HeLa cells, Cv-1 cell, COS cells, 293 cells, and Sf9 cells, as well as prokaryotic host such as *E. coli* and *B. subtilis*. The most preferred cells are those which do not normally express the particular polypeptide or protein or which expresses the polypeptide or protein at low natural level. Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., in Molecular Cloning: A Laboratory Manual, Second Edition, Cold Spring Harbor, N.Y. (1989), the disclosure of which is hereby incorporated by reference.

Various mammalian cell culture systems can also be employed to express recombinant protein. Examples of mammalian expression systems include the COS-7 lines of monkey kidney fibroblasts, described by Gluzman, Cell 23:175 (1981). Other cell lines capable of expressing a compatible vector are, for example, the C127, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells. Mammalian expression vectors will comprise an origin of replication, a suitable promoter and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements. Recombinant polypeptides and proteins produced in bacterial culture are usually isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents.

Alternatively, it may be possible to produce the protein in lower eukaryotes such as yeast or insects or in prokaryotes such as bacteria. Potentially suitable yeast strains include *Saccharomyces cerevisiae, Schizosaccharomyces pombe*, Kluyveromyces strains, Candida, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

In another embodiment of the present invention, cells and tissues may be engineered to express an endogenous gene comprising the polynucleotides of the invention under the control of inducible regulatory elements, in which case the regulatory sequences of the endogenous gene may be replaced by homologous recombination. As described herein, gene targeting can be used to replace a gene's existing regulatory region with a regulatory sequence isolated from a different gene or a novel regulatory sequence synthesized by genetic engineering methods. Such regulatory sequences may be comprised of promoters, enhancers, scaffold-attachment regions, negative regulatory elements, transcriptional initiation sites, regulatory protein binding sites or combinations of said sequences. Alternatively, sequences which affect the structure or stability of the RNA or protein produced may be replaced, removed, added, or otherwise modified by targeting. These sequence include polyadenylation signals, mRNA stability elements, splice sites, leader sequences for enhancing or modifying transport or secretion properties of the protein, or other sequences which alter or improve the function or stability of protein or RNA molecules.

The targeting event may be a simple insertion of the regulatory sequence, placing the gene under the control of the new regulatory sequence, e.g., inserting a new promoter or enhancer or both upstream of a gene. Alternatively, the targeting event may be a simple deletion of a regulatory element, such as the deletion of a tissue-specific negative regulatory element. Alternatively, the targeting event may replace an existing element; for example, a tissue-specific enhancer can be replaced by an enhancer that has broader or different cell-type specificity than the naturally occurring elements. Here, the naturally occurring sequences are deleted and new sequences are added. In all cases, the identification of the targeting event may be facilitated by the use of one or more selectable marker genes that are contiguous with the targeting DNA, allowing for the selection of cells in which the exogenous DNA has integrated into the host cell genome. The identification of the targeting event may also be facilitated by the use of one or more marker genes exhibiting the property of negative selection, such that the negatively selectable marker is linked to the exogenous DNA, but configured such that the negatively selectable marker flanks the targeting sequence, and such that a correct homologous recombination event with sequences in the host cell genome does not result in the stable integration of the negatively selectable marker. Markers useful for this purpose include the Herpes Simplex Virus thymidine kinase (TK) gene or the bacterial xanthine-guanine phosphoribosyl-transferase (gpt) gene.

The gene targeting or gene activation techniques which can be used in accordance with this aspect of the invention are more particularly described in U.S. Pat. No. 5,272,071 to Chappel; U.S. Pat. No. 5,578,461 to Sherwin et al.; International Application No. PCT/US92/09627 (WO93/09222) by Selden et al.; and International Application No. PCT/US90/06436 (WO91/06667) by Skoultchi et al., each of which is incorporated by reference herein in its entirety.

4.4 Poltpeptides of the Invention

The isolated polypeptides of the invention include, but are not limited to, a polypeptide comprising: the amino acid sequences set forth as any one of SEQ ID NO: 1–13 or an amino acid sequence encoded by any one of the nucleotide sequences SEQ ID NOs: 1–13 or the corresponding full length or mature protein. Polypeptides of the invention also include polypeptides preferably with biological or immunological activity that are encoded by: (a) a polynucleotide having any one of the nucleotide sequences set forth in SEQ ID NOs: 1–13 or (b) polynucleotides encoding any one of the amino acid sequences set forth as SEQ ID NO: 1–13 or (c) polynucleotides that hybridize to the complement of the polynucleotides of either (a) or (b) under stringent hybridization conditions. The invention also provides biologically active or immunologically active variants of any of the amino acid sequences set forth as SEQ ID NO: 1–13 or the corresponding full length or mature protein; and "substantial equivalents" thereof (e.g., with at least about 65%, at least about 70%, at least about 75%, at least about 80%, at least about 85%, at least about 90%, typically at least about 95%, more typically at least about 98%, or most typically at least about 99% amino acid identity) that retain biological activity. Polypeptides encoded by allelic variants may have a similar, increased, or decreased activity compared to polypeptides comprising SEQ ID NO: 1–13.

Fragments of the proteins of the present invention which are capable of exhibiting biological activity are also encompassed by the present invention. Fragments of the protein may be in linear form or they may be cyclized using known methods, for example, as described in H. U. Saragovi, et al., Bio/Technology 10, 773–778 (1992) and in R. S. McDowell, et al., J. Amer. Chem. Soc. 114, 9245–9253 (1992), both of which are incorporated herein by reference. Such fragments may be fused to carrier molecules such as immunoglobulins for many purposes, including increasing the valency of protein binding sites.

The present invention also provides both full-length and mature forms (for example, without a signal sequence or precursor sequence) of the disclosed proteins. The protein coding sequence is identified in the sequence listing by translation of the disclosed nucleotide sequences. The mature form of such protein may be obtained by expression of a full-length polynucleotide in a suitable mammalian cell or other host cell. The sequence of the mature form of the protein is also determinable from the amino acid sequence of the full-length form. Where proteins of the present invention are membrane bound, soluble forms of the proteins are also provided. In such forms, part or all of the regions causing the proteins to be membrane bound are deleted so that the proteins are fully secreted from the cell in which it is expressed.

Protein compositions of the present invention may further comprise an acceptable carrier, such as a hydrophilic, e.g., pharmaceutically acceptable, carrier.

The present invention further provides isolated polypeptides encoded by the nucleic acid fragments of the present invention or by degenerate variants of the nucleic acid fragments of the present invention. By "degenerate variant" is intended nucleotide fragments which differ from a nucleic acid fragment of the present invention (e.g., an ORF) by nucleotide sequence but, due to the degeneracy of the genetic code, encode an identical polypeptide sequence. Preferred nucleic acid fragments of the present invention are the ORFs that encode proteins.

A variety of methodologies known in the art can be utilized to obtain any one of the isolated polypeptides or proteins of the present invention. At the simplest level, the amino acid sequence can be synthesized using commercially available peptide synthesizers. The synthetically-constructed protein sequences, by virtue of sharing primary, secondary or tertiary structural and/or conformational characteristics with proteins may possess biological properties in common therewith, including protein activity. This technique is particularly useful in producing small peptides and fragments of larger polypeptides. Fragments are useful, for example, in generating antibodies against the native polypeptide. Thus, they may be employed as biologically active or immunological substitutes for natural, purified proteins in screening of therapeutic compounds and in immunological processes for the development of antibodies.

The polypeptides and proteins of the present invention can alternatively be purified from cells which have been altered to express the desired polypeptide or protein. As used herein, a cell is said to be altered to express a desired polypeptide or protein when the cell, through genetic manipulation, is made to produce a polypeptide or protein which it normally does not produce or which the cell normally produces at a lower level. One skilled in the art can readily adapt procedures for introducing and expressing either recombinant or synthetic sequences into eukaryotic or prokaryotic cells in order to generate a cell which produces one of the polypeptides or proteins of the present invention.

The invention also relates to methods for producing a polypeptide comprising growing a culture of host cells of the invention in a suitable culture medium, and purifying the protein from the cells or the culture in which the cells are grown. For example, the methods of the invention include a process for producing a polypeptide in which a host cell containing a suitable expression vector that includes a polynucleotide of the invention is cultured under conditions that allow expression of the encoded polypeptide. The polypeptide can be recovered from the culture, conveniently from the culture medium, or from a lysate prepared from the host cells and further purified. Preferred embodiments include those in which the protein produced by such process is a full length or mature form of the protein.

In an alternative method, the polypeptide or protein is purified from bacterial cells which naturally produce the polypeptide or protein. One skilled in the art can readily follow known methods for isolating polypeptides and proteins in order to obtain one of the isolated polypeptides or proteins of the present invention. These include, but are not limited to, immunochromatography, HPLC, size-exclusion chromatography, ion-exchange chromatography, and immuno-affinity chromatography. See, e.g., Scopes, *Protein Purification: Principles and Practice*, Springer-Verlag (1994); Sambrook, et al., in Molecular Cloning: *A Laboratory Manual*; Ausubel et al., *Current Protocols in Molecular Biology*. Polypeptide fragments that retain biological/immunological activity include fragments comprising greater than about 100 amino acids, or greater than about 200 amino acids, and fragments that encode specific protein domains.

The purified polypeptides can be used in in vitro binding assays which are well known in the art to identify molecules which bind to the polypeptides. These molecules include but are not limited to, for e.g., small molecules, molecules from combinatorial libraries, antibodies or other proteins. The molecules identified in the binding assay are then tested for antagonist or agonist activity in in vivo tissue culture or animal models that are well known in the art. In brief, the molecules are titrated into a plurality of cell cultures or animals and then tested for either cell/animal death or prolonged survival of the animal/cells.

In addition, the peptides of the invention or molecules capable of binding to the peptides may be complexed with toxins, e.g., ricin or cholera, or with other compounds that are toxic to cells. The toxin-binding molecule complex is then targeted to a tumor or other cell by the specificity of the binding molecule for SEQ ID NO: 1–13.

The protein of the invention may also be expressed as a product of transgenic animals, e.g., as a component of the milk of transgenic cows, goats, pigs, or sheep which are characterized by somatic or germ cells containing a nucleotide sequence encoding the protein.

The proteins provided herein also include proteins characterized by amino acid sequences similar to those of purified proteins but into which modification are naturally provided or deliberately engineered. For example, modifications, in the peptide or DNA sequence, can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein. Regions of the protein that are important for the protein function can be determined by various methods known in the art including the alanine-scanning method which involved systematic substitution of single or strings of amino acids with alanine, followed by testing the resulting alanine-containing variant for biological activity. This type of analysis determines the importance of the substituted amino acid(s) in biological activity. Regions of the protein that are important for protein function may be determined by the eMATRIX program.

Other fragments and derivatives of the sequences of proteins which would be expected to retain protein activity in whole or in part and are useful for screening or other immunological methodologies may also be easily made by those skilled in the art given the disclosures herein. Such modifications are encompassed by the present invention.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBat™ kit), and such methods are well known in the art, as described in Summers and Smith, Texas Agricultural Experiment Station Bulletin No. 1555 (1987), incorporated herein by reference. As used herein, an insect cell capable of expressing a polynucleotide of the present invention is "transformed."

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, heparin-toyopearl™ or Cibacrom blue 3GA Sepharose™; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST) or thioredoxin (TRX), or as a His tag. Kits for expression and purification of such fusion proteins are commercially available from New England BioLab (Beverly, Mass.), Pharmacia (Piscataway, N.J.) and Invitrogen, respectively. The protein can also be tagged with an epitope and subsequently purified by using a specific antibody directed to such epitope. One such epitope ("FLAG®") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The polypeptides of the invention include analogs (variants). This embraces fragments, as well as peptides in which one or more amino acids has been deleted, inserted, or substituted. Also, analogs of the polypeptides of the invention embrace fusions of the polypeptides or modifications of the polypeptides of the invention, wherein the polypeptide or analog is fused to another moiety or moieties, e.g., targeting moiety or another therapeutic agent. Such analogs may exhibit improved properties such as activity and/or stability. Examples of moieties which may be fused to the polypeptide or an analog include, for example, targeting moieties which provide for the delivery of polypeptide to pancreatic cells, e.g., antibodies to pancreatic cells, antibodies to immune cells such as T-cells, monocytes, dendritic cells, granulocytes, etc., as well as receptor and ligands expressed on pancreatic or immune cells. Other moieties which may be fused to the polypeptide include therapeutic agents which are used for treatment, for example, immunosuppressive drugs such as cyclosporin, SK506, azathioprine, CD3 antibodies and steroids. Also, polypeptides may be fused to immune modulators, and other cytokines such as alpha or beta interferon.

4.4.1 Determining Polypeptide and Polynucleotide Identity and Similarity

Preferred identity and/or similarity are designed to give the largest match between the sequences tested. Methods to determine identity and similarity are codified in computer programs including, but are not limited to, the GCG program package, including GAP (Devereux, J., et al., Nucleic Acids Research 12(1):387 (1984); Genetics Computer Group, University of Wisconsin, Madison, Wis.), BLASTP, BLASTN, BLASTX, FASTA (Altschul, S. F. et al., J. Molec. Biol. 215:403–410 (1990), PSI-BLAST (Altschul S. F. et al., Nucleic Acids Res. vol. 25, pp. 3389–3402, herein incorporated by reference), eMatrix software (Wu et al., J. Comp. Biol., Vol. 6, pp. 219–235 (1999), herein incorporated by reference), eMotif software (Nevill-Manning et al, ISMB-97, Vol. 4, pp. 202–209, herein incorporated by reference), pFam software (Sonnhammer et al., Nucleic Acids Res., Vol. 26(1), pp. 320–322 (1998), herein incorporated by reference) and the Kyte-Doolittle hydrophobocity prediction algorithm (J. Mol Biol, 157, pp. 105–31 (1982), incorporated herein by reference). The BLAST programs are publicly available from the National Center for Biotechnology Information (NCBI) and other sources (BLAST Manual, Altschul, S., et al. NCB NLM NIH Bethesda, Md. 20894; Altschul, S., et al., J. Mol. Biol. 215:403–410 (1990).

4.5 Gene Therapy

Mutations in the polynucleotides of the invention gene may result in loss of normal function of the encoded protein. The invention thus provides gene therapy to restore normal activity of the polypeptides of the invention; or to treat disease states involving polypeptides of the invention. Delivery of a functional gene encoding polypeptides of the invention to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, for example, Anderson, Nature, supplement to vol. 392, no. 6679, pp.25–20 (1998). For additional reviews of gene therapy technology see Friedmann, Science, 244: 1275–1281 (1989); Verma, Scientific American: 68–84 (1990); and Miller, Nature, 357: 455–460 (1992). Introduction of any one of the nucleotides of the present invention or a gene encoding the polypeptides of the present invention can also be accomplished with extrachromosomal substrates (transient expression) or artificial chromosomes (stable expression). Cells may also be cultured ex vivo in the presence of proteins of the present invention in order to proliferate or to produce a desired effect on or activity in such cells. Treated cells can then be introduced in vivo for therapeutic purposes. Alternatively, it is contemplated that in other human disease states, preventing the expression of or inhibiting the activity of polypeptides of the invention will be useful in treating the disease states. It is contemplated that antisense therapy or gene therapy could be applied to negatively regulate the expression of polypeptides of the invention.

Other methods inhibiting expression of a protein include the introduction of antisense molecules to the nucleic acids of the present invention, their complements, or their translated RNA sequences, by methods known in the art. Further, the polypeptides of the present invention can be inhibited by using targeted deletion methods, or the insertion of a negative regulatory element such as a silencer, which is tissue specific.

The present invention still further provides cells genetically engineered in vivo to express the polynucleotides of the invention, wherein such polynucleotides are in operative association with a regulatory sequence heterologous to the host cell which drives expression of the polynucleotides in the cell. These methods can be used to increase or decrease the expression of the polynucleotides of the present invention.

Knowledge of DNA sequences provided by the invention allows for modification of cells to permit, increase, or decrease, expression of endogenous polypeptide. Cells can be modified (e.g., by homologous recombination) to provide increased polypeptide expression by replacing, in whole or in part, the naturally occurring promoter with all or part of a heterologous promoter so that the cells express the protein at higher levels. The heterologous promoter is inserted in such a manner that it is operatively linked to the desired protein encoding sequences. See, for example, PCT International Publication No. WO 94/12650, PCT International Publication No. WO 92/20808, and PCT International Publication No. WO 91/09955. It is also contemplated that, in addition to heterologous promoter DNA, amplifiable marker DNA (e.g., ada, dhfr, and the multifunctional CAD gene which encodes carbamyl phosphate synthase, aspartate transcarbamylase, and dihydroorotase) and/or intron DNA may be inserted along with the heterologous promoter DNA. If linked to the desired protein coding sequence, amplification of the marker DNA by standard selection methods results in co-amplification of the desired protein coding sequences in the cells.

In another embodiment of the present invention, cells and tissues may be engineered to express an endogenous gene comprising the polynucleotides of the invention under the control of inducible regulatory elements, in which case the regulatory sequences of the endogenous gene may be replaced by homologous recombination. As described herein, gene targeting can be used to replace a gene's existing regulatory region with a regulatory sequence isolated from a different gene or a novel regulatory sequence synthesized by genetic engineering methods. Such regulatory sequences may be comprised of promoters, enhancers, scaffold-attachment regions, negative regulatory elements, transcriptional initiation sites, regulatory protein binding sites or combinations of said sequences. Alternatively, sequences which affect the structure or stability of the RNA or protein produced may be replaced, removed, added, or otherwise modified by targeting. These sequences include polyadenylation signals, mRNA stability elements, splice sites, leader sequences for enhancing or modifying transport or secretion properties of the protein, or other sequences which alter or improve the function or stability of protein or RNA molecules.

The targeting event may be a simple insertion of the regulatory sequence, placing the gene under the control of the new regulatory sequence, e.g., inserting a new promoter or enhancer or both upstream of a gene. Alternatively, the targeting event may be a simple deletion of a regulatory element, such as the deletion of a tissue-specific negative regulatory element. Alternatively, the targeting event may replace an existing element; for example, a tissue-specific enhancer can be replaced by an enhancer that has broader or different cell-type specificity than the naturally occurring elements. Here, the naturally occurring sequences are deleted and new sequences are added. In all cases, the identification of the targeting event may be facilitated by the use of one or more selectable marker genes that are contiguous with the targeting DNA, allowing for the selection of cells in which the exogenous DNA has integrated into the cell genome. The identification of the targeting event may also be facilitated by the use of one or more marker genes exhibiting the property of negative selection, such that the negatively selectable marker is linked to the exogenous DNA, but configured such that the negatively selectable marker flanks the targeting sequence, and such that a correct homologous recombination event with sequences in the host cell genome does not result in the stable integration of the negatively selectable marker. Markers useful for this purpose include the Herpes Simplex Virus thymidine kinase (TK) gene or the bacterial xanthine-guanine phosphoribosyl-transferase (gpt) gene.

The gene targeting or gene activation techniques which can be used in accordance with this aspect of the invention are more particularly described in U.S. Pat. No. 5,272,071 to Chappel; U.S. Pat. No. 5,578,461 to Sherwin et al.; International Application No. PCT/US92/09627 (WO93/09222) by Selden et al.; and International Application No. PCT/US90/06436 (WO91/06667) by Skoultchi et al., each of which is incorporated by reference herein in its entirety.

4.6 Transgenic Animals

In preferred methods to determine biological functions of the polypeptides of the invention in vivo, one or more genes provided by the invention are either over expressed or inactivated in the germ line of animals using homologous recombination [Capecchi, Science 244:1288–1292 (1989)]. Animals in which the gene is over expressed, under the regulatory control of exogenous or endogenous promoter elements, are known as transgenic animals. Animals in which an endogenous gene has been inactivated by homologous recombination are referred to as "knockout" animals. Knockout animals, preferably non-human mammals, can be prepared as described in U.S. Pat. No. 5,557,032, incorporated herein by reference. Transgenic animals are useful to determine the roles polypeptides of the invention play in biological processes, and preferably in disease states. Transgenic animals are useful as model systems to identify compounds that modulate lipid metabolism. Transgenic animals, preferably non-human mammals, are produced using methods as described in U.S. Pat. No 5,489,743 and PCT Publication No. WO094/28122, incorporated herein by reference.

Transgenic animals can be prepared wherein all or part of a promoter of the polynucleotides of the invention is either activated or inactivated to alter the level of expression of the polypeptides of the invention. Inactivation can be carried out using homologous recombination methods described above. Activation can be achieved by supplementing or even replacing the homologous promoter to provide for increased protein expression. The homologous promoter can be supplemented by insertion of one or more heterologous enhancer elements known to confer promoter activation in a particular tissue.

The polynucleotides of the present invention also make possible the development, through, e.g., homologous recombination or knock out strategies, of animals that fail to express polypeptides of the invention or that express a variant polypeptide. Such animals are useful as models for studying the in vivo activities of polypeptide as well as for studying modulators of the polypeptides of the invention.

In preferred methods to determine biological functions of the polypeptides of the invention in vivo, one or more genes provided by the invention are either over expressed or inactivated in the germ line of animals using homologous recombination [Capecchi, Science 244:1288–1292 (1989)]. Animals in which the gene is over expressed, under the regulatory control of exogenous or endogenous promoter elements, are known as transgenic animals. Animals in which an endogenous gene has been inactivated by homologous recombination are referred to as "knockout" animals. Knockout animals, preferably non-human mammals, can be prepared as described in U.S. Pat. No. 5,557,032, incorporated herein by reference. Transgenic animals are useful to determine the roles polypeptides of the invention play in biological processes, and preferably in disease states. Transgenic animals are useful as model systems to identify compounds that modulate lipid metabolism. Transgenic animals, preferably non-human mammals, are produced using methods as described in U.S. Pat. No 5,489,743 and PCT Publication No. WO94/28122, incorporated herein by reference.

Transgenic animals can be prepared wherein all or part of the polynucleotides of the invention promoter is either activated or inactivated to alter the level of expression of the polypeptides of the invention. Inactivation can be carried out using homologous recombination methods described above. Activation can be achieved by supplementing or even replacing the homologous promoter to provide for increased protein expression. The homologous promoter can be supplemented by insertion of one or more heterologous enhancer elements known to confer promoter activation in a particular tissue.

4.7 Uses and Biological Activity

The polynucleotides and proteins of the present invention are expected to exhibit one or more of the uses or biological activities (including those associated with assays cited herein) identified herein. Uses or activities described for proteins of the present invention may be provided by administration or use of such proteins or of polynucleotides encoding such proteins (such as, for example, in gene therapies or vectors suitable for introduction of DNA). The mechanism underlying the particular condition or pathology will dictate whether the polypeptides of the invention, the polynucleotides of the invention or modulators (activators or inhibitors) thereof would be beneficial to the subject in need of treatment. Thus, "therapeutic compositions of the invention" include compositions comprising isolated polynucleotides (including recombinant DNA molecules, cloned genes and degenerate variants thereof) or polypeptides of the invention (including full length protein, mature protein and truncations or domains thereof), or compounds and other substances that modulate the overall activity of the target gene products, either at the level of target gene/protein expression or target protein activity. Such modulators include polypeptides, analogs, (variants), including fragments and fusion proteins, antibodies and other binding proteins; chemical compounds that directly or indirectly activate or inhibit the polypeptides of the invention (identified, e.g., via drug screening assays as described herein); antisense polynucleotides and polynucleotides suitable for triple helix formation; and in particular antibodies or other binding partners that specifically recognize one or more epitopes of the polypeptides of the invention.

The polypeptides of the present invention may likewise be involved in cellular activation or in one of the other physiological pathways described herein.

4.7.1 Research Uses and Utilities

The polynucleotides provided by the present invention can be used by the research community for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., Cell 75:791–803 (1993)) to identify polynucleotides encoding the other protein with which binding occurs or to identify inhibitors of the binding interaction.

The polypeptides provided by the present invention can similarly be used in assays to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding polypeptide is preferentially expressed (either constitutively or at a particular stage of tissue differentiation or development or in a disease state); and, of course, to isolate correlative receptors or ligands. Proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

4.7.2 Nutritional Uses

Polynucleotides and polypeptides of the present invention can also be used as nutritional sources or supplements. Such uses include without limitation use as a protein or amino acid supplement, use as a carbon source, use as a nitrogen source and use as a source of carbohydrate. In such cases the polypeptide or polynucleotide of the invention can be added to the feed of a particular organism or can be administered as a separate solid or liquid preparation, such as in the form of powder, pills, solutions, suspensions or capsules. In the case of microorganisms, the polypeptide or polynucleotide of the invention can be added to the medium in or on which the microorganism is cultured.

4.7.3 Cytokine and Cell Proliferation/Differentiation Activity

A polypeptide of the present invention may exhibit activity relating to cytokine, cell proliferation (either inducing or inhibiting) or cell differentiation (either inducing or inhibiting) activity or may induce production of other cytokines in certain cell populations. A polynucleotide of the invention can encode a polypeptide exhibiting such attributes. Many protein factors discovered to date, including all known cytokines, have exhibited activity in one or more factor-dependent cell proliferation assays, and hence the assays serve as a convenient confirmation of cytokine activity. The activity of therapeutic compositions of the present invention is evidenced by any one of a number of routine factor dependent cell proliferation assays for cell lines including, without limitation, 32D, DA2, DA1G, T10, B9, B9/11, BaF3, MC9/G, M+(preB M+), 2E8, RB5, DA1, 123, T1165, HT2, CTLL2, TF-1, Mo7e, CMK, HUVEC, and Caco. Therapeutic compositions of the invention can be used in the following:

Assays for T-cell or thymocyte proliferation include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Bertagnolli et al., J. Immunol. 145:1706–1712, 1990; Bertagnolli et al., Cellular Immunology 133:327–341, 1991; Bertagnolli, et al., I. Immunol. 149:3778–3783, 1992; Bowman et al., I. Immunol. 152:1756–1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In Current Protocols in Immunology. J. E. e.a. Coligan eds. Vol 1 pp. 3.12.1–3.12.14, John Wiley and Sons, Toronto. 1994; and Measurement of mouse and human interleukin- , Schreiber, R. D. In Current Protocols in Immunology. J. E. e.a. Coligan eds. Vol 1 pp. 6.8.1–6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In Current Protocols in Immunology. J. E. e.a. Coligan eds. Vol 1 pp. 6.3.1–6.3.12, John Wiley and Sons, Toronto. 1991; deVries et al., J. Exp. Med. 173:1205–1211, 1991; Moreau et al., Nature 336:690–692, 1988; Greenberger et al., Proc. Natl. Acad. Sci. U.S.A. 80:2931–2938, 1983; Measurement of mouse and human interleukin 6—Nordan, R. In Current Protocols in Immunology. J. E. Coligan eds. Vol 1 pp. 6.6.1–6.6.5, John Wiley and Sons, Toronto. 1991; Smith et al., Proc. Natl. Aced. Sci. U.S.A. 83:1857–1861, 1986; Measurement of human Interleukin 11—Bennett, F., Giannotti, J., Clark, S. C. and Turner, K. J. In Current Protocols in Immunology. J. E. Coligan eds. Vol 1 pp. 6.15.1 John Wiley and Sons, Toronto. 1991; Measurement of mouse and human Interleukin 9—Ciarletta, A., Giannotti, J., Clark, S. C. and Turner, K. J. In Current Protocols in Immunology. J. E. Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. USA 77:6091–6095, 1980; Weinberger et al., Eur. J. Immun. 11:405–411, 1981; Takai et al., J. Immunol. 137:3494–3500, 1986; Takai et al., J. Immunol. 140:508–512, 1988.

4.7.4 Stem Cell Growth Factor Activity

A polypeptide of the present invention may exhibit stem cell growth factor activity and be involved in the proliferation, differentiation and survival of pluripotent and totipotent stem cells including primordial germ cells, embryonic stem cells, hematopoietic stem cells and/or germ line stem cells. Administration of the polypeptide of the invention to stem cells in vivo or ex vivo is expected to maintain and expand cell populations in a totipotential or pluripotential state which would be useful for re-engineering damaged or diseased tissues, transplantation, manufacture of biopharmaceuticals and the development of bio-sensors. The ability to produce large quantities of human cells has important working applications for the production of human proteins which currently must be obtained from non-human sources or donors, implantation of cells to treat diseases such as Parkinson's, Alzheimer's and other neurodegenerative diseases; tissues for grafting such as bone marrow, skin, cartilage, tendons, bone, muscle (including cardiac muscle), blood vessels, cornea, neural cells, gastrointestinal cells and others; and organs for transplantation such as kidney, liver, pancreas (including islet cells), heart and lung.

It is contemplated that multiple different exogenous growth factors and/or cytokines may be administered in combination with the polypeptide of the invention to achieve the desired effect, including any of the growth factors listed herein, other stem cell maintenance factors, and specifically including stem cell factor (SCF), leukemia inhibitory factor (LIF), Flt-3 ligand (Flt-3L), any of the interleukins, recombinant soluble IL-6 receptor fused to IL-6, macrophage inflammatory protein 1-alpha (MIP-1-alpha), G-CSF, GM-CSF, thrombopoietin (TPO), platelet factor 4 (PF-4), platelet-derived growth factor (PDGF), neural growth factors and basic fibroblast growth factor (bFGF).

Since totipotent stem cells can give rise to virtually any mature cell type, expansion of these cells in culture will facilitate the production of large quantities of mature cells. Techniques for culturing stem cells are known in the art and administration of polypeptides of the invention, optionally with other growth factors and/or cytokines, is expected to enhance the survival and proliferation of the stem cell populations. This can be accomplished by direct administration of the polypeptide of the invention to the culture medium. Alternatively, stroma cells transfected with a polynucleotide that encodes for the polypeptide of the invention can be used as a feeder layer for the stem cell populations in culture or in vivo. Stromal support cells for feeder layers may include embryonic bone marrow fibroblasts, bone marrow stromal cells, fetal liver cells, or cultured embryonic fibroblasts (see U.S. Pat. No. 5,690,926).

Stem cells themselves can be transfected with a polynucleotide of the invention to induce autocrine expression of the polypeptide of the invention. This will allow for generation of undifferentiated totipotential/pluripotential stem cell lines that are useful as is or that can then be differentiated into the desired mature cell types. These stable cell lines can also serve as a source of undifferentiated totipotential/pluripotential mRNA to create cDNA libraries and templates for polymerase chain reaction experiments. These studies would allow for the isolation and identification of differentially expressed genes in stem cell populations that regulate stem cell proliferation and/or maintenance.

Expansion and maintenance of totipotent stem cell populations will be useful in the treatment of many pathological conditions. For example, polypeptides of the present invention may be used to manipulate stem cells in culture to give rise to neuroepithelial cells that can be used to augment or replace cells damaged by illness, autoimmune disease, accidental damage or genetic disorders. The polypeptide of the invention may be useful for inducing the proliferation of neural cells and for the regeneration of nerve and brain tissue, i.e. for the treatment of central and peripheral nervous system diseases and neuropathies, as well as mechanical and traumatic disorders which involve degeneration, death or trauma to neural cells or nerve tissue. In addition, the expanded stem cell populations can also be genetically altered for gene therapy purposes and to decrease host rejection of replacement tissues after grafting or implantation.

Expression of the polypeptide of the invention and its effect on stem cells can also be manipulated to achieve controlled differentiation of the stem cells into more differentiated cell types. A broadly applicable method of obtaining pure populations of a specific differentiated cell type from undifferentiated stem cell populations involves the use of a cell-type specific promoter driving a selectable marker. The selectable marker allows only cells of the desired type to survive. For example, stem cells can be induced to differentiate into cardiomyocytes (Wobus et al., Differentiation, 48: 173–182, (1991); Klug et al., J. Clin. Invest., 98(1): 216–224, (1998)) or skeletal muscle cells (Browder, L. W. In: *Principles of Tissue Engineering eds.* Lanza et al., Academic Press (1997)). Alternatively, directed differentiation of stem cells can be accomplished by culturing the stem cells in the presence of a differentiation factor such as retinoic acid and an antagonist of the polypeptide of the invention which would inhibit the effects of endogenous stem cell factor activity and allow differentiation to proceed.

In vitro cultures of stem cells can be used to determine if the polypeptide of the invention exhibits stem cell growth factor activity. Stem cells are isolated from any one of various cell sources (including hematopoietic stem cells and embryonic stem cells) and cultured on a feeder layer, as described by Thompson et al. Proc. Natl. Acad. Sci, U.S.A., 92: 7844–7848 (1995), in the presence of the polypeptide of the invention alone or in combination with other growth factors or cytokines. The ability of the polypeptide of the invention to induce stem cells proliferation is determined by colony formation on semi-solid support e.g. as described by Bernstein et al., Blood, 77: 2316–2321 (1991).

4.7.5 Hematopoiesis Regulating Activity

A polypeptide of the present invention may be involved in regulation of hematopoiesis and, consequently, in the treatment of myeloid or lymphoid cell disorders. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelosuppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

Therapeutic compositions of the invention can be used in the following:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. Cellular Biology 15:141–151, 1995; Keller et al., Molecular and Cellular Biology 13:473–486, 1993; McClanahan et al., Blood 81:2903–2915, 1993.

Assays for stem cell survival and differentiation (which will identify, among others, proteins that regulate lympho-hematopoiesis) include, without limitation, those described in: Methylcellulose colony forming assays, Freshney, M. G. In Culture of Hematopoietic Cells. R. I. Freshney, et al. eds. Vol pp. 265–268, Wiley-Liss, Inc., New York, N.Y. 1994; Hirayama et al., Proc. Natl. Acad. Sci. USA 89:5907–5911, 1992; Primitive hematopoietic colony forming cells with high proliferative potential, McNiece, I. K. and Briddell, R. A. In Culture of Hematopoietic Cells. R. I. Freshney, et al. eds. Vol pp. 23–39, Wiley-Liss, Inc., New York, N.Y. 1994; Neben et al., Experimental Hematology 22:353–359, 1994; Cobblestone area forming cell assay, Ploemacher, R. E. In Culture of Hematopoietic Cells. R. I. Freshney, et al. eds. Vol pp. 1–21, Wiley-Liss, Inc., New York, N.Y. 1994; Long term bone marrow cultures in the presence of stromal cells, Spooncer, E., Dexter, M. and Allen, T. In Culture of Hematopoietic Cells. R. I. Freshney, et al. eds. Vol pp. 163–179, Wiley-Liss, Inc., New York, N.Y. 1994; Long term culture initiating cell assay, Sutherland, H. J. In Culture of Hematopoietic Cells. R. I. Freshney, et al. eds. Vol pp. 139–162, Wiley-Liss, Inc., New York, N.Y. 1994.

4.7.6 Tissue Growth Activity

A polypeptide of the present invention also may be involved in bone, cartilage, tendon, ligament and/or nerve tissue growth or regeneration, as well as in wound healing and tissue repair and replacement, and in healing of bums, incisions and ulcers.

A polypeptide of the present invention which induces cartilage and/or bone growth in circumstances where bone is not normally formed, has application in the healing of bone fractures and cartilage damage or defects in humans and other animals. Compositions of a polypeptide, antibody, binding partner, or other modulator of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A polypeptide of this invention may also be involved in attracting bone-forming cells, stimulating growth of bone-forming cells, or inducing differentiation of progenitors of bone-forming cells. Treatment of osteoporosis, osteoarthritis, bone degenerative disorders, or periodontal disease, such as through stimulation of bone and/or cartilage repair or by blocking inflammation or processes of tissue destruction (collagenase activity, osteoclast activity, etc.) mediated by inflammatory processes may also be possible using the composition of the invention.

Another category of tissue regeneration activity that may involve the polypeptide of the present invention is tendon/ligament formation. Induction of tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The compositions of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a composition may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a composition of the invention.

Compositions of the invention may also be useful to promote better or faster closure of non-healing wounds, including without limitation pressure ulcers, ulcers associated with vascular insufficiency, surgical and traumatic wounds, and the like.

Compositions of the present invention may also be involved in the generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects may be by inhibition or modulation of fibrotic scarring may allow normal tissue to regenerate. A polypeptide of the present invention may also exhibit angiogenic activity.

A composition of the present invention may also be useful for gut protection or regeneration and treatment of lung or liver fibrosis, reperfusion injury in various tissues, and conditions resulting from systemic cytokine damage.

A composition of the present invention may also be useful for promoting or inhibiting differentiation of tissues described above from precursor tissues or cells; or for inhibiting the growth of tissues described above.

Therapeutic compositions of the invention can be used in the following:

Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium).

Assays for wound healing activity include, without limitation, those described in: Winter, Epidermal Wound Healing, pps. 71–112 (Maibach, H. I. and Rovee, D. T., eds.), Year Book Medical Publishers, Inc., Chicago, as modified by Eaglstein and Mertz, J. Invest. Dermatol 71:382–84 (1978).

4.7.7 Immune Stimulating or Suppressing Activity

A polypeptide of the present invention may also exhibit immune stimulating or immune suppressing activity, including without limitation the activities for which assays are described herein. A polynucleotide of the invention can encode a polypeptide exhibiting such activities. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases causes by viral, bacterial, fungal or other infection may be treatable using a protein of the present invention, including infections by HIV, hepatitis viruses, herpes viruses, mycobacteria, Leishmania spp., malaria spp. and various fungal infections such as candidiasis. Of course, in this regard, proteins of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Such a protein (or antagonists thereof, including antibodies) of the present invention may also to be usefall in the treatment of allergic reactions and conditions (e.g., anaphylaxis, serum sickness, drug reactions, food allergies, insect venom allergies, mastocytosis, allergic rhinitis, hypersensitivity pneumonitis, urticaria, angioedema, eczema, atopic dermatitis, allergic contact dermatitis, erythema multiforme, Stevens-Johnson syndrome, allergic conjunctivitis, atopic keratoconjunctivitis, venereal keratoconjunctivitis, giant papillary conjunctivitis and contact allergies), such as asthma (particularly allergic asthma) or other respiratory problems. Other conditions, in which immune suppression is desired (including, for example, organ transplantation), may also be treatable using a protein (or antagonists thereof) of the present invention. The therapeutic effects of the polypeptides or antagonists thereof on allergic reactions can be evaluated by in vivo animals models such as the cumulative contact enhancement test (Lastbom et al., Toxicology 125: 59–66, 1998), skin prick test (Hoffmann et al., Allergy 54: 446–54, 1999), guinea pig skin sensitization test (Vohr et al., Arch. Toxocol. 73: 501–9), and murine local lymph node assay (Kimber et al., J. Toxicol. Environ. Health 53: 563–79).

Using the proteins of the invention it may also be possible to modulate immune responses, in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a therapeutic composition of the invention may prevent cytokine synthesis by immune cells, such as T cells, and thus acts as an immunosuppressant. Moreover, a lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular therapeutic compositions in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789–792 (1992) and Turka et al., Proc. Natl. Acad. Sci USA, 89:11102–11105 (1992). In addition, murine models of GVHD (see Paul ed., Fundamental Immunology, Raven Press, New York, 1989, pp. 846–847) can be used to determine the effect of therapeutic compositions of the invention on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block stimulation of T cells can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoinimune encephalitis, systemic lupus erythlmatosis in MRL/lpr/lpr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840–856).

Upregulation of an antigen function (e.g., a B lymphocyte antigen function), as a means of up regulating immune responses, may also be useful in therapy. Upregulation of immune responses may be in the form of enhancing an existing immune response or eliciting an initial immune response. For example, enhancing an immune response may be useful in cases of viral infection, including systemic viral diseases such as influenza, the common cold, and encephalitis.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-viral immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

A polypeptide of the present invention may provide the necessary stimulation signal to T cells to induce a T cell mediated immune response against the transfected tumor cells. In addition, tumor cells which lack MHC class I or MHC class II molecules, or which fail to reexpress sufficient mounts of MHC class I or MHC class II molecules, can be transfected with nucleic acid encoding all or a portion of (e.g., a cytoplasmic-domain truncated portion) of an MHC class I alpha chain protein and $\beta_2$ microglobulin protein or an MHC class II alpha chain protein and an MHC class II beta chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a protein of the invention may, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., I. Immunol. 137:3494–3500, 1986; Takai et al., J. Immunol. 140:508–512, 1988; Bowman et al., J. Virology 61:1992–1998; Bertagnolli et al., Cellular Immunology 133:327–341, 1991; Brown et al., J. Immunol. 153:3079–3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028–3033, 1990; and Assays for B cell function: In vitro antibody production, Mond, J. J. and Brunswick, M. In Current Protocols in Immunology. J. E. e.a. Coligan eds. Vol 1 pp. 3.8.1–3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Takai et al., J. Immunol. 140:508–512, 1988; Bertagnolli et al., J. Immunol. 149:3778–3783, 1992.

Dendritic cell-dependent assays (which will identify, among others, proteins expressed by dendritic cells that activate naive T-cells) include, without limitation, those described in: Guery et al., J. Immunol. 134:536–544, 1995; Inaba et al., Journal of Experimental Medicine 173:549–559, 1991; Macatonia et al., Journal of Immunology 154:5071–5079, 1995; Porgador et al., Journal of Experimental Medicine 182:255–260, 1995; Nair et al., Journal of Virology 67:4062–4069, 1993; Huang et al., Science 264:961–965, 1994; Macatonia et al., Journal of Experimental Medicine 169:1255–1264, 1989; Bhardwaj et al., Journal of Clinical Investigation 94:797–807, 1994; and Inaba et al., Journal of Experimental Medicine 172:631–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795–808, 1992; Gorczyca et al., Leukemia 7:659–670, 1993; Gorczyca et al., Cancer Research 53:1945–1951, 1993; Itoh et al., Cell 66:233–243, 1991; Zacharchuk, Journal of Immunology 145:4037–4045, 1990; Zamai et al., Cytometry 14:891–897, 1993; Gorczyca et al., International Journal of Oncology 1:639–648, 1992.

Assays for proteins that influence early steps of T-cell commitment and development include, without limitation, those described in: Antica et al., Blood 84:111–117, 1994; Fine et al., Cellular Immunology 155:111–122, 1994; Galy et al., Blood 85:2770–2778, 1995; Toki et al., Proc. Nat. Acad Sci. USA 88:7548–7551, 1991.

4.7.8 Activin/Inhibin Activity

A polypeptide of the present invention may also exhibit activin- or inhibin-related activities. A polynucleotide of the invention may encode a polypeptide exhibiting such characteristics. Inhibins are characterized by their ability to inhibit the release of follicle stimulating hormone (FSH), while activins and are characterized by their ability to stimulate the release of follicle stimulating hormone (FSH). Thus, a polypeptide of the present invention, alone or in heterodimers with a member of the inhibin family, may be useful as a contraceptive based on the ability of inhibins to decrease fertility in female mammals and decrease spermatogenesis in male mammals. Administration of sufficient amounts of other inhibins can induce infertility in these mammals. Alternatively, the polypeptide of the invention, as a homodimer or as a heterodimer with other protein subunits of the inhibin group, may be useful as a fertility inducing therapeutic, based upon the ability of activin molecules in stimulating FSH release from cells of the anterior pituitary. See, for example, U.S. Pat. No. 4,798,885. A polypeptide of the invention may also be useful for advancement of the onset of fertility in sexually immature mammals, so as to increase the lifetime reproductive performance of domestic animals such as, but not limited to, cows, sheep and pigs.

The activity of a polypeptide of the invention may, among other means, be measured by the following methods.

Assays for activin/inhibin activity include, without limitation, those described in: Vale et al., Endocrinology 91:562–572, 1972; Ling et al., Nature 321:779–782, 1986; Vale et al., Nature 321:776–779, 1986; Mason et al., Nature 318:659–663, 1985; Forage et al., Proc. Natl. Acad. Sci. USA 83:3091–3095, 1986.

4.7.9 Chemotactic/Chemokinetic Activity

A polypeptide of the present invention may be involved in chemotactic or chemokinetic activity for mammalian cells, including, for example, monocytes, fibroblasts, neutrophils, T-cells, mast cells, eosinophils, epithelial and/or endothelial cells. A polynucleotide of the invention can encode a polypeptide exhibiting such attributes. Chemotactic and chemokinetic receptor activation can be used to mobilize or attract a desired cell population to a desired site of action. Chemotactic or chemokinetic compositions (e.g. proteins, antibodies, binding partners, or modulators of the invention) provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

Therapeutic compositions of the invention can be used in the following:

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed by J. E. Coligan, A. M. Kruisbeek, D. H. Marguiles, E. M. Shevach, W. Strober, Pub. Greene Publishing Associates and Wiley-Interscience (Chapter 6.12, Measurement of alpha and beta Chemokines 6.12.1–6.12.28; Taub et al. J. Clin. Invest. 95:1370–1376, 1995; Lind et al. APMIS 103:140–146, 1995; Muller et al Eur. J. Immunol. 25:1744–1748; Gruber et al. J. of Immunol. 152:5860–5867, 1994; Johnston et al. J. of Immunol. 153:1762–1768, 1994.

4.7.10 Hemostatic and Thrombolytic Activity

A polypeptide of the invention may also be involved in hemostatis or thrombolysis or thrombosis. A polynucleotide of the invention can encode a polypeptide exhibiting such attributes. Compositions may be useful in treatment of various coagulation disorders (including hereditary disorders, such as hemophilias) or to enhance coagulation and other hemostatic events in treating wounds resulting from trauma, surgery or other causes. A composition of the invention may also be useful for dissolving or inhibiting formation of thromboses and for treatment and prevention of conditions resulting therefrom (such as, for example, infarction of cardiac and central nervous system vessels (e.g., stroke).

Therapeutic compositions of the invention can be used in the following:

Assay for hemostatic and thrombolytic activity include, without limitation, those described in: Linet et al., J. Clin. Pharmacol. 26:131–140, 1986; Burdick et al., Thrombosis Res. 45:413–419, 1987; Humphrey et al., Fibrinolysis 5:71–79 (1991); Schaub, Prostaglandins 35:467–474, 1988.

4.7.11 Cancer Diagnosis and Therapy

Polypeptides of the invention may be involved in cancer cell generation, proliferation or metastasis. Detection of the presence or amount of polynucleotides or polypeptides of the invention may be useful for the diagnosis and/or prognosis of one or more types of cancer. For example, the presence or increased expression of a polynucleotide/polypeptide of the invention may indicate a hereditary risk of cancer, a precancerous condition, or an ongoing malignancy. Conversely, a defect in the gene or absence of the polypeptide may be associated with a cancer condition. Identification of single nucleotide polymorphisms associated with cancer or a predisposition to cancer may also be useful for diagnosis or prognosis.

Cancer treatments promote tumor regression by inhibiting tumor cell proliferation, inhibiting angiogenesis (growth of new blood vessels that is necessary to support tumor growth) and/or prohibiting metastasis by reducing tumor cell motility or invasiveness. Therapeutic compositions of the invention may be effective in adult and pediatric oncology including in solid phase tumors/malignancies, locally advanced tumors, human soft tissue sarcomas, metastatic cancer, including lymphatic metastases, blood cell malignancies including multiple myeloma, acute and chronic leukemias, and lymphomas, head and neck cancers including mouth cancer, larynx cancer and thyroid cancer, lung cancers including small cell carcinoma and non-small cell cancers, breast cancers including small cell carcinoma and ductal carcinoma, gastrointestinal cancers including esophageal cancer, stomach cancer, colon cancer, colorectal cancer and polyps associated with colorectal neoplasia, pancreatic cancers, liver cancer, urologic cancers including bladder cancer and prostate cancer, malignancies of the female genital tract including ovarian carcinoma, uterine (including endometrial) cancers, and solid tumor in the ovarian follicle, kidney cancers including renal cell carcinoma, brain cancers including intrinsic brain tumors, neuroblastoma, astrocytic brain tumors, gliomas, metastatic tumor cell invasion in the central nervous system, bone cancers including osteomas, skin cancers including malignant melanoma, tumor progression of human skin keratinocytes, squamous cell carcinoma, basal cell carcinoma, hemangiopericytoma and Karposi's sarcoma.

Polypeptides, polynucleotides, or modulators of polypeptides of the invention (including inhibitors and stimulators of the biological activity of the polypeptide of the invention) may be administered to treat cancer. Therapeutic compositions can be administered in therapeutically effective dosages alone or in combination with adjuvant cancer therapy such as surgery, chemotherapy, radiotherapy, thermotherapy, and laser therapy, and may provide a beneficial effect, e.g. reducing tumor size, slowing rate of tumor growth, inhibiting metastasis, or otherwise improving overall clinical condition, without necessarily eradicating the cancer.

The composition can also be administered in therapeutically effective amounts as a portion of an anti-cancer cocktail. An anti-cancer cocktail is a mixture of the polypeptide or modulator of the invention with one or more anti-cancer drugs in addition to a pharmaceutically acceptable carrier for delivery. The use of anti-cancer cocktails as a cancer treatment is routine. Anti-cancer drugs that are well known in the art and can be used as a treatment in combination with the polypeptide or modulator of the invention include: Actinomycin D, Aminoglutethimide, Asparaginase, Bleomycin, Busulfan, Carboplatin, Carmustine, Chlorambucil, Cisplatin (cis-DDP), Cyclophosphamide, Cytarabine HCl (Cytosine arabinoside), Dacarbazine, Dactinomycin, Daunorubicin HCl, Doxorubicin HCl, Estramustine phosphate sodium, Etoposide (V16–213), Floxuridine, 5-Fluorouracil (5-Fu), Flutamide, Hydroxyurea (hydroxycarbamide), Ifosfamide, Interferon Alpha-2a, Interferon Alpha-2b, Leuprolide acetate (LHRH-releasing factor analog), Lomustine, Mechlorethamine HCI (nitrogen mustard), Melphalan, Mercaptopurine, Mesna, Methotrexate (MTX), Mitomycin, Mitoxantrone HCl, Octreotide, Plicamycin, Procarbazine HCl, Streptozocin, Tamoxifen citrate, Thioguanine, Thiotepa, Vinblastine sulfate, Vincristine sulfate, Amsacrine, Azacitidine, Hexamethylmelamine, Interleukin-2, Mitoguazone, Pentostatin, Semustine, Teniposide, and Vindesine sulfate.

In addition, therapeutic compositions of the invention may be used for prophylactic treatment of cancer. There are hereditary conditions and/or environmental situations (e.g. exposure to carcinogens) known in the art that predispose an individual to developing cancers. Under these circumstances, it may be beneficial to treat these individuals with therapeutically effective doses of the polypeptide of the invention to reduce the risk of developing cancers.

In vitro models can be used to determine the effective doses of the polypeptide of the invention as a potential cancer treatment. These in vitro models include proliferation assays of cultured tumor cells, growth of cultured tumor cells in soft agar (see Freshney, (1987) Culture of Animal Cells: A Manual of Basic Technique, Wily-Liss, New York, N.Y. Ch 18 and Ch 21), tumor systems in nude mice as described in Giovanella et al., J. Natl. Can. Inst., 52: 921–30 (1974), mobility and invasive potential of tumor cells in Boyden Chamber assays as described in Pilkington et al., Anticancer Res., 17: 4107–9 (1997), and angiogenesis assays such as induction of vascularization of the chick chorioallantoic membrane or induction of vascular endothelial cell migration as described in Ribatta et al., Intl. J. Dev. Biol., 40: 1189–97 (1999) and Li et al., Clin. Exp. Metastasis, 17:423–9 (1999), respectively. Suitable tumor cells lines are available, e.g. from American Type Tissue Culture Collection catalogs.

4.7.12 Receptor/Ligand Activity

A polypeptide of the present invention may also demonstrate activity as receptor, receptor ligand or inhibitor or agonist of receptor/ligand interactions. A polynucleotide of the invention can encode a polypeptide exhibiting such characteristics. Examples of such receptors and ligands include, without limitation, cytokine receptors and their ligands, receptor kinases and their ligands, receptor phosphatases and their ligands, receptors involved in cell-cell interactions and their ligands (including without limitation, cellular adhesion molecules (such as selectins, integrins and their ligands) and receptor/ligand pairs involved in antigen presentation, antigen recognition and development of cellular and humoral immune responses. Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The activity of a polypeptide of the invention may, among other means, be measured by the following methods:

Suitable assays for receptor-ligand activity include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 7.28, Measurement of Cellular Adhesion under static conditions 7.28.1–7.28.22), Takai et al., Proc. Natl. Acad. Sci. USA 84:6864–6868, 1987;

Bierer et al., J. Exp. Med. 168:1145–1156, 1988; Rosenstein et al., J. Exp. Med. 169:149–160 1989; Stoltenborg et al., J. Immunol. Methods 175:59–68, 1994; Stitt et al., Cell 80:661–670, 1995.

By way of example, the polypeptides of the invention may be used as a receptor for a ligand(s) thereby transmitting the biological activity of that ligand(s). Ligands may be identified through binding assays, affinity chromatography, dihybrid screening assays, BIAcore assays, gel overlay assays, or other methods known in the art.

Studies characterizing drugs or proteins as agonist or antagonist or partial agonists or a partial antagonist require the use of other proteins as competing ligands. The polypeptides of the present invention or ligand(s) thereof may be labeled by being coupled to radioisotopes, colorimetric molecules or a toxin molecules by conventional methods. ("Guide to Protein Purification" Murray P. Deutscher (ed) Methods in Enzymology Vol. 182 (1990) Academic Press, Inc. San Diego). Examples of radioisotopes include, but are not limited to, tritium and carbon-14. Examples of colorimetric molecules include, but are not limited to, fluorescent molecules such as fluorescamine, or rhodamine or other calorimetric molecules. Examples of toxins include, but are not limited, to ricin.

4.7.13 Drug Screening

This invention is particularly useful for screening chemical compounds by using the novel polypeptides or binding fragments thereof in any of a variety of drug screening techniques. The polypeptides or fragments employed in such a test may either be free in solution, affixed to a solid support, borne on a cell surface or located intracellularly. One method of drug screening utilizes eukaryotic or prokaryotic host cells which are stably transformed with recombinant nucleic acids expressing the polypeptide or a fragment thereof. Drugs are screened against such transformed cells in competitive binding assays. Such cells, either in viable or fixed form, can be used for standard binding assays. One may measure, for example, the formation of complexes between polypeptides of the invention or fragments and the agent being tested or examine the diminution in complex formation between the novel polypeptides and an appropriate cell line, which are well known in the art.

Sources for test compounds that may be screened for ability to bind to or modulate (i.e., increase or decrease) the activity of polypeptides of the invention include (1) inorganic and organic chemical libraries, (2) natural product libraries, and (3) combinatorial libraries comprised of either random or mimetic peptides, oligonucleotides or organic molecules.

Chemical libraries may be readily synthesized or purchased from a number of commercial sources, and may include structural analogs of known compounds or compounds that are identified as "hits" or "leads" via natural product screening.

The sources of natural product libraries are microorganisms (including bacteria and fungi), animals, plants or other vegetation, or marine organisms, and libraries of mixtures for screening may be created by: (1) fermentation and extraction of broths from soil, plant or marine microorganisms or (2) extraction of the organisms themselves. Natural product libraries include polyketides, non-ribosomal peptides, and (non-naturally occurring) variants thereof. For a review, see *Science* 282:63–68 (1998).

Combinatorial libraries are composed of large numbers of peptides, oligonucleotides or organic compounds and can be readily prepared by traditional automated synthesis methods, PCR, cloning or proprietary synthetic methods. Of particular interest are peptide and oligonucleotide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, *Curr. Opin. Biotechnol.* 8:701–707 (1997). For reviews and examples of peptidomimetic libraries, see Al-Obeidi et al., *Mol. Biotechnol*, 9(3):205–23 (1998); Hruby et al., *Curr Opin Chem Biol*, 1(1):114–19 (1997) Dorner et al., *Bioorg Med Chem*, 4(5):709–15 (1996) (alkylated dipeptides).

Identification of modulators through use of the various libraries described herein permits modification of the candidate "hit" (or "lead") to optimize the capacity of the "hit" to bind a polypeptide of the invention. The molecules identified in the binding assay are then tested for antagonist or agonist activity in in vivo tissue culture or animal models that are well known in the art. In brief, the molecules are titrated into a plurality of cell cultures or animals and then tested for either cell/animal death or prolonged survival of the animal/cells.

The binding molecules thus identified may be complexed with toxins, e.g., ricin or cholera, or with other compounds that are toxic to cells such as radioisotopes. The toxin-binding molecule complex is then targeted to a tumor or other cell by the specificity of the binding molecule for a polypeptide of the invention. Alternatively, the binding molecules may be complexed with imaging agents for targeting and imaging purposes.

4.7.14 Assay for Receptor Activity

The invention also provides methods to detect specific binding of a polypeptide e.g. a ligand or a receptor. The art provides numerous assays particularly useful for identifying previously unknown binding partners for receptor polypeptides of the invention. For example, expression cloning using mammalian or bacterial cells, or dihybrid screening assays can be used to identify polynucleotides encoding binding partners. As another example, affinity chromatography with the appropriate immobilized polypeptide of the invention can be used to isolate polypeptides that recognize and bind polypeptides of the invention. There are a number of different libraries used for the identification of compounds, and in particular small molecules, that modulate (i.e., increase or decrease) biological activity of a polypeptide of the invention. Ligands for receptor polypeptides of the invention can also be identified by adding exogenous ligands, or cocktails of ligands to two cells populations that are genetically identical except for the expression of the receptor of the invention: one cell population expresses the receptor of the invention whereas the other does not. The response of the two cell populations to the addition of ligands(s) are then compared. Alternatively, an expression library can be co-expressed with the polypeptide of the invention in cells and assayed for an autocrine response to identify potential ligand(s). As still another example, BIAcore assays, gel overlay assays, or other methods known in the art can be used to identify binding partner polypeptides, including, (1) organic and inorganic chemical libraries, (2) natural product libraries, and (3) combinatorial libraries comprised of random peptides, oligonucleotides or organic molecules.

The role of downstream intracellular signaling molecules in the signaling cascade of the polypeptide of the invention can be determined. For example, a chimeric protein in which the cytoplasmic domain of the polypeptide of the invention is fused to the extracellular portion of a protein, whose ligand has been identified, is produced in a host cell. The cell is then incubated with the ligand specific for the extracellular portion of the chimeric protein, thereby activating the chimeric receptor. Known downstream proteins involved in intracellular signaling can then be assayed for expected modifications i.e. phosphorylation. Other methods known to those in the art can also be used to identify signaling molecules involved in receptor activity.

4.7.15 Anti-inflammatory Activity

Compositions of the present invention may also exhibit anti-inflammatory activity. The anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Compositions with such activities can be used to treat inflammatory conditions including chronic or acute conditions), including without limitation intimation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Compositions of the invention may also be useful to treat anaphylaxis and hypersensitivity to an antigenic substance or material. Compositions of this invention may be utilized to prevent or treat conditions such as, but not limited to, sepsis, acute pancreatitis, endotoxin shock, cytokine induced shock, rheumatoid arthritis, chronic inflammatory arthritis, pancreatic cell damage from diabetes mellitus type 1, graft versus host disease, inflammatory bowel disease, inflamation associated with pulmonary disease, other autoimmune disease or inflammatory disease, an antiproliferative agent such as for acute or chronic mylegenous leukemia or in the prevention of premature labor secondary to intrauterine infections. 4.7.16 Leukemias Leukemias and related disorders may be treated or prevented by administration of a therapeutic that promotes or inhibits function of the polynucleotides and/or polypeptides of the invention. Such leukemias and related disorders include but are not limited to acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia and chronic lymphocytic leukemia (for a review of such disorders, see Fishman et at., 1985, Medicine, 2d Ed., J. B. Lippincott Co., Philadelphia).

4.7.17 Nervous System Disorders

Nervous system disorders, involving cell types which can be tested for efficacy of intervention with compounds that modulate the activity of the polynucleotides and/or polypeptides of the invention, and which can be treated upon thus observing an indication of therapeutic utility, include but are not limited to nervous system injuries, and diseases or disorders which result in either a disconnection of axons, a diminution or degeneration of neurons, or demyelination. Nervous system lesions which may be treated in a patient (including human and non-human mammalian patients) according to the invention include but are not limited to the following lesions of either the central (including spinal cord, brain) or peripheral nervous systems:

(i) traumatic lesions, including lesions caused by physical injury or associated with surgery, for example, lesions which sever a portion of the nervous system, or compression injuries;

(ii) ischemic lesions, in which a lack of oxygen in a portion of the nervous system results in neuronal injury or death, including cerebral infarction or ischemia, or spinal cord infarction or ischemia;

(iii) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis;

(iv) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis;

(v) lesions associated with nutritional diseases or disorders, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;

(vi) neurological lesions associated with systemic diseases including but not limited to diabetes (diabetic neuropathy, Bell's palsy), systemic lupus erythematosus, carcinoma, or sarcoidosis;

(vii) lesions caused by toxic substances including alcohol, lead, or particular neurotoxins; and (viii) demyelinated lesions in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

Therapeutics which are useful according to the invention for treatment of a nervous system disorder may be selected by testing for biological activity in promoting the survival or differentiation of neurons. For example, and not by way of limitation, therapeutics which elicit any of the following effects may be useful according to the invention:

(i) increased survival time of neurons in culture;

(ii) increased sprouting of neurons in culture or in vivo;

(iii) increased production of a neuron-associated molecule in culture or in vivo, e.g., choline acetyltransferase or acetylcholinesterase with respect to motor neurons; or (iv) decreased symptoms of neuron dysfunction in vivo.

Such effects may be measured by any method known in the art. In preferred, non-limiting embodiments, increased survival of neurons may be measured by the method set forth in Arakawa et al. (1990, J. Neurosci. 10:3507–3515); increased sprouting of neurons may be detected by methods set forth in Pestronk et al. (1980, Exp. Neurol. 70:65–82) or Brown et al. (1981, Ann. Rev. Neurosci. 4:17–42); increased production of neuron-associated molecules may be measured by bioassay, enzymatic assay, antibody binding, Northern blot assay, etc., depending on the molecule to be measured; and motor neuron dysfunction may be measured by assessing the physical manifestation of motor neuron disorder, e.g., weakness, motor neuron conduction velocity, or functional disability.

In specific embodiments, motor neuron disorders that may be treated according to the invention include but are not limited to disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including but not limited to progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

4.7.18 Other Activities

A polypeptide of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or circadian cycles or rhythms; effecting the fertility of male or female subjects; effecting the metabolism, catabolism, anabolism, processing, utilization, storage or elimination of dietary fat, lipid, protein, carbohydrate, vitamins, minerals, co-factors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

4.7.19 Identification of Polymorphisms

The demonstration of such polymorphisms makes possible the identification of such polymorphisms in human subjects and the pharmacogenetic use of this information for diagnosis and treatment. Such polymorphisms may be associated with, e.g., differential predisposition or susceptibility to various disease states (such as disorders involving inflammation or immune response) or a differential response to drug administration, and this genetic information can be used to tailor preventive or therapeutic treatment appropriately. For example, the existence of a polymorphism associated with a predisposition to inflammation or autoimmune disease makes possible the diagnosis of this condition in humans by identifying the presence of the polymorphism.

Polymorphisms can be identified in a variety of ways known in the art which all generally involve obtaining a sample from a patient, analyzing DNA from the sample, optionally involving isolation or amplification of the DNA, and identifying the presence of the polymorphism in the DNA. For example, PCR may be used to amplify an appropriate fragment of genomic DNA which may then be sequenced. Alternatively, the DNA may be subjected to allele-specific oligonucleotide hybridization (in which appropriate oligonucleotides are hybridized to the DNA under conditions permitting detection of a single base mismatch) or to a single nucleotide extension assay (in which an oligonucleotide that hybridizes immediately adjacent to the position of the polymorphism is extended with one or more labeled nucleotides). In addition, traditional restriction fragment length polymorphism analysis (using restriction enzymes that provide differential digestion of the genomic DNA depending on the presence or absence of the polymorphism) may be performed. Arrays with nucleotide sequences of the present invention can be used to detect polymorphisms. The array can comprise modified nucleotide sequences of the present invention in order to detect the nucleotide sequences of the present invention. In the alternative, any one of the nucleotide sequences of the present invention can be placed on the array to detect changes from those sequences.

Alternatively a polymorphism resulting in a change in the amino acid sequence could also be detected by detecting a corresponding change in amino acid sequence of the protein, e.g., by an antibody specific to the variant sequence.

4.7.20 Arthritis and Inflammation

The immunosuppressive effects of the compositions of the invention against rheumatoid arthritis is determined in an experimental animal model system. The experimental model system is adjuvant induced arthritis in rats, and the protocol is described by J. Holoshitz, et at., 1983, Science, 219:56, or by B. Waksman et al., 1963, Int. Arch. Allergy Appl. Immunol., 23:129. Induction of the disease can be caused by a single injection, generally intradermally, of a suspension of killed Mycobacterium tuberculosis in complete Freund's adjuvant (CFA). The route of injection can vary, but rats may be injected at the base of the tail with an adjuvant mixture. The polypeptide is administered in phosphate buffered solution (PBS) at a dose of about 1–5 mg/kg. The control consists of administering PBS only.

The procedure for testing the effects of the test compound would consist of intradermally injecting killed Mycobacterium tuberculosis in CFA followed by immediately administering the test compound and subsequent treatment every other day until day 24. At 14, 15, 18, 20, 22, and 24 days after injection of Mycobacterium CFA, an overall arthritis score may be obtained as described by J. Holoskitz above. An analysis of the data would reveal that the test compound would have a dramatic affect on the swelling of the joints as measured by a decrease of the arthritis score.

4.8 Therapeutic Methods

The compositions (including polypeptide fragments, analogs, variants and antibodies or other binding partners or modulators including antisense polynucleotides) of the invention have numerous applications in a variety of therapeutic methods. Examples of therapeutic applications include, but are not limited to, those exemplified herein.

4.8.1 Example

One embodiment of the invention is the administration of an effective amount of the polypeptides or other composition of the invention to individuals affected by a disease or disorder that can be modulated by regulating the peptides of the invention. While the mode of administration is not particularly important, parenteral administration is preferred. An exemplary mode of administration is to deliver an intravenous bolus. The dosage of the polypeptides or other composition of the invention will normally be determined by the prescribing physician. It is to be expected that the dosage will vary according to the age, weight, condition and response of the individual patient. Typically, the amount of polypeptide administered per dose will be in the range of about 0.0 µg/kg to 100 mg/kg of body weight, with the preferred dose being about 0.1 µg/kg to 10 mg/kg of patient body weight. For parenteral administration, polypeptides of the invention will be formulated in an injectable form combined with a pharmaceutically acceptable parenteral vehicle. Such vehicles are well known in the art and examples include water, saline, Ringer's solution, dextrose solution, and solutions consisting of small amounts of the human serum albumin. The vehicle may contain minor amounts of additives that maintain the isotonicity and stability of the polypeptide or other active ingredient. The preparation of such solutions is within the skill of the art.

4.9 Pharmaceutical Formulations and Routes of Administration

A protein or other composition of the present invention (from whatever source derived, including without limitation from recombinant and non-recombinant sources and including antibodies and other binding partners of the polypeptides of the invention) may be administered to a patient in need, by itself, or in pharmaceutical compositions where it is mixed with suitable carriers or excipient(s) at doses to treat or ameliorate a variety of disorders. Such a composition may optionally contain (in addition to protein or other active ingredient and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IFN, TNF0, TNF1, TNF2, G-CSF, Meg-CSF, thrombopoietin, stem cell factor, and erythropoietin. In further compositions, proteins of the invention may be combined with other agents beneficial to the treatment of the disease or disorder in question. These agents include various growth factors such as epidermal growth factor (EGF), platelet-derived growth factor (PDGF), transforming growth factors (TGF-α and TGF-β), insulin-like growth factor (IGF), as well as cytokines described herein.

The pharmaceutical composition may further contain other agents which either enhance the activity of the protein or other active ingredient or complement its activity or use in treatment. Such additional factors and/or agents may be included in the pharmaceutical composition to produce a synergistic effect with protein or other active ingredient of the invention, or to minimize side effects. Conversely, protein or other active ingredient of the present invention may be included in formulations of the particular clotting factor, cytokine, lymphokine, other hematopoietic factor, thrombolytic or anti-thrombotic factor, or anti-inflammatory agent to minimize side effects of the clotting factor, cytokine, lymphokine, other hematopoietic factor, thrombolytic or anti-thrombotic factor, or anti-inflammatory agent (such as IL-1Ra, IL-1 Hy1, IL-1 Hy2, anti-TNF, corticosteroids, immunosuppressive agents). A protein of the present a invention may be active in multimers (e.g., heterodimers or homodimers) or complexes with itself or other proteins. As a result, pharmaceutical compositions of the invention may comprise a protein of the invention in such multimeric or complexed form.

As an alternative to being included in a pharmaceutical composition of the invention including a first protein, a second protein or a therapeutic agent may be concurrently administered with the first protein (e.g., at the same time, or at differing times provided that therapeutic concentrations of the combination of agents is achieved at the treatment site). Techniques for formulation and administration of the compounds of the instant application may be found in "Remington's Pharmaceutical Sciences," Mack Publishing Co., Easton, Pa., latest edition. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient, administered alone, a therapeutically effective dose refers to that ingredient alone. When applied to a combination, a therapeutically effective dose refers to combined amounts of the active ingredients that result in the therapeutic effect, whether administered in combination, serially or simultaneously.

In practicing the method of treatment or use of the present invention, a therapeutically effective amount of protein or other active ingredient of the present invention is administered to a mammal having a condition to be treated. Protein or other active ingredient of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein or other active ingredient of the present invention may be administered either simultaneously with the cytokine(s), lymphokine(s), other hematopoietic factor (s), thrombolytic or anti-thrombotic factors, or sequentially. If administered sequentially, the attending physician will decide on the appropriate sequence of administering protein or other active ingredient of the present invention in combination with cytokine(s), lymphokine(s), other hematopoietic factor(s), thrombolytic or anti-thrombotic factors.

4.9.1 Routes of Administration

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. Administration of protein or other active ingredient of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous administration to the patient is preferred.

Alternately, one may administer the compound in a local rather than systemic manner, for example, via injection of the compound directly into a arthritic joints or in fibrotic tissue, often in a depot or sustained release formulation. In order to prevent the scarring process frequently occurring as complication of glaucoma surgery, the compounds may be administered topically, for example, as eye drops. Furthermore, one may administer the drug in a targeted drug delivery system, for example, in a liposome coated with a specific antibody, targeting, for example, arthritic or fibrotic tissue. The liposomes will be targeted to and taken up selectively by the afflicted tissue.

The polypeptides of the invention are administered by any route that delivers an effective dosage to the desired site of action. The determination of a suitable route of administration and an effective dosage for a particular indication is within the level of skill in the art. Preferably for wound treatment, one administers the therapeutic compound directly to the site. Suitable dosage ranges for the polypeptides of the invention can be extrapolated from these dosages or from similar studies in appropriate animal models. Dosages can then be adjusted as necessary by the clinician to provide maximal therapeutic benefit.

4.9.2 Compositions/Formulations

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen. When a therapeutically effective amount of protein or other active ingredient of the present invention is administered orally, protein or other active ingredient of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein or other active ingredient of the present invention, and preferably from about 25 to 90% protein or other active ingredient of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein or other active ingredient of the present invention, and preferably from about 1 to 50% protein or other active ingredient of the present invention.

When a therapeutically effective amount of protein or other active ingredient of the present invention is administered by intravenous, cutaneous or subcutaneous injection, protein or other active ingredient of the present invention will be in the form of a pyrogen-free, parenterally acceptable aqueous solution. The preparation of such parenterally acceptable protein or other active ingredient solutions, having due regard to pH, isotonicity, stability, and the like, is within the skill in the art. A preferred pharmaceutical composition for intravenous, cutaneous, or subcutaneous injection should contain, in addition to protein or other active ingredient of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art. For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained from a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. The compounds may be formulated for parenteral administration by injection, e.g., by bolus injection or continuous infusion.

Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a co-solvent system comprising benzyl alcohol, a nonpolar surfactant, a water-miscible organic polymer, and an aqueous phase. The co-solvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose. Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein or other active ingredient stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. Many of the active ingredients of the invention may be provided as salts with pharmaceutically compatible counter ions. Such pharmaceutically acceptable base addition salts are those salts which retain the biological effectiveness and properties of the free acids and which are obtained by reaction with inorganic or organic bases such as sodium hydroxide, magnesium hydroxide, ammonia, trialkylamine, dialkylamine, monoalkylamine, dibasic amino acids, sodium acetate, potassium benzoate, triethanol amine and the like.

The pharmaceutical composition of the invention may be in the form of a complex of the protein(s) or other active ingredient(s) of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunoglobulin and other molecules on B cells as well as antibodies able to bind the TCR and other molecules on T cells can be combined with the pharmaceutical composition of the invention.

The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithins, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

The amount of protein or other active ingredient of the present invention in the pharmaceutical composition of the present invention will depend upon the nature and severity of the condition being treated, and on the nature of prior treatments which the patient has undergone. Ultimately, the attending physician will decide the amount of protein or other active ingredient of the present invention with which to treat each individual patient. Initially, the attending physician will administer low doses of protein or other active ingredient of the present invention and observe the patient's response. Larger doses of protein or other active ingredient of the present invention may be administered until the optimal therapeutic effect is obtained for the patient, and at that point the dosage is not increased further. It is contemplated that the various pharmaceutical compositions used to practice the method of the present invention should contain about 0.01 $\mu$g to about 100 mg (preferably about 0.1 $\mu$g to about 10 mg, more preferably about 0.1 $\mu$g to about 1 mg) of protein or other active ingredient of the present invention per kg body weight. For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a protein or other active ingredient of the invention which may also optionally be included in the composition as described above, may alternatively or additionally, be administered simultaneously or sequentially with the composition in the methods of the invention. Preferably for bone and/or cartilage formation, the composition would include a matrix capable of delivering the protein-containing or other active ingredient-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalcium phosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability. Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein compositions from disassociating from the matrix.

A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorption of the protein from the polymer matrix and to provide appropriate handling of the composition, yet not so much that the progenitor cells are prevented from infiltrating the matrix, thereby providing the protein the opportunity to assist the osteogenic activity of the progenitor cells. In further compositions, proteins or other active ingredients of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-α and TGF-β), and insulin-like growth factor (IGF).

The therapeutic compositions are also presently valuable for veterinary applications. Particularly domestic animals and thoroughbred horses, in addition to humans, are desired patients for such treatment with proteins or other active ingredients of the present invention. The dosage regimen of a protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA). Cells may also be cultured ex vivo in the presence of proteins of the present invention in order to proliferate or to produce a desired effect on or activity in such cells. Treated cells can then be introduced in vivo for therapeutic purposes.

4.9.3 Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amount is well within the capability of those skilled in the art, especially in light of the detailed disclosure provided herein. For any compound used in the method of the invention, the therapeutically effective dose can be estimated initially from appropriate in vitro assays. For example, a dose can be formulated in animal models to achieve a circulating concentration range that can be used to more accurately determine useful doses in humans. For example, a dose can be formulated in animal models to achieve a circulating concentration range that includes the $IC_{50}$ as determined in cell culture (i.e., the concentration of the test compound which achieves a half-maximal inhibition of the protein's biological activity). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. See, e.g., Fingl et al., 1975, in "The Pharmacological Basis of Therapeutics", Ch. 1 p.1. Dosage amount and interval may be adjusted individually to provide plasma levels of the active moiety which are sufficient to maintain the desired effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10–90% of the time, preferably between 30–90% and most preferably between 50–90%. In cases of local administration or selective uptake, the effective local concentration of the drug may not be related to plasma concentration.

An exemplary dosage regimen for polypeptides or other compositions of the invention will be in the range of about 0.01 μg/kg to 100 mg/kg of body weight daily, with the preferred dose being about 0.1 μg/kg to 25 mg/kg of patient body weight daily, varying in adults and children. Dosing may be once daily, or equivalent doses may be delivered at longer or shorter intervals.

The amount of composition administered will, of course, be dependent on the subject being treated, on the subject's age and weight, the severity of the affliction, the manner of administration and the judgment of the prescribing physician.

4.9.4 Packaging

The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

4.10 Antibodies

Another aspect of the invention is an antibody that specifically binds the polypeptide of the invention. Such antibodies include monoclonal and polyclonal antibodies, single chain antibodies, chimeric antibodies, bifunctional/bispecific antibodies, humanized antibodies, human antibodies, and complementary determining region (CDR)-grafted antibodies, including compounds which include CDR and/or antigen-binding sequences, which specifically recognize a polypeptide of the invention. Preferred antibodies of the invention are human antibodies which are produced and identified according to methods described in WO93/11236, published Jun. 20, 1993, which is incorporated herein by reference in its entirety. Antibody fragments, including Fab, Fab', F(ab')$_2$, and F$_v$, are also provided by the invention. The term "specific for" indicates that the variable regions of the antibodies of the invention recognize and bind polypeptides of the invention exclusively (i.e., able to distinguish the polypeptide of the invention from other similar polypeptides despite sequence identity, homology, or similarity found in the family of polypeptides), but may also interact with other proteins (for example, *S. aureus* protein A or other antibodies in ELISA techniques) through interactions with sequences outside the variable region of the antibodies, and in particular, in the constant region of the molecule. Screening assays to determine binding specificity of an antibody of the invention are well known and routinely practiced in the art. For a comprehensive discussion of such assays, see Harlow et al. (Eds), Antibodies A Laboratory Manual; Cold Spring Harbor Laboratory; Cold Spring Harbor, N.Y. (1988), Chapter 6. Antibodies that recognize and bind fragments of the polypeptides of the invention are also contemplated, provided that the antibodies are first and foremost specific for, as defined above, full length polypeptides of the invention. As with antibodies that are specific for full length polypeptides of the invention, antibodies of the invention that recognize fragments are those which can distinguish polypeptides from the same family of polypeptides despite inherent sequence identity, homology, or similarity found in the family of proteins. Antibodies of the invention can be produced using any method well known and routinely practiced in the art.

Non-human antibodies may be humanized by any methods known in the art. In one method, the non-human CDRs are inserted into a human antibody or consensus antibody framework sequence. Further changes can then be introduced into the antibody framework to modulate affinity or immunogenicity.

Antibodies of the invention are useful for, for example, therapeutic purposes (by modulating activity of a polypeptide of the invention), diagnostic purposes to detect or quantitate a polypeptide of the invention, as well as purification of a polypeptide of the invention. Kits comprising an antibody of the invention for any of the purposes described herein are also comprehended. In general, a kit of the invention also includes a control antigen for which the antibody is immunospecific. The invention further provides a hybridoma that produces an antibody according to the invention. Antibodies of the invention are useful for detection and/or purification of the polypeptides of the invention.

Polypeptides of the invention may also be used to immunize animals to obtain polyclonal and monoclonal antibodies which specifically react with the protein. Such antibodies may be obtained using either the entire protein or fragments thereof as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer. Chem. Soc. 85, 2149–2154 (1963); J. L. Krstenansky, et al., FEBS Lett. 211, 10(1987).

Monoclonal antibodies binding to the protein of the invention may be useful diagnostic agents for the immunodetection of the protein. Neutralizing monoclonal antibodies binding to the protein may also be useful therapeutics for both conditions associated with the protein and also in the treatment of some forms of cancer where abnormal expression of the protein is involved. In the case of cancerous cells or leukemic cells, neutralizing monoclonal antibodies against the protein may be useful in detecting and preventing the metastatic spread of the cancerous cells, which may be mediated by the protein. In general, techniques for preparing polyclonal and monoclonal antibodies as well as hybridomas capable of producing the desired antibody are well known in the art (Campbell, A. M., Monoclonal Antibodies Technology: Laboratory Techniques in Biochemistry and Molecular Biology, Elsevier Science Publishers, Amsterdam, The Netherlands (1984); St. Groth et al., J. Immunol. 35:1–21 (1990); Kohler and Milstein, Nature 256:495–497 (1975)), the trioma technique, the human B-cell hybridoma technique (Kozbor et al., Immunology Today 4:72 (1983); Cole et al., in Monoclonal Antibodies and Cancer Therapy, Alan R. Liss, Inc. (1985), pp. 77–96).

Any animal (mouse, rabbit, etc.) which is known to produce antibodies can be immunized with a peptide or polypeptide of the invention. Methods for immunization are well known in the art. Such methods include subcutaneous or intraperitoneal injection of the polypeptide. One skilled in the art will recognize that the amount of the protein encoded by the ORF of the present invention used for immunization will vary based on the animal which is immunized, the antigenicity of the peptide and the site of injection. The protein that is used as an immunogen may be modified or administered in an adjuvant in order to increase the protein's antigenicity. Methods of increasing the antigenicity of a protein are well known in the art and include, but are not limited to, coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, Western blot analysis, or radioimmunoassay (Lutz et al., Exp. Cell Research. 175:109–124 (1988)). Hybridomas secreting the desired antibodies are cloned and the class and subclass is determined using procedures known in the art (Campbell, A. M., Monoclonal Antibody Technology: Laboratory Techniques in Biochemistry and Molecular Biology, Elsevier Science Publishers, Amsterdam, The Netherlands (1984)). Techniques described for the production of single chain antibodies (U.S. Pat. No. 4,946,778) can be adapted to produce single chain antibodies to proteins of the present invention.

For polyclonal antibodies, antibody-containing antiserum is isolated from the immunized animal and is screened for the presence of antibodies with the desired specificity using one of the above-described procedures. The present invention further provides the above- described antibodies in delectably labeled form. Antibodies can be delectably labeled through the use of radioisotopes, affinity labels (such as biotin, avidin, etc.), enzymatic labels (such as horseradish peroxidase, alkaline phosphatase, etc.) fluorescent labels (such as FITC or rhodamine, etc.), paramagnetic atoms, etc. Procedures for accomplishing such labeling are well-known in the art, for example, see (Stemberger, L. A. et al., J. Histochem. Cytochem. 18:315 (1970); Bayer, E. A. et al., Meth. Enzym. 62:308 (1979); Engval, E. et al., Immunol. 109:129 (1972); Goding, J. W. J. Immunol. Meth. 13:215 (1976)).

The labeled antibodies of the present invention can be used for in vitro, in vivo, and in situ assays to identify cells or tissues in which a fragment of the polypeptide of interest is expressed. The antibodies may also be used directly in therapies or other diagnostics. The present invention further provides the above-described antibodies immobilized on a solid support. Examples of such solid supports include plastics such as polycarbonate, complex carbohydrates such as agarose and Sepharose®, acrylic resins and such as polyacrylamide and latex beads. Techniques for coupling antibodies to such solid supports are well known in the art (Weir, D. M. et al., "Handbook of Experimental Immunology" 4th Ed., Blackwell Scientific Publications, Oxford, England, Chapter 10 (1986); Jacoby, W. D. et al., Meth. Enzym. 34 Academic Press, N.Y. (1974)). The immobilized antibodies of the present invention can be used for in vitro, in vivo, and in situ assays as well as for immuno-affinity purification of the proteins of the present invention.

4.11 Computer Readable Sequences

In one application of this embodiment, a nucleotide sequence of the present invention can be recorded on computer readable media. As used herein, "computer readable media" refers to any medium which can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention. As used herein, "recorded" refers to a process for storing information on computer readable medium. A skilled artisan can readily adopt any of the presently known methods for recording information on computer readable medium to generate manufactures comprising the nucleotide sequence information of the present invention.

A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of data processor structuring formats (e.g. text file or database) in order to obtain computer readable medium having recorded thereon the nucleotide sequence information of the present invention.

By providing any of the nucleotide sequences SEQ ID NOs: 1–13 or a representative fragment thereof; or a nucleotide sequence at least 95% identical to any of the nucleotide sequences of SEQ ID NOs: 1–13 in computer readable form, a skilled artisan can routinely access the sequence information for a variety of purposes. Computer software is publicly available which allows a skilled artisan to access sequence information provided in a computer readable medium. The examples which follow demonstrate how software which implements the BLAST (Altschul et al., J. Mol. Biol. 215:403–410 (1990)) and BLAZE (Brutlag et al., Comp. Chem. 17:203–207 (1993)) search algorithms on a Sybase system is used to identify open reading frames (ORFs) within a nucleic acid sequence. Such ORFs may be protein encoding fragments and may be useful in producing commercially important proteins such as enzymes used in fermentation reactions and in the production of commercially useful metabolites.

As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based systems are suitable for use in the present invention. As stated above, the computer-based systems of the present invention comprise a data storage means having stored therein a nucleotide sequence of the present invention and the necessary hardware means and software means for supporting and implementing a search means. As used herein, "data storage means" refers to memory which can store nucleotide sequence information of the present invention, or a memory access means which can access manufactures having recorded thereon the nucleotide sequence information of the present invention.

As used herein, "search means" refers to one or more programs which are implemented on the computer-based system to compare a target sequence or target structural motif with the sequence information stored within the data storage means. Search means are used to identify fragments or regions of a known sequence which match a particular target sequence or target motif. A variety of known algorithms are disclosed publicly and a variety of commercially available software for conducting search means are and can be used in the computer-based systems of the present invention. Examples of such software includes, but is not limited to, Smith-Waterman, MacPattern (EMBL), BLASTN and BLASTA (NPOLYPEPTIDEIA). A skilled artisan can readily recognize that any one of the available algorithms or implementing software packages for conducting homology searches can be adapted for use in the present computer-based systems. As used herein, a "target sequence" can be any nucleic acid or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 300 amino acids, more preferably from about 30 to 100 nucleotide residues. However, it is well recognized that searches for commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

4.12 Triple Helix Formation

In addition, the fragments of the present invention, as broadly described, can be used to control gene expression through triple helix formation or antisense DNA or RNA, both of which methods are based on the binding of a polynucleotide sequence to DNA or RNA. Polynucleotides suitable for use in these methods are preferably 20 to 40 bases in length and are designed to be complementary to a region of the gene involved in transcription (triple helix—see Lee et al., Nucl. Acids Res. 6:3073 (1979); Cooney et al., Science 15241:456 (1988); and Dervan et al., Science 251:1360 (1991)) or to the mRNA itself(antisense—Olmno, J. Neurochem. 56:560 (1991); Oligodeoxynucleotides as Antisense Inhibitors of Gene Expression, CRC Press, Boca Raton, Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide.

4.13 Diagnostic Assays and Kitsi

The present invention further provides methods to identify the presence or expression of one of the ORFs of the present invention, or homolog thereof, in a test sample, using a nucleic acid probe or antibodies of the present invention, optionally conjugated or otherwise associated with a suitable label.

In general, methods for detecting a polynucleotide of the invention can comprise contacting a sample with a compound that binds to and forms a complex with the polynucleotide for a period sufficient to form the complex, and detecting the complex, so that if a complex is detected, a polynucleotide of the invention is detected in the sample. Such methods can also comprise contacting a sample under stringent hybridization conditions with nucleic acid primers that anneal to a polynucleotide of the invention under such conditions, and amplifying annealed polynucleotides, so that if a polynucleotide is amplified, a polynucleotide of the invention is detected in the sample.

In general, methods for detecting a polypeptide of the invention can comprise contacting a sample with a compound that binds to and forms a complex with the polypeptide for a period sufficient to form the complex, and detecting the complex, so that if a complex is detected, a polypeptide of the invention is detected in the sample.

In detail, such methods comprise incubating a test sample with one or more of the antibodies or one or more of the nucleic acid probes of the present invention and assaying for binding of the nucleic acid probes or antibodies to components within the test sample.

Conditions for incubating a nucleic acid probe or antibody with a test sample vary. Incubation conditions depend on the format employed in the assay, the detection methods employed, and the type and nature of the nucleic acid probe or antibody used in the assay. One skilled in the art will recognize that any one of the commonly available hybridization, amplification or immunological assay formats can readily be adapted to employ the nucleic acid probes or antibodies of the present invention. Examples of such assays can be found in Chard, T., An Introduction to Radioimmunoassay and Related Techniques, Elsevier Science Publishers, Amsterdam, The Netherlands (1986); Bullock, G. R. et al., Techniques in Immunocytochemistry, Academic Press, Orlando, Fla. Vol. 1 (1982), Vol. 2 (1983), Vol. 3 (1985); Tijssen, P., Practice and Theory of immunoassays: Laboratory Techniques in Biochemistry and Molecular Biology, Elsevier Science Publishers, Amsterdam, The Netherlands (1985). The test samples of the present invention include cells, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is compatible with the system utilized.

In another embodiment of the present invention, kits are provided which contain the necessary reagents to carry out the assays of the present invention. Specifically, the invention provides a compartment kit to receive, in close confinement, one or more containers which comprises: (a) a first container comprising one of the probes or antibodies of the present invention; and (b) one or more other containers comprising one or more of the following: wash reagents, reagents capable of detecting presence of a bound probe or antibody.

In detail, a compartment kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris-buffers, etc.), and containers which contain the reagents used to detect the bound antibody or probe. Types of detection reagents include labeled nucleic acid probes, labeled secondary antibodies, or in the alternative, if the primary antibody is labeled, the enzymatic, or antibody binding reagents which are capable of reacting with the labeled antibody. One skilled in the art will readily recognize that the disclosed probes and antibodies of the present invention can be readily incorporated into one of the established kit formats which are well known in the art.

4.14 Medical Imaging

The novel polypeptides and binding partners of the invention are useful in medical imaging of sites expressing the molecules of the invention (e.g., where the polypeptide of the invention is involved in the immune response, for imaging sites of inflammation or infection). See, e.g., Kunkel et al., U.S. Pat. No. 5,413,778. Such methods involve chemical attachment of a labeling or imaging agent, administration of the labeled polypeptide to a subject in a pharmaceutically acceptable carrier, and imaging the labeled polypeptide in vivo at the target site.

4.15 Screening Assays

Using the isolated proteins and polynucleotides of the invention, the present invention further provides methods of obtaining and identifying agents which bind to a polypeptide encoded by an ORF corresponding to any of the nucleotide sequences set forth in SEQ ID NOs: 1–13, or bind to a specific domain of the polypeptide encoded by the nucleic acid. In detail, said method comprises the steps of:

(a) contacting an agent with an isolated protein encoded by an ORF of the present invention, or nucleic acid of the invention; and (b) determining whether the agent binds to said protein or said nucleic acid.

In general, therefore, such methods for identifying compounds that bind to a polynucleotide of the invention can comprise contacting a compound with a polynucleotide of the invention for a time sufficient to form a polynucleotide/compound complex, and detecting the complex, so that if a polynucleotide/compound complex is detected, a compound that binds to a polynucleotide of the invention is identified.

Likewise, in general, therefore, such methods for identifying compounds that bind to a polypeptide of the invention can comprise contacting a compound with a polypeptide of the invention for a time sufficient to form a polypeptide/compound complex, and detecting the complex, so that if a polypeptide/compound complex is detected, a compound that binds to a polynucleotide of the invention is identified.

Methods for identifying compounds that bind to a polypeptide of the invention can also comprise contacting a compound with a polypeptide of the invention in a cell for time sufficient to form a polypeptide/compound complex, wherein the complex drives expression of a receptor gene sequence in the cell, and detecting the complex by detecting reporter gene sequence expression, so that if a polypeptide/compound complex is detected, a compound that binds a polypeptide of the invention is identified.

Compounds identified via such methods can include compounds which modulate the activity of a polypeptide of the invention (that is, increase or decrease its activity, relative to activity observed in the absence of the compound). Alternatively, compounds identified via such methods can include compounds which modulate the expression of a polynucleotide of the invention (that is, increase or decrease expression relative to expression levels observed in the absence of the compound). Compounds, such as compounds identified via the methods of the invention, can be tested using standard assays well known to those of skill in the art for their ability to modulate activity/expression.

The agents screened in the above assay can be, but are not limited to, peptides, carbohydrates, vitamin derivatives, or other pharmaceutical agents. The agents can be selected and screened at random or rationally selected or designed using protein modeling techniques.

For random screening, agents such as peptides, carbohydrates, pharmaceutical agents and the like are selected at random and are assayed for their ability to bind to the protein encoded by the ORF of the present invention. Alternatively, agents may be rationally selected or designed. As used herein, an agent is said to be "rationally selected or designed" when the agent is chosen based on the configuration of the particular protein. For example, one skilled in the art can readily adapt currently available procedures to generate peptides, pharmaceutical agents and the like, capable of binding to a specific peptide sequence, in order to generate rationally designed antipeptide peptides, for example see Hurby et al., Application of Synthetic Peptides: Antisense Peptides," In Synthetic Peptides, A User's Guide, W. H. Freeman, NY (1992), pp. 289–307, and Kaspczak et al., Biochemistry 28:9230–8 (1989), or pharmaceutical agents, or the like.

In addition to the foregoing, one class of agents of the present invention, as broadly described, can be used to control gene expression through binding to one of the ORFs or EMFs of the present invention. As described above, such agents can be randomly screened or rationally designed/selected. Targeting the ORF or EMF allows a skilled artisan to design sequence specific or element specific agents, modulating the expression of either a single ORF or multiple ORFs which rely on the same EMF for expression control. One class of DNA binding agents are agents which contain base residues which hybridize or form a triple helix formation by binding to DNA or RNA. Such agents can be based on the classic phosphodiester, ribonucleic acid backbone, or can be a variety of sulfhydryl or polymeric derivatives which have base attachment capacity.

Agents suitable for use in these methods preferably contain 20 to 40 bases and are designed to be complementary to a region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxynucleotides as Antisense Inhibitors of Gene Expression, CRC Press, Boca Raton, Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide and other DNA binding agents.

Agents which bind to a protein encoded by one of the ORFs of the present invention can be used as a diagnostic agent. Agents which bind to a protein encoded by one of the ORFs of the present invention can be formulated using known techniques to generate a pharmaceutical composition.

4.16 Use of Nucleic Acids as Probes

Another aspect of the subject invention is to provide for polypeptide-specific nucleic acid hybridization probes capable of hybridizing with naturally occurring nucleotide sequences. The hybridization probes of the subject invention may be derived from any of the nucleotide sequences SEQ ID NOs: 1–13. Because the corresponding gene is only expressed in a limited number of tissues, a hybridization probe derived from of any of the nucleotide sequences SEQ ID NOs: 1–13 can be used as an indicator of the presence of RNA of cell type of such a tissue in a sample.

Any suitable hybridization technique can be employed, such as, for example, in situ hybridization. PCR as described in US Pat. Nos. 4,683,195 and 4,965,188 provides additional uses for oligonucleotides based upon the nucleotide sequences. Such probes used in PCR may be of recombinant origin, may be chemically synthesized, or a mixture of both. The probe will comprise a discrete nucleotide sequence for the detection of identical sequences or a degenerate pool of possible sequences for identification of closely related genomic sequences.

Other means for producing specific hybridization probes for nucleic acids include the cloning of nucleic acid sequences into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides. The nucleotide sequences may be used to construct hybridization probes for mapping their respective genomic sequences. The nucleotide sequence provided herein may be mapped to a chromosome or specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like. The technique of fluorescent in situ hybridization of chromosome spreads has been described, among other places, in Verma et al (1988) Human Chromosomes: A Manual of Basic Techniques, Pergamon Press, New York N.Y.

Fluorescent in situ hybridization of chromosomal preparations and other physical chromosome mapping techniques may be correlated with additional genetic map data. Examples of genetic map data can be found in the 1994 Genome Issue of Science (265:1981 f). Correlation between the location of a nucleic acid on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

4.17 Preparation of Support Bound Oligonucleotides

Oligonucleotides, i.e., small nucleic acid segments, maybe readily prepared by, for example, directly synthesizing the oligonucleotide by chemical means, as is commonly practiced using an automated oligonucleotide synthesizer.

Support bound oligonucleotides may be prepared by any of the methods known to those of skill in the art using any suitable support such as glass, polystyrene or Teflon. One strategy is to precisely spot oligonucleotides synthesized by standard synthesizers. Immobilization can be achieved using passive adsorption (Inouye & Hondo, (1990) J. Clin. Microbiol. 28(6) 1469–72); using UV light (Nagata et al., 1985; Dahlen et al., 1987; Morrissey & Collins, (1989) Mol. Cell Probes 3(2) 189–207) or by covalent binding of base modified DNA (Keller et al, 1988; 1989); all references being specifically incorporated herein.

Another strategy that may be employed is the use of the strong biotin-streptavidin interaction as a linker. For example, Broude et al (1994) Proc. Natl. Acad. Sci. USA 91(8) 3072–6, describe the use of biotinylated probes, although these are duplex probes, that are immobilized on streptavidin-coated magnetic beads. Streptavidin-coated beads may be purchased from Dynal, Oslo. Of course, this same linking chemistry is applicable to coating any surface with streptavidin. Biotinylated probes may be purchased from various sources, such as, e.g., Operon Technologies (Alameda, Calif.).

Nunc Laboratories (Naperville, Ill.) is also selling suitable material that could be used. Nunc Laboratories have developed a method by which DNA can be covalently bound to the microwell surface termed Covalink NH. CovaLink NH is a polystyrene surface grafted with secondary amino groups (>NH) that serve as bridge-heads for further covalent coupling. CovaLink Modules may be purchased from Nunc Laboratories. DNA molecules may be bound to CovaLink exclusively at the 5'-end by a phosphoramidate bond, allowing immobilization of more than 1 pmol of DNA (Rasmussen et al., (1991) Anal. Biochem. 198(1) 138–42).

The use of CovaLink NH strips for covalent binding of DNA molecules at the 5'-end has been described (Rasmussen et al., (1991). In this technology, a phosphoramidate bond is employed (Chu et al., (1983) Nucleic Acids Res. 11(8) 6513–29). This is beneficial as immobilization using only a single covalent bond is preferred. The phosphoramidate bond joins the DNA to the CovaLink NH secondary amino groups that are positioned at the end of spacer arms covalently grafted onto the polystyrene surface through a 2 nm long spacer arm. To link an oligonucleotide to CovaLink NH via an phosphoramidate bond, the oligonucleotide terminus must have a 5'-end phosphate group. It is, perhaps, even possible for biotin to be covalently bound to CovaLink and then streptavidin used to bind the probes.

More specifically, the linkage method includes dissolving DNA in water (7.5 ng/ul) and denaturing for 10 min. at 95° C. and cooling on ice for 10 min. Ice-cold 0.1 M 1-methylimidazole, pH 7.0 (1-MeIm$_7$), is then added to a final concentration of 10 mM 1-MeIM$_7$. A ss DNA solution is then dispensed into CovaLink NH strips (75 ul/well) standing on ice.

Carbodiimide 0.2 M 1-ethyl-3-(3-dimethylaminopropyl)-carbodiimide (EDC), dissolved in 10 mM 1-MeIm$_7$, is made fresh and 25 ul added per well. The strips are incubated for 5 hours at 50° C. After incubation the strips are washed using, e.g., Nunc-Immuno Wash; first the wells are washed 3 times, then they are soaked with washing solution for 5 min., and finally they are washed 3 times (where in the washing solution is 0.4 N NaOH, 0.25% SDS heated to 50° C.).

It is contemplated that a further suitable method for use with the present invention is that described in PCT Patent Application WO 90/03382 (Southern & Maskos), incorporated herein by reference. This method of preparing an oligonucleotide bound to a support involves attaching a nucleoside 3'-reagent through the phosphate group by a covalent phosphodiester link to aliphatic hydroxyl groups carried by the support. The oligonucleotide is then synthesized on the supported nucleoside and protecting groups removed from the synthetic oligonucleotide chain under standard conditions that do not cleave the oligonucleotide from the support. Suitable reagents include nucleoside phosphoramidite and nucleoside hydrogen phosphorate.

An on-chip strategy for the preparation of DNA probe for the preparation of DNA probe arrays may be employed. For example, addressable laser-activated photodeprotection may be employed in the chemical synthesis of oligonucleotides directly on a glass surface, as described by Fodor et al. (1991) Science 251(4995) 767–73, incorporated herein by reference. Probes may also be immobilized on nylon supports as described by Van Ness et al. (1991) Nucleic Acids Res. 19(12) 3345–50; or linked to Teflon using the method of Duncan & Cavalier (1988) Anal. Biochem. 169(1) 104–8; all references being specifically incorporated herein.

To link an oligonucleotide to a nylon support, as described by Van Ness et al. (1991), requires activation of the nylon surface via alkylation and selective activation of the 5'-amine of oligonucleotides with cyanuric chloride.

One particular way to prepare support bound oligonucleotides is to utilize the light-generated synthesis described by Pease et al., (1994) PNAS USA 91(11) 5022–6, incorporated herein by reference). These authors used current photolithographic techniques to generate arrays of immobilized oligonucleotide probes (DNA chips). These methods, in which light is used to direct the synthesis of oligonucleotide probes in high-density, miniaturized arrays, utilize photolabile 5'-protected N-acyl-deoxynucleoside phosphoramidites, surface linker chemistry and versatile combinatorial synthesis strategies. A matrix of 256 spatially defined oligonucleotide probes may be generated in this manner.

4.18 Preparation of Nucleic Acid Fragments

The nucleic acids may be obtained from any appropriate source, such as cDNAs, genomic DNA, chromosomal DNA, microdissected chromosome bands, cosmid or YAC inserts, and RNA, including mRNA without any amplification steps. For example, Sambrook et al. (1989) describes three protocols for the isolation of high molecular weight DNA from mammalian cells (p. 9.14–9.23).

DNA fragments may be prepared as clones in M13, plasmid or lambda vectors and/or prepared directly from genomic DNA or cDNA by PCR or other amplification methods. Samples may be prepared or dispensed in multiwell plates. About 100–1000 ng of DNA samples may be prepared in 2–500 ml of final volume.

The nucleic acids would then be fragmented by any of the methods known to those of skill in the art including, for example, using restriction enzymes as described at 9.24–9.28 of Sambrook et al. (1989), shearing by ultrasound and NaOH treatment. Low pressure shearing is also appropriate, as described by Schriefer et al. (1990) Nucleic Acids Res. 18(24) 7455–6, incorporated herein by reference). In this method, DNA samples are passed through a small French pressure cell at a variety of low to intermediate pressures. A lever device allows controlled application of low to intermediate pressures to the cell. The results of these studies indicate that low-pressure shearing is a useful alternative to sonic and enzymatic DNA fragmentation methods.

One particularly suitable way for fragmenting DNA is contemplated to be that using the two base recognition endonuclease, CviJI, described by Fitzgerald et al. (1992) Nucleic Acids Res. 20(14) 3753–62. These authors described an approach for the rapid fragmentation and fractionation of DNA into particular sizes that they contemplated to be suitable for shotgun cloning and sequencing.

The restriction endonuclease CviJI normally cleaves the recognition sequence PuGCPy between the G and C to leave blunt ends. Atypical reaction conditions, which alter the specificity of this enzyme (CviJI), yield a quasi-random distribution of DNA fragments form the small molecule pUC19 (2688 base pairs). Fitzgerald et al. (1992) quantitatively evaluated the randomness of this fragmentation strategy, using a CviJI digest of pUC19 that was size fractionated by a rapid gel filtration method and directly ligated, without end repair, to a lac Z minus M13 cloning vector. Sequence analysis of 76 clones showed that CviJI** restricts pyGCPy and PuGCPu, in addition to PuGCPy sites, and that new sequence data is accumulated at a rate consistent with random fragmentation.

As reported in the literature, advantages of this approach compared to sonication and agarose gel fractionation include: smaller amounts of DNA are required (0.2–0.5 ug instead of 2–5 ug); and fewer steps are involved (no preligation, end repair, chemical extraction, or agarose gel electrophoresis and elution are needed.

Irrespective of the manner in which the nucleic acid fragments are obtained or prepared, it is important to denature the DNA to give single stranded pieces available for hybridization. This is achieved by incubating the DNA solution for 2–5 minutes at 80–90° C. The solution is then cooled quickly to 2° C. to prevent renaturation of the DNA fragments before they are contacted with the chip. Phosphate groups must also be removed from genomic DNA by methods known in the art.

4.19 Preparation of Dna Arrays

Arrays may be prepared by spotting DNA samples on a support such as a nylon membrane. Spotting may be performed by using arrays of metal pins (the positions of which correspond to an array of wells in a microtiter plate) to repeated by transfer of about 20 nl of a DNA solution to a nylon membrane. By offset printing, a density of dots higher than the density of the wells is achieved. One to 25 dots may be accommodated in 1 mm$^2$, depending on the type of label used. By avoiding spotting in some preselected number of rows and columns, separate subsets (subarrays) may be formed. Samples in one subarray may be the same genomic segment of DNA (or the same gene) from different individuals, or may be different, overlapped genomic clones. Each of the subarrays may represent replica spotting of the same samples. In one example, a selected gene segment may be amplified from 64 patients. For each patient, the amplified gene segment may be in one 96-well plate (all 96 wells containing the same sample). A plate for each of the 64 patients is prepared. By using a 96-pin device, all samples may be spotted on one 8×12 cm membrane. Subarrays may contain 64 samples, one from each patient. Where the 96 subarrays are identical, the dot span may be 1 mm$^2$ and there may be a 1 mm space between subarrays.

Another approach is to use membranes or plates (available from NUNC, Naperville, Illinois) which may be partitioned by physical spacers e.g. a plastic grid molded over the membrane, the grid being similar to the sort of membrane applied to the bottom of multiwell plates, or hydrophobic strips. A fixed physical spacer is not preferred for imaging by exposure to flat phosphor-storage screens or x-ray films.

The present invention is illustrated in the following examples. Upon consideration of the present disclosure, one of skill in the art will appreciate that many other embodiments and variations may be made in the scope of the present invention. Accordingly, it is intended that the broader aspects of the present invention not be limited to the disclosure of the following examples. The present invention is not to be limited in scope by the exemplified embodiments which are intended as illustrations of single aspects of the invention, and compositions and methods which are functionally equivalent are within the scope of the invention. Indeed, numerous modifications and variations in the practice of the invention are expected to occur to those skilled in the art upon consideration of the present preferred embodiments. Consequently, the only limitations which should be placed upon the scope of the invention are those which appear in the appended claims.

All references cited within the body of the instant specification are hereby incorporated by reference in their entirety.

5.0 EXAMPLES 5.1 Example 1

Novel Nucleic Acid Sequences Obtained from Various Libraries

A plurality of novel nucleic acids were obtained from cDNA libraries prepared from various human tissues and in some cases isolated from a genomic library derived from human chromosome using standard PCR, SBH sequence signature analysis and Sanger sequencing techniques. The inserts of the library were amplified with PCR using primers specific for the vector sequences which flank the inserts. Clones from cDNA libraries were spotted on nylon membrane filters and screened with oligonucleotide probes (e.g., 7-mers) to obtain signature sequences. The clones were clustered into groups of similar or identical sequences. Representative clones were selected for sequencing.

In some cases, the 5' sequence of the amplified inserts was then deduced using a typical Sanger sequencing protocol. PCR products were purified and subjected to fluorescent dye terminator cycle sequencing. Single pass gel sequencing was done using a 377 Applied Biosystems (ABI) sequencer to obtain the novel nucleic acid sequences. In some cases RACE (Random Amplification of cDNA Ends) was performed to further extend the sequence in the 5' direction.

5.2 Example 2

Novel Nucleic Acids

The novel nucleic acids of the present invention of the invention were assembled from sequences that were obtained from a cDNA library by methods described in Example 1 above, and in some cases sequences obtained from one or more public databases. The nucleic acids were assembled using an EST sequence as a seed. Then a recursive algorithm was used to extend the seed EST into an extended assemblage, by pulling additional sequences from different databases (i.e., Hyseq's database containing EST sequences, dbEST version 114, gb pri 114, and UniGene version 101) that belong to this assemblage. The algorithm terminated when there was no additional sequences from the above databases that would extend the assemblage. Inclusion of component sequences into the assemblage was based on a BLASTN hit to the extending assemblage with BLAST score greater than 300 and percent identity greater than 95%.

Using PHRAP (Univ. of Washington) or CAP4 (Paracel), a full length gene cDNA sequence and its corresponding protein sequence were generated from the assemblage. Any frame shifts and incorrect stop codons were corrected by hand editing. During editing, the sequence was checked using FASTY and/or BLAST against Genbank (i.e., dbEST version 118, gb pri 118, UniGene version 118, Genepet release 118). Other computer programs which may have been used in the editing process were phredPhrap and Consed (University of Washington) and ed-ready, ed-ext and gc-zip-2 (Hyseq, Inc.). The full-length nucleotide and amino acid sequences, including splice variants resulting from these procedures are shown in the Sequence Listing as SEQ ID NOS: 1–13.

Table 1 shows the various tissue sources of SEQ ID NO: 1–13.

The homology for SEQ ID NO: 1–13 were obtained by a BLASTP version 2.0al 19MP-WashU search against Genpept release 118, using BLAST algorithm. The results showed homologues for SEQ ID NO: 1–13 from Genpept. The homologues with identifiable functions for SEQ ID NO: 1–13 are shown in Table 2 below.

Using eMatrix software package (Stanford University, Stanford, Calif.) (Wu et al., J. Comp. Biol., Vol. 6 pp. 219–235 (1999) herein incorporated by reference), all the sequences were examined to determine whether they had identifiable signature regions. Table 3 shows the signature region found in the indicated polypeptide sequences, the description of the signature, the eMatrix p-value(s) and the position(s) of the signature within the polypeptide sequence.

Using the pFam software program (Sonnhammer et al., Nucleic Acids Res., Vol. 26(1) pp. 320–322 (1998) herein incorporated by reference) all the polypeptide sequences were examined for domains with homology to certain peptide domains. Table 4 shows the name of the domain found, the description, the p-value and the pFam score for the identified domain within the sequence.

The nucleotide sequence within the sequences that codes for signal peptide sequences and their cleavage sites can be determine from using Neural Network SignalP V1.1 program (from Center for Biological Sequence Analysis, The Technical University of Denmark). The process for identifying prokaryotic and eukaryotic signal peptides and their cleavage sites are also disclosed by Henrik Nielson, Jacob Engelbrecht, Soren Brunak, and Gunnar von Heijne in the publication "Identification of prokaryotic and eukaryotic signal peptides and prediction of their cleavage sites" Protein Engineering, Vol.10, no. 1, pp. 1–6 (1997), incorporated herein by reference. A maximum S score and a mean S score, as described in the Nielson et as reference, was obtained for the polypeptide sequences. Table 5 shows the position of the signal peptide in each of the polypeptides and the maximum score and mean score associated with that signal peptide.

TABLE 1

| TISSUE ORIGIN | RNA SOURCE | HYSEQ LIBRARY NAME | SEQ ID NOS: |
|---|---|---|---|
| adult brain | GIBCO | ABD003 | 2 6–8 |
| adult brain | Clontech | ABR006 | 6–8 |
| adult brain | Clontech | ABR008 | 2 5–8 10 |
| adult brain | Invitrogen | ABT004 | 3 6–8 |
| cultured preadipocytes | Strategene | ADP001 | 10 |
| adrenal gland | Clontech | ADR002 | 1 |
| adult heart | GIBCO | AHR001 | 6–8 10 |
| adult kidney | GIBCO | AKD001 | 2 10 |
| adult kidney | Invitrogen | AKT002 | 10 |
| adult lung | GIBCO | ALG001 | 8 10 |
| young liver | GIBCO | ALV001 | 5 9 11 |
| adult liver | Invitrogen | ALV002 | 2 |
| adult ovary | Invitrogen | AOV001 | 6–9 11 |
| placenta | Invitrogen | APL002 | 10 |
| testis | GIBCO | ATS001 | 10 |
| bone marrow | Clontech | BMD001 | 2 10–11 |
| adult colon | Invitrogen | CLN001 | 3–4 9 |
| adult cervix | BioChain | CVX001 | 2 |
| endothelial cells | Strategene | EDT001 | 9–11 |
| fetal brain | Clontech | FBR004 | 6–8 |
| fetal brain | Clontech | FBR006 | 1 4 10 |
| fetal brain | Invitrogen | FBT002 | 10 |
| fetal heart | Invitrogen | FHR001 | 9 |
| fetal lung | Invitrogen | FLG003 | 6–8 |
| fetal liver-spleen | Columbia University | FLS001 | 2 5 9–11 |
| fetal liver-spleen | Columbia University | FLS002 | 1 9–10 |
| fetal muscle | Invitrogen | FMS001 | 6–8 |
| fetal skin | Invitrogen | FSK001 | 1–2 6–8 |
| fetal skin | Invitrogen | FSK002 | 6–8 |
| fetal brain | GIBCO | HFB001 | 3 6–8 |
| infant brain | Columbia University | IB2002 | 2 6–8 |
| infant brain | Columbia University | IB2003 | 6–8 |
| lung tumor | Invitrogen | LGT002 | 3 6–8 10–11 |
| lymphocytes | ATCC | LPC001 | |
| leukocyte | GIBCO | LUC001 | 3 6–8 10 |
| melanoma from cell line ATCC # CRL 1424 | Clontech | MEL004 | 5–8 |
| mammary gland | Invitrogen | MMG001 | 3–4 6–8 10 |
| neuronal cells | Strategene | NTU001 | 4 13 |
| rectum | Invitrogen | REC001 | 10 |
| spinal cord | Clontech | SPC001 | 10 |
| adult spleen | Clontech | SPLc01 | 6–8 |
| thalamus | Clontech | THA002 | 6–8 |
| thymus | Clontech | THMc02 | 1 |
| thyroid gland | Clontech | THR001 | 1–2 9 |
| trachea | Clontech | TRC001 | 6–8 |

TABLE 2

| SEQ ID NO: | CORRESPONDING SEQ ID NO. IN U.S.S.N. 09/649,167 | ACCESSION NUMBER | DESCRIPTION | SMITH-WATERMAN SCORE | % IDENTITY |
|---|---|---|---|---|---|
| 1 | 1884 | Z14016 | *Nicotiana tabacum* pistil extensin like protein, partial CDS | 103 | 37 |
| 2 | 5410 22854 22855 22856 | D11466 | *Homo sapiens* PIG-A protein | 2519 | 100 |
| 3 | 11528 | AC002505 | *Arabidopsis thaliana* putative cyclin | 240 | 30 |
| 4 | 14360 14361 14362 | AF159297 | *Zea mays* extensin-like protein | 148 | 24 |
| 5 | 16899 16900 16901 | AC002988 | *Homo sapiens* OLF4 | 381 | 62 |
| 6 | 21007 21008 21009 21010 | AF124490 | *Homo sapiens* ARF GTPase-activating protein GIT1 | 3912 | 99 |
| 7 | 21007 21008 21009 21010 | AF124490 | *Homo sapiens* ARF GTPase-activating protein GIT1 | 3887 | 98 |
| 8 | 21007 21008 21009 21010 | AF124490 | *Homo sapiens* ARF GTPase-activating protein GIT1 | 2567 | 99 |
| 9 | 26173 26174 26175 26176 26177 26178 | Y10529 | *Homo sapiens* olfactory receptor | 969 | 71 |
| 10 | 27023 27024 27025 | AF127837 | *Hylobates lar* olfactory receptor | 1082 | 95 |
| 11 | 27169 27170 27171 27172 27173 27174 | Y10529 | *Homo sapiens* olfactory receptor | 1393 | 100 |
| 12 | 28495 | AF044601 | *Homo sapiens* orphan G protein-coupled receptor; GPC-R | 2113 | 99 |
| 13 | 28544 | AF121976 | *Mus musculus* odorant receptor S19 | 1017 | 58 |

TABLE 3

| SEQ ID NO: | ACCESSION NO. | DESCRIPTION | RESULTS* |
|---|---|---|---|
| 1 | DM01803 | 1 HERPESVIRUS GLYCOPROTEIN H. | DM01803C 7.00 8.800e-07 219–229 |
| 2 | PF00534 | Glycosyl transferases group 1. | PF00534B 14.47 6.182e-15 312–336 |
| 3 | PD02331 | CYCLIN CELL CYCLE DIVISION PROTE. | PD02331C 13.84 3.192e-09 128–155 |
| 4 | PR00513 | 5-HYDROXYTRYPTAMINE 1B RECEPTOR SIGNATURE | PR00513C 10.79 4.814e-06 5–22 |
| 5 | PR00237 | RHODOPSIN-LIKE GPCR SUPERFAMILY SIGNATURE | PR00237A 11.48 2.742e-09 107–132<br>PR00237B 13.50 3.500e-09 140–162 |
| 6 | PF00023 | Ank repeat proteins. | PF00023B 14.20 5.091e-09 188–198 |
| 7 | PF00023 | Ank repeat proteins. | PF00023B 14.20 5.091e-09 188–198<br>PF00023B 14.20 5.091e-09 970–980 |
| 8 | PF00023 | Ank repeat proteins. | PF00023B 14.20 5.091e-09 188–198<br>PF00023B 14.20 5.091e-09 970–980 |
| 10 | PR00237 | RHODOPSIN-LIKE GPCR SUPERFAMILY SIGNATURE | PR00237E 13.03 2.200e-10 240–264<br>PR00237B 13.50 9.500e-09 100–122<br>PR00237C 15.69 1.000e-08 145–168 |
| 11 | BL00237 | G-protein coupled receptors proteins. | BL00237A 27.68 6.143e-13 57–97<br>BL00237D 11.23 5.091e-09 249–266 |
| 12 | BL00237 | G-protein coupled receptors proteins. | BL00237A 27.68 3.250e-19 146–186<br>BL00237C 13.19 4.240e-14 309–336<br>BL00237B 5.28 1.000e-09 259–271<br>BL00237D 11.23 5.636e-09 367–384 |
| 13 | PR00237 | RHODOPSIN-LIKE GPCR SUPERFAMILY SIGNATURE | PR00237A 11.48 1.000e-08 180–205 |

*Results include in order: accession number subtype; raw score; p-value; position of signature in amino acid sequence.

TABLE 4

| SEQ ID NO: | pFAM NAME | DESCRIPTION | p-value | pFAM SCORE |
|---|---|---|---|---|
| 2 | Glycos_transf_1 | Glycosyl transferases group 1 | 3.9e-15 | 56.9 |
| 5 | 7tm_1 | 7 transmembrane receptor (rhodopsin family) | 3.4e-19 | 63.1 |
| 6 | ank | Ank repeat | 4.7e-06 | 33.6 |
| 7 | ank | Ank repeat | 4.7e-06 | 33.6 |
| 10 | 7tm_1 | 7 transmembrane receptor (rhodopsin family) | 2.3e-45 | 146.2 |
| 11 | 7tm_1 | 7 transmembrane receptor (rhodopsin family) | 1.8e-41 | 133.9 |
| 12 | 7tm_1 | 7 transmembrane receptor (rhodopsin family) | 9.2e-63 | 201.5 |
| 13 | 7tm_1 | 7 transmembrane receptor (rhodopsin family) | 1.5e-16 | 54.8 |

TABLE 5

| SEQ ID NO: | POSITION OF SIGNAL IN AMINO ACID SEQUENCE | maxS (MAXIMUM SCORE) | meanS (MEAN SCORE) |
|---|---|---|---|
| 9 | 1-18 | 0.958 | 0.889 |
| 11 | 1-22 | 0.966 | 0.767 |

What is claimed is:

1. An isolated polynucleotide comprising the nucleotide sequence of SEQ ID NO: 12.
2. A vector comprising the polynucleotide of claim 1.
3. An expression vector comprising the polynucleotide of claim 1.
4. A host cell genetically engineered to comprise the polynucleotide of claim 1.
5. A host cell genetically engineered to comprise the polynucleotide of claim 1 operatively associated with a regulatory sequence that modulates expression of the polynucleotide in the host cell.

* * * * *

```
                        SEQUENCE LISTING

<160> NUMBER OF SEQ ID NOS: 13

<210> SEQ ID NO 1
<211> LENGTH: 3134
<212> TYPE: DNA
<213> ORGANISM: Homo sapiens
<220> FEATURE:
<221> NAME/KEY: CDS
<222> LOCATION: (189)..(1742)

<400> SEQUENCE: 1
aatgtcgacg atttcgtgcc ggggattcgc cggcccacgc caggccccgg gcggagaatg      60
aaaggacaat ctgcttcatc ctgattctgc ggcattccaa actgtggtat ccttgggggt     120
tctcttaaca ttgctatggt gcagaagatt taaaatcagc tgatgttcac aaggaataca     180 gtcacgtg atg tat gaa ggg aaa cat ata cac ttc tct gag gtt gac aat      230
         Met Tyr Glu Gly Lys His Ile His Phe Ser Glu Val Asp Asn
           1               5                  10 aag ccc ttg tgc tca tat agc ccc aaa ctg tgc aag cag agg cga ctc      278
Lys Pro Leu Cys Ser Tyr Ser Pro Lys Leu Cys Lys Gln Arg Arg Leu
 15                  20                  25                  30 aac ggc tac gcc ttc tgt atc aga cac gtt ctg gag gac aag act gcc      326
Asn Gly Tyr Ala Phe Cys Ile Arg His Val Leu Glu Asp Lys Thr Ala
                 35                  40                  45 ccc ttc aag caa tgt gaa tat gtg gcc aag tat aac agc caa cgc tgc      374
Pro Phe Lys Gln Cys Glu Tyr Val Ala Lys Tyr Asn Ser Gln Arg Cys
             50                  55                  60 acc aac ccc atc ccc aaa tca gag gat cgt agg tac tgc aac agc cac      422
Thr Asn Pro Ile Pro Lys Ser Glu Asp Arg Arg Tyr Cys Asn Ser His
         65                  70                  75 ttg cag gta ctt ggc ttt atc ccg aaa aaa gag agg aag aaa aag aat      470
Leu Gln Val Leu Gly Phe Ile Pro Lys Lys Glu Arg Lys Lys Lys Asn
     80                  85                  90
```

| | | |
|---|---|---|
| gat cct ata gat gag gtg aag gtc agg cac cag atg gat acc atg gcc<br>Asp Pro Ile Asp Glu Val Lys Val Arg His Gln Met Asp Thr Met Ala<br>95                    100                    105                  110 | 518 |

```
gat cct ata gat gag gtg aag gtc agg cac cag atg gat acc atg gcc     518
Asp Pro Ile Asp Glu Val Lys Val Arg His Gln Met Asp Thr Met Ala
 95                 100                 105                 110 ttt agc ctg aca gtg ccc acg ttg gcc ttg aag atg ccc aac gga ctg     566
Phe Ser Leu Thr Val Pro Thr Leu Ala Leu Lys Met Pro Asn Gly Leu
                115                 120                 125 gat gga atg tcc ctc tct cca cct ggg gca agg gtc cct ctc cac tac     614
Asp Gly Met Ser Leu Ser Pro Pro Gly Ala Arg Val Pro Leu His Tyr
    130                 135                 140 ctg gaa act gaa ttg gaa gac cca ttt gct ttc aat gag gaa gat gat     662
Leu Glu Thr Glu Leu Glu Asp Pro Phe Ala Phe Asn Glu Glu Asp Asp
145                 150                 155 gac cta aag aaa ggg gca act gtg aga aag aag ttg cag agc aag ttg     710
Asp Leu Lys Lys Gly Ala Thr Val Arg Lys Lys Leu Gln Ser Lys Leu
    160                 165                 170 gcc cag aat cgg cag cgc cag aga gag aca gag att tta aaa gtt cga     758
Ala Gln Asn Arg Gln Arg Gln Arg Glu Thr Glu Ile Leu Lys Val Arg
175                 180                 185                 190 caa gag cac ttt agt ccc cct cct gca cct tca cag cag cag cct ccg     806
Gln Glu His Phe Ser Pro Pro Pro Ala Pro Ser Gln Gln Gln Pro Pro
                195                 200                 205 cag cag cac tcc cac ctg tca cct tta tct act tct tta aaa cct cca     854
Gln Gln His Ser His Leu Ser Pro Leu Ser Thr Ser Leu Lys Pro Pro
        210                 215                 220 gcg cca ccg cag ggt tca gtc tgc aag tca cct caa cct cag aac acc     902
Ala Pro Pro Gln Gly Ser Val Cys Lys Ser Pro Gln Pro Gln Asn Thr
225                 230                 235 agc cta cca atg cag ggg gtg gca ccc acc aca cac act ata gca caa     950
Ser Leu Pro Met Gln Gly Val Ala Pro Thr Thr His Thr Ile Ala Gln
    240                 245                 250 gca cgg cag ttg tct cac aag agg cct ctg ccc ctc ctg cca tcc agt     998
Ala Arg Gln Leu Ser His Lys Arg Pro Leu Pro Leu Leu Pro Ser Ser
255                 260                 265                 270 agg gct ccc act gtg gac cca ccc agg act gac cgg atc ctc atg aaa    1046
Arg Ala Pro Thr Val Asp Pro Pro Arg Thr Asp Arg Ile Leu Met Lys
                275                 280                 285 gcc aca gcc ttc tct cca cac ttc tca tgt ata agc cga ctg cag aga    1094
Ala Thr Ala Phe Ser Pro His Phe Ser Cys Ile Ser Arg Leu Gln Arg
        290                 295                 300 ctg gtg aaa ctg tgc acc cag aaa cat cag ttg gac act gat ctg ttt    1142
Leu Val Lys Leu Cys Thr Gln Lys His Gln Leu Asp Thr Asp Leu Phe
            305                 310                 315 ccc cat tta ggt ttg gac tgg tct gaa gag agc gga gag gaa cca gag    1190
Pro His Leu Gly Leu Asp Trp Ser Glu Glu Ser Gly Glu Glu Pro Glu
320                 325                 330 gac tca gag cag gcc tcg ccc tac cag gtt gca tgg tcc atc cgg gaa    1238
Asp Ser Glu Gln Ala Ser Pro Tyr Gln Val Ala Trp Ser Ile Arg Glu
335                 340                 345                 350 acc ctc aga tat caa aga cat gtg tca gat gat gat gat gcg gag agt    1286
Thr Leu Arg Tyr Gln Arg His Val Ser Asp Asp Asp Asp Ala Glu Ser
                355                 360                 365 agg agc tcc agg gtg act caa ctt tgc act tac ttt cag cag aaa tat    1334
Arg Ser Ser Arg Val Thr Gln Leu Cys Thr Tyr Phe Gln Gln Lys Tyr
        370                 375                 380 aag cac ctc tgc cgc ctg gag cgg gca gaa tct cgt caa aag aaa tgc    1382
Lys His Leu Cys Arg Leu Glu Arg Ala Glu Ser Arg Gln Lys Lys Cys
            385                 390                 395 cgg cat acg ttt agg aaa gct ttg ctg cag gcg gcc agt aaa gaa cca    1430
Arg His Thr Phe Arg Lys Ala Leu Leu Gln Ala Ala Ser Lys Glu Pro
400                 405                 410
```

```
gaa tgc act ggt cag tta ata caa gaa ctg cgg aga gct gca tgc agt    1478
Glu Cys Thr Gly Gln Leu Ile Gln Glu Leu Arg Arg Ala Ala Cys Ser
415                 420                 425                 430 cga acc agc ata agc cgg acc aag ctg agg gag gtg gaa cca gca gca    1526
Arg Thr Ser Ile Ser Arg Thr Lys Leu Arg Glu Val Glu Pro Ala Ala
                435                 440                 445 tgc agt gga acc gtg aag ggt gaa cag tgc gct aac aaa gcc ctt cca    1574
Cys Ser Gly Thr Val Lys Gly Glu Gln Cys Ala Asn Lys Ala Leu Pro
            450                 455                 460 ttc acc aga cat tgt ttc caa cat atc ctc ttg aac cac tct cag cag    1622
Phe Thr Arg His Cys Phe Gln His Ile Leu Leu Asn His Ser Gln Gln
        465                 470                 475 ctc ttc tca agt tgc aca gcc aag ttt gca gat gga cag cag tgc tct    1670
Leu Phe Ser Ser Cys Thr Ala Lys Phe Ala Asp Gly Gln Gln Cys Ser
    480                 485                 490 gtg cca gtt ttt gac att aca cat cag aca cct ctg tgt gaa gaa cat    1718
Val Pro Val Phe Asp Ile Thr His Gln Thr Pro Leu Cys Glu Glu His
495                 500                 505                 510 gcc aaa aaa tgg ata att cct tga gaggagataa ctcccgtaaa gttcagcacc   1772
Ala Lys Lys Trp Ile Ile Pro  *
                515 agcagcagag gaaacccagg aaaaaaacca agcctcctgc actaaccaaa aaacacaaga   1832 agaagagaag gcgtggacct cgtcgacccc aaaaacccat tccacctgca gtcccccaag   1892 ggaacctcag catgcccgcc agcgtctcac tgccagtgga ggcctctcac atccggagcc   1952 catccacgcc agagctgagt gctgatgagt tgccggatga cattgccaat gagatcactg   2012 acattccaca tgacttggaa ttgaaccagg aggacttttc agatgtcctg ccacggctac   2072 ctgatgactt acaagatttt gatttttttg aagggaagaa tggagacctc ctcccaacta   2132 ccgaagaggc tgaggagctt gaacgggcct gcaggctgt aacttctctc gagtgcctga    2192 gtaccattgg ggtccttgcc cagtcagatg gtgtgccagt ccaggagttg tcagatagag   2252 gaatagggg tgttctccaca ggtactggag cttcaggaat acaatccttg agccgagagg    2312 tgaacacaga cctaggggag ctattgaatg gcgtatagt acatgataat ttttctagtc     2372 tagagctgga tgagaacctg ctccgttctg ctaccttgtc aaacccacct acaccctgg     2432 cagggcagat ccaggggcag ttctctgccc cagccaacgt tggccttact tctgccactc    2492 tgatcagcca gagtgcactt ggggagagag ccttcccagg acagtttcat ggacttcatg    2552 acggcagcca tgcctcccag aggccacatc ctgcccagct gctgagcaag gcagatgacc    2612 taatcacctc acgacagcaa tacagcagtg atcactcaca ctcctcaccc catggaagcc    2672 attatgatag tgagcatgtg ccgtctccct acagtgacca tatcacctct ccccacacaa    2732 catcgtactc tggtgataat atggcagcta cctttcagc agagatgccc atcatggcgc     2792 agcacttgct cccaacccaa cttgaggtgc acttggagg cgtggtaaac cccagaactc     2852 actggggcaa tctccctgtc aaccttggag acccctctcc atttagcaac cttctcggcg    2912 cagatggaca tcttctttcc acttcccttat ccacgccacc caccacttcg aactcagaga    2972 ccacacagcc tgccttcgcc accgtgaccc ccagcagctc cagtgtgctt ccggggttac    3032 cacagaccag cttcagtggc atggggcctt ctgctgaact aatggcctcc acctctattg    3092 cggccgctct agaggatcca agcttacgta cgcgtgcatg cg                       3134
```

<210> SEQ ID NO 2
<211> LENGTH: 3601
<212> TYPE: DNA

-continued

```
<213> ORGANISM: Homo sapiens
<220> FEATURE:
<221> NAME/KEY: CDS
<222> LOCATION: (86)..(1540)

<400> SEQUENCE: 2
actggcggcc atggaactca ccggtaatag aggacacatc tcttaactgg gttgctctaa      60
gaactgatgt ctaaaccgtc tcagc atg gcc tgt aga gga gga gct ggg aat      112
                             Met Ala Cys Arg Gly Gly Ala Gly Asn
                               1               5 ggc cac cgt gcc tca gct aca ctc tct cgg gtt agc cct gga agt ctt      160
Gly His Arg Ala Ser Ala Thr Leu Ser Arg Val Ser Pro Gly Ser Leu
 10              15                  20                  25 tac aca tgt aga acc cgt acc cat aat ata tgc atg gta tct gac ttt      208
Tyr Thr Cys Arg Thr Arg Thr His Asn Ile Cys Met Val Ser Asp Phe
                 30                  35                  40 ttc tac cca aat atg gga ggc gtg gaa agc cac att tac cag ctc tct      256
Phe Tyr Pro Asn Met Gly Gly Val Glu Ser His Ile Tyr Gln Leu Ser
             45                  50                  55 cag tgc ctg att gaa aga ggg cat aag gtt ata att gtc acc cat gct      304
Gln Cys Leu Ile Glu Arg Gly His Lys Val Ile Ile Val Thr His Ala
         60                  65                  70 tat gga aat cga aaa ggc atc cgt tac ctc acc agt ggc ctc aaa gtc      352
Tyr Gly Asn Arg Lys Gly Ile Arg Tyr Leu Thr Ser Gly Leu Lys Val
     75                  80                  85 tat tac ttg cct ctg aaa gtc atg tac aac cag tct aca gcc acg acc      400
Tyr Tyr Leu Pro Leu Lys Val Met Tyr Asn Gln Ser Thr Ala Thr Thr
 90                  95                 100                 105 ctc ttt cac agt ctg cca ttg ctc agg tac ata ttt gtt cgg gag aga      448
Leu Phe His Ser Leu Pro Leu Leu Arg Tyr Ile Phe Val Arg Glu Arg
                110                 115                 120 gtc acg ata atc cat tca cat agt tct ttt tct gct atg gcc cat gat      496
Val Thr Ile Ile His Ser His Ser Ser Phe Ser Ala Met Ala His Asp
            125                 130                 135 gct ctc ttc cac gcc aag aca atg ggg ctt cag aca gtc ttc acg gac      544
Ala Leu Phe His Ala Lys Thr Met Gly Leu Gln Thr Val Phe Thr Asp
        140                 145                 150 cat tcc ctt ttt gga ttt gct gat gtc agc tcg gtg ctt aca aac aag      592
His Ser Leu Phe Gly Phe Ala Asp Val Ser Ser Val Leu Thr Asn Lys
    155                 160                 165 ctt cta acc gtg tct ctt tgt gat aca aac cac atc att tgt gtg tct      640
Leu Leu Thr Val Ser Leu Cys Asp Thr Asn His Ile Ile Cys Val Ser
170                 175                 180                 185 tat act agt aag gaa aat act gta cta aga gca gca ctg aat cct gaa      688
Tyr Thr Ser Lys Glu Asn Thr Val Leu Arg Ala Ala Leu Asn Pro Glu
                190                 195                 200 ata gtg tcc gtc att cct aat gct gta gat cct act gac ttc act cca      736
Ile Val Ser Val Ile Pro Asn Ala Val Asp Pro Thr Asp Phe Thr Pro
            205                 210                 215 gac cca ttt aga agg cat gat agt ata act att gtt gtt gtc agc aga      784
Asp Pro Phe Arg Arg His Asp Ser Ile Thr Ile Val Val Val Ser Arg
        220                 225                 230 ctt gtt tac aga aaa ggg atc gat ttg ctt agt ggt ata ata cct gaa      832
Leu Val Tyr Arg Lys Gly Ile Asp Leu Leu Ser Gly Ile Ile Pro Glu
    235                 240                 245 ctc tgt cag aaa tat cca gat tta aat ttc ata att gga gga gag gga      880
Leu Cys Gln Lys Tyr Pro Asp Leu Asn Phe Ile Ile Gly Gly Glu Gly
250                 255                 260                 265 cca aag aga atc att ttg gaa gaa gtt cgg gaa aga tac cag ctg cat      928
Pro Lys Arg Ile Ile Leu Glu Glu Val Arg Glu Arg Tyr Gln Leu His
```

-continued

|  | 270 | | | | 275 | | | | 280 | | | | | | |
|---|---|---|---|---|---|---|---|---|---|---|---|---|---|---|---|
| gac | agg | gtg | cgt | ctt | ttg | gga | gct | tta | gaa | cac | aag | gat | gtt | aga | aat | 976 |
| Asp | Arg | Val | Arg | Leu | Leu | Gly | Ala | Leu | Glu | His | Lys | Asp | Val | Arg | Asn |
|  |  |  | 285 |  |  |  |  | 290 |  |  |  |  | 295 |  |  |

| gtc | tta | gtt | caa | gga | cat | att | ttt | ctg | aat | acc | tcc | ctt | act | gaa | gca | 1024 |
| Val | Leu | Val | Gln | Gly | His | Ile | Phe | Leu | Asn | Thr | Ser | Leu | Thr | Glu | Ala |
|  |  |  | 300 |  |  |  |  | 305 |  |  |  |  | 310 |  |  |

| ttc | tgc | atg | gcg | atc | gtg | gaa | gca | gcc | agt | tgt | ggt | tta | cag | gtt | gta | 1072 |
| Phe | Cys | Met | Ala | Ile | Val | Glu | Ala | Ala | Ser | Cys | Gly | Leu | Gln | Val | Val |
|  |  |  | 315 |  |  |  |  | 320 |  |  |  |  | 325 |  |  |

| agt | acc | aga | gtt | ggt | gga | att | cct | gag | gtg | ctt | cca | gaa | aac | ctt | att | 1120 |
| Ser | Thr | Arg | Val | Gly | Gly | Ile | Pro | Glu | Val | Leu | Pro | Glu | Asn | Leu | Ile |
| 330 |  |  |  |  | 335 |  |  |  |  | 340 |  |  |  |  | 345 |

| att | tta | tgt | gag | cct | tca | gta | aaa | tct | ttg | tgt | gaa | gga | ttg | gaa | aag | 1168 |
| Ile | Leu | Cys | Glu | Pro | Ser | Val | Lys | Ser | Leu | Cys | Glu | Gly | Leu | Glu | Lys |
|  |  |  |  | 350 |  |  |  |  | 355 |  |  |  |  | 360 |  |

| gct | att | ttc | caa | ctg | aag | tca | ggg | aca | ttg | cca | gct | cca | gaa | aac | atc | 1216 |
| Ala | Ile | Phe | Gln | Leu | Lys | Ser | Gly | Thr | Leu | Pro | Ala | Pro | Glu | Asn | Ile |
|  |  |  |  | 365 |  |  |  |  | 370 |  |  |  |  | 375 |  |

| cat | aac | ata | gta | aag | act | ttc | tac | acc | tgg | agg | aat | gtt | gca | gaa | aga | 1264 |
| His | Asn | Ile | Val | Lys | Thr | Phe | Tyr | Thr | Trp | Arg | Asn | Val | Ala | Glu | Arg |
|  |  |  | 380 |  |  |  |  | 385 |  |  |  |  | 390 |  |  |

| act | gaa | aag | gta | tat | gac | cgg | gta | tca | gtg | gaa | gct | gtg | ttg | cca | atg | 1312 |
| Thr | Glu | Lys | Val | Tyr | Asp | Arg | Val | Ser | Val | Glu | Ala | Val | Leu | Pro | Met |
|  | 395 |  |  |  |  | 400 |  |  |  |  | 405 |  |  |  |  |

| gac | aaa | cga | ctg | gac | aga | ctt | att | tct | cac | tgc | ggc | cca | gta | aca | ggc | 1360 |
| Asp | Lys | Arg | Leu | Asp | Arg | Leu | Ile | Ser | His | Cys | Gly | Pro | Val | Thr | Gly |
| 410 |  |  |  |  | 415 |  |  |  |  | 420 |  |  |  |  | 425 |

| tac | atc | ttt | gct | ttg | ttg | gca | gtt | ttc | aac | ttc | ctc | ttc | ctc | att | ttc | 1408 |
| Tyr | Ile | Phe | Ala | Leu | Leu | Ala | Val | Phe | Asn | Phe | Leu | Phe | Leu | Ile | Phe |
|  |  |  |  | 430 |  |  |  |  | 435 |  |  |  |  | 440 |  |

| ttg | aga | tgg | atg | act | cca | gat | tct | atc | att | gat | gtt | gca | ata | gat | gcc | 1456 |
| Leu | Arg | Trp | Met | Thr | Pro | Asp | Ser | Ile | Ile | Asp | Val | Ala | Ile | Asp | Ala |
|  |  |  | 445 |  |  |  |  | 450 |  |  |  |  | 455 |  |  |

| act | ggg | cca | cgg | ggt | gcc | tgg | act | aat | aac | tat | tct | cac | agt | aaa | aga | 1504 |
| Thr | Gly | Pro | Arg | Gly | Ala | Trp | Thr | Asn | Asn | Tyr | Ser | His | Ser | Lys | Arg |
|  |  |  | 460 |  |  |  |  | 465 |  |  |  |  | 470 |  |  |

| ggg | ggt | gag | aat | aat | gag | ata | tct | gaa | acc | agg | tag | aagg | aagcctagat | 1554 |
| Gly | Gly | Glu | Asn | Asn | Glu | Ile | Ser | Glu | Thr | Arg | * |
|  | 475 |  |  |  |  | 480 |  |  |  |  | 485 |

| tgtaagattt | taaacatttg | taatagttct | ataaagacta | tggaaaataa | ccttgctttt | 1614 |
| gggggttttt | tgttttttta | gagttaattt | agtaagttat | gctacctcta | tatcattcaa | 1674 |
| tattttctgt | tgaggaaaga | taaaaatgta | tgcaattcct | gagtgtagaa | acttcttgca | 1734 |
| cttatttaaa | atttaggaga | gaacatttaa | gccactcagg | tatgcaattt | ttcagactac | 1794 |
| tgaaatccct | gtagcagaga | tgttttaaca | ttatattttg | agagctttgg | gtgctgaagg | 1854 |
| gccaaacgtt | ttctgggcat | tttttggcca | gtttttaatg | taacaccatt | agacactcac | 1914 |
| cagatgttta | caagttttct | ttaggggaac | tacaacaatt | atatgaactg | ttttatatca | 1974 |
| tgttcatata | catttattag | gaatctaaat | catgtctttg | aacatttatt | aggttcactc | 2034 |
| agtaggtgtt | acatgtaatt | aacaggttcc | ttgagtaaga | tagtccatca | gttaccagca | 2094 |
| cattttgaac | ccctgctctg | tgtagaatgt | tgaactagat | gcttcccgcc | attaaggacc | 2154 |
| agggggtgcat | tcactctttg | tttaccattc | aaatggctta | cttcatcata | attgtggttg | 2214 |
| atatgagatc | aaatatccaac | atgccaaaaa | tgctcatgcc | agttaatgcc | aggaaaaaaa | 2274 |
| tcaccgacac | actactagta | ctttgttcct | gttgtatgca | ttctcctagg | tagagcctcc | 2334 |

```
atcttcagtt gtgtttgtga aggtatttttt tgcttttttaa atactggggga ccgatatcac    2394 tgttgatagt gcagagaaac cctccacatt tttcagtgca taattgagtt ttctataaat    2454
gccttcgtgt tttctgagca gaatgtacga ggtgtgccat cccaaaacca gctgctaccc    2514 tgtccttttta atgtaagtca ctccccttca ctgtggcctc gctgatgtct gataagtatt    2574
gtcagtgtgc aaaaggcttt acttcagaat ggtttattta tagcaaacta agttgaaaat    2634
tttagaaaca gtctttgtgg gtggatgtta ttaactgtca ttgttgttgc ccagagccat    2694 gggttttta accccaaatt atccacatgg tgtgtattat gaattctttg aactcttaag    2754
gtttttgtga gaaaggact gtgaattcaa acaataagg cacttgtggg tgcactacat    2814
agattctgac agtgttgtga ttctgtatag gattttttaaa aatgacaaca ttcacaaaat    2874
ttattacttt ttaaaaaata acatgcctat taactggttg cactgatata aaagaaatat    2934
atttgtgttt tgtttgtact aaaatgcaaa agcaagagtg caattttttaa aatctagaag    2994 ttagggggttt tgttggagaa aaatggactg atctttaaac tattcagtct tactgggatt    3054
tttatgcata gaaactcaca tataaacatg aaataaacag tgccagtatt cataggaaag    3114
tgagaaactg taatatttgg ccattattct attcaacagg ttttagaggc acgccaccat    3174 ttttttccctta tattttttgct taatttttttt aaattgtcat ttaattctta aactgtcatt    3234
tatttgagat ggaaataaga tctaaagtta gttgcctttg cctgtaaaac atgtgatttg    3294
caaattatta ttttcctttt tttttaacaa atggaagtaa atttgtttca cgtaaatctt    3354
aattttcaac ctttctggat accttaattg taactgtcag tttgcactgg tcggtatatg    3414
gaaacacatt gctctacccct gctacttagt tgattttaa gtgaatttac agtgatgaga    3474 aattttgtgaa aaatatattg tatttcttttt gatgtttcaa aaggttgcct atgaaaaact    3534 gattttgttaa acatgctac atgtccaaaa ataaagacca gaatgacatt ttgataaaaaa    3594 aaaaaaa                                                              3601
```

<210> SEQ ID NO 3
<211> LENGTH: 1357
<212> TYPE: DNA
<213> ORGANISM: Homo sapiens
<220> FEATURE:
<221> NAME/KEY: CDS
<222> LOCATION: (284)..(904)

<400> SEQUENCE: 3

```
ttgtattgat acctctggac cattccgcct atttaggtga cactatagaa caagtttgta     60
caaaaaagca ggctggtacc ggtccggaat tcccggata tcgtcgaccc acgcgtccgg    120
cgccggggcc gcctctcctt ccgccggtgc cgcggcgcct catggaagcc ccggagggcg    180 gcggagggggg gcctgcagcg cggggcccgg aggggcagcc ggcgcccgaa gccagggtgc    240
acttccgagt ggcgaggttc atcatggagg tgtcaagcta ggg atg cgg tcc att    295
                                              Met Arg Ser Ile
                                                1 ccc att gcc act gct tgc acc att tac cat aag ttc ttt tgc gag acc    343
Pro Ile Ala Thr Ala Cys Thr Ile Tyr His Lys Phe Phe Cys Glu Thr
  5              10                  15                  20 aac ctg gac gcc tat gac cct tac ctg att gcc atg tct tca att tac    391
Asn Leu Asp Ala Tyr Asp Pro Tyr Leu Ile Ala Met Ser Ser Ile Tyr
              25                  30                  35 ttg gcc ggc aaa gtg gaa gag cag cac ctg cgg act cgt gac atc atc    439
Leu Ala Gly Lys Val Glu Glu Gln His Leu Arg Thr Arg Asp Ile Ile
          40                  45                  50
```

-continued

| | | |
|---|---|---|
| aat gtg tcc aac agg tac ttt aac cca agc ggt gag ccc ctg gaa ttg<br>Asn Val Ser Asn Arg Tyr Phe Asn Pro Ser Gly Glu Pro Leu Glu Leu<br>55                        60                    65 | 487 |

```
aat gtg tcc aac agg tac ttt aac cca agc ggt gag ccc ctg gaa ttg     487
Asn Val Ser Asn Arg Tyr Phe Asn Pro Ser Gly Glu Pro Leu Glu Leu
         55                  60                  65 gac tcc cgc ttc tgg gaa ctc cgg gac agc atc gtg cag tgt gag ctt     535
Asp Ser Arg Phe Trp Glu Leu Arg Asp Ser Ile Val Gln Cys Glu Leu
 70                  75                  80 ctc atg ctg aga gtt ctg cgc ttc cag gtc tcc ttc cag cat cca cac     583
Leu Met Leu Arg Val Leu Arg Phe Gln Val Ser Phe Gln His Pro His
 85                  90                  95                 100 aag tac ctg ctc cac tac ctg gtt tcc ctc cag aac tgg ctg aac cgc     631
Lys Tyr Leu Leu His Tyr Leu Val Ser Leu Gln Asn Trp Leu Asn Arg
             105                 110                 115 cac agc tgg cag cgg acc cct gtt gcc gtc acc gcc tgg gcc ctg ctg     679
His Ser Trp Gln Arg Thr Pro Val Ala Val Thr Ala Trp Ala Leu Leu
         120                 125                 130 cgg gac agc tac cat ggg gcg ctg tgc ctc cgc ttc cag gcc cag cac     727
Arg Asp Ser Tyr His Gly Ala Leu Cys Leu Arg Phe Gln Ala Gln His
 135                 140                 145 atc gcc gtg gcg gtg ctc tac ctg gcc ctg cag gtc tac gga gtt gag     775
Ile Ala Val Ala Val Leu Tyr Leu Ala Leu Gln Val Tyr Gly Val Glu
     150                 155                 160 gtg ccc gcc gag gtc gag gct gag aag ccg tgg tgg cag gtg ttt aat     823
Val Pro Ala Glu Val Glu Ala Glu Lys Pro Trp Trp Gln Val Phe Asn
165                 170                 175                 180 gac gac ctt acc aag cca atc att gat aat att gtg tct gat ctc att     871
Asp Asp Leu Thr Lys Pro Ile Ile Asp Asn Ile Val Ser Asp Leu Ile
             185                 190                 195 cag att tat acc atg gac aca gag atc ccc taa ggtcctgg cccaggcctg    922
Gln Ile Tyr Thr Met Asp Thr Glu Ile Pro  *
         200                 205 cccaaagaga agcccaggat ggtcggctgc tgggggacat tgtcaccacg tcgccatgac   982
ggctggtccc cacaggacca gctgggagga ctggttgtgc tgctggagaa gggctggaga  1042
aggcaatggc atgctgccgc tttgccagtc cctagaagtc gcggtgcagg tgatggtggg  1102
agccgcgcct ccagcgggca ggccgggagt gtactgtgtg cagctgaccc aaggcagcca  1162
catctgcgtt tgtcctttga gaggactttg actacaatac aggcatgaca tcaatgaaag  1222
gaaagtcatg aaatcgatga gactgaatcc ctacggattt cttaaaagcc agatttgtag  1282
ggagaatgaa tgtgcaacgt ggctgaaatc tattttgtgt aataaaaggt gatacaagtc  1342
aaaaaaaaaa aaaaa                                                    1357
```

<210> SEQ ID NO 4
<211> LENGTH: 2353
<212> TYPE: DNA
<213> ORGANISM: Homo sapiens
<220> FEATURE:
<221> NAME/KEY: CDS
<222> LOCATION: (386)..(1783)

<400> SEQUENCE: 4

```
atccgggccc ttccagaagc aacccaggag ccccgagacc tgcagggatg tgtgcaccct    60 gaccctgac gcatagccct gcacctgcag ccagctggcc tcgggcttga aaacatggcg   120
ggtgcgctcc aattcacggt ggtttccaag cgcattctgg aggagaaaac acatgagtgt   180
gtggtcaggg ttctctgccg acagacctac cgtggggaag aaagagaagt tctgaagatg   240
gatcatggcc gtgactgcat gtcaaggaga atctccatga tgacacggag gcctacgtcg   300
agatagagta aatatggtcc aattaaaagg tgacccgaca atcaaccct gaaaaaggcg   360
```

```
gtcataaaac ccccaggaga cgaag atg atg gca cgt cgt gac ccc aaa cct        412
                           Met Met Ala Arg Arg Asp Pro Lys Pro
                             1               5 ggg gca aag aga ctg gtg aga gcc cag acc ctc cag aag cag cgg agg        460
Gly Ala Lys Arg Leu Val Arg Ala Gln Thr Leu Gln Lys Gln Arg Arg
 10              15                  20                  25 gcc cca gtt ggg cca agg gct ccc ccg ccc gat gaa gaa gat ccc agg        508
Ala Pro Val Gly Pro Arg Ala Pro Pro Pro Asp Glu Glu Asp Pro Arg
             30                  35                  40 ctc aag tgc aaa aac tgt gag gcc ttt ggc cac acg gcc aga agt acc        556
Leu Lys Cys Lys Asn Cys Glu Ala Phe Gly His Thr Ala Arg Ser Thr
                 45                  50                  55 agg tgc ccc atg aag tgc tgg aag gca gcc ctg gtt cca ccg aac ttt        604
Arg Cys Pro Met Lys Cys Trp Lys Ala Ala Leu Val Pro Pro Asn Phe
             60                  65                  70 ggg gaa aag gaa ggg aag gaa aac ctg aaa cca tgg aag ccc cag gtt        652
Gly Glu Lys Glu Gly Lys Glu Asn Leu Lys Pro Trp Lys Pro Gln Val
     75                  80                  85 gaa gcg aac cct ggg ccc ttg aac aag gat aag gga gag aag gaa gag        700
Glu Ala Asn Pro Gly Pro Leu Asn Lys Asp Lys Gly Glu Lys Glu Glu
 90              95                 100                 105 aga cca agg cca caa gac ccg cag agg aag gct ctc ctc cac ata ttt        748
Arg Pro Arg Pro Gln Asp Pro Gln Arg Lys Ala Leu Leu His Ile Phe
                110                 115                 120 tcc ggg aaa cct cca gag aag ccg ctg cca aat caa aaa gga tcc acg        796
Ser Gly Lys Pro Pro Glu Lys Pro Leu Pro Asn Gln Lys Gly Ser Thr
                125                 130                 135 gaa tct tct gat tat ctg agg gtt gca agc ggg cca atg ccg gtc cac        844
Glu Ser Ser Asp Tyr Leu Arg Val Ala Ser Gly Pro Met Pro Val His
            140                 145                 150 aca acc agt aag agg ccg cgt gtg gac cct gtc ctc tct gat cgc tca        892
Thr Thr Ser Lys Arg Pro Arg Val Asp Pro Val Leu Ser Asp Arg Ser
    155                 160                 165 gct acc gaa atg tct gac agg ggc tcc gtc tta gct tca ctg tct ccc        940
Ala Thr Glu Met Ser Asp Arg Gly Ser Val Leu Ala Ser Leu Ser Pro
170                 175                 180                 185 ctc aga aaa gcc agt ctg agc tcc tcc tca agt ctt gga cca aag gaa        988
Leu Arg Lys Ala Ser Leu Ser Ser Ser Ser Leu Gly Pro Lys Glu
                190                 195                 200 aga cag aca ggg gct gcg gcc gac atc cct cag act gca gtc agg cac       1036
Arg Gln Thr Gly Ala Ala Ala Asp Ile Pro Gln Thr Ala Val Arg His
                205                 210                 215 cag ggc ccc gag cct ctc ctc gtg gtg aag ccg aca cac agc agc cct       1084
Gln Gly Pro Glu Pro Leu Leu Val Val Lys Pro Thr His Ser Ser Pro
        220                 225                 230 gag ggt ggc tgt cga gaa gtt ccc cag gct gcc tcc aaa acc cac ggc       1132
Glu Gly Gly Cys Arg Glu Val Pro Gln Ala Ala Ser Lys Thr His Gly
    235                 240                 245 ctg ctc cag gcc gtc aga ccc cag gca caa gac aaa cgt cct gcg gtg       1180
Leu Leu Gln Ala Val Arg Pro Gln Ala Gln Asp Lys Arg Pro Ala Val
250                 255                 260                 265 acc tca cag ccc tgc cca cca gcc gcc aca cac agc ttg ggc cta ggc       1228
Thr Ser Gln Pro Cys Pro Pro Ala Ala Thr His Ser Leu Gly Leu Gly
                270                 275                 280 tcc aat ctc agc ttc ggg cca gga gcc aag aga tct gcc ccg gct ccg       1276
Ser Asn Leu Ser Phe Gly Pro Gly Ala Lys Arg Ser Ala Pro Ala Pro
                285                 290                 295 att cag gct tgc ctg aac ttc ccc aag aaa ccg aga ctg ggt ccc ttc       1324
Ile Gln Ala Cys Leu Asn Phe Pro Lys Lys Pro Arg Leu Gly Pro Phe
```

-continued

```
               300                 305                 310
cag atc ccc gaa agc gcc atc cag gga ggt gag ctg ggg gcc ccg gag      1372
Gln Ile Pro Glu Ser Ala Ile Gln Gly Gly Glu Leu Gly Ala Pro Glu
    315                 320                 325 aat ctc caa cct ccg cca gcc gca acc gaa ctt gga cca cgt acc gtg      1420
Asn Leu Gln Pro Pro Pro Ala Ala Thr Glu Leu Gly Pro Arg Thr Val
330                 335                 340                 345 tca ccc cag ata ggc acg agg aca ccc gcc cag gtg ctt agc ggc gac      1468
Ser Pro Gln Ile Gly Thr Arg Thr Pro Ala Gln Val Leu Ser Gly Asp
                350                 355                 360 cgg cag cct ccg cac agc aga cct tgc ctg cct act gcc cag gcc tgc      1516
Arg Gln Pro Pro His Ser Arg Pro Cys Leu Pro Thr Ala Gln Ala Cys
            365                 370                 375 acc atg tcc cat cac cca gcg gcc agc cat gat ggg gcc cag cct ctc      1564
Thr Met Ser His His Pro Ala Ala Ser His Asp Gly Ala Gln Pro Leu
        380                 385                 390 aga gtg ctc ttt cgg aga ctg gaa aac gga cgc tgg agc tcc agc ctg      1612
Arg Val Leu Phe Arg Arg Leu Glu Asn Gly Arg Trp Ser Ser Ser Leu
    395                 400                 405 ctg acg gcc ccc tca ttt cac tct cct gag aag ccg gga gcc ttc ctc      1660
Leu Thr Ala Pro Ser Phe His Ser Pro Glu Lys Pro Gly Ala Phe Leu
410                 415                 420                 425 gct cag agc cct cat gtc tca gag aag tct gag ggt ccc tgt gtt cgt      1708
Ala Gln Ser Pro His Val Ser Glu Lys Ser Glu Gly Pro Cys Val Arg
                430                 435                 440 gtc cca cca agc gtc ctc tat gag gac ctt cag gtt ccc tcc tcc tca      1756
Val Pro Pro Ser Val Leu Tyr Glu Asp Leu Gln Val Pro Ser Ser Ser
            445                 450                 455 gag gac agc gat tct gac ctg gag tga gactg caggtggcag gggctccttg      1808
Glu Asp Ser Asp Ser Asp Leu Glu *
        460                 465 gcctccagct cccgtgactt ggaggggact gtgggactga ggagcacaga gcagagagca    1868
gactctgtgc ggtgactccg aagctccccg gctgtggccc ttctgtggat gtgggagccc    1928
aggccaggca gggagcagat gcagggactc tgccccgttg aattctggtg agggacattg    1988
tagttcgcat ggttctctgg aaacgcgcca ggaaaagctt ccgtgccagt gattcgttgc    2048
ctcagaaact gcatgacgcg caggagtcag acttccgctg ggacgtcaat aggaaacggg    2108
ggaattactg tgtatttgct ctctagacga ctgaataagg aaaagttag ggaaccctga     2168 gaggtgcagc ccttccgctg tgccccgccc tgagagcagt gtttccgacg ctgggaagcg    2228
cgctgtgcaa agcgctctcg gggtctttcc tcagcctcga aaagtgggct ctggaatccc    2288
tttgtaaata ggtgtgttga atttgttttg aagtgaataa aattctcaaa agaaaaaaaa    2348
aaaaa                                                                 2353
```

<210> SEQ ID NO 5
<211> LENGTH: 897
<212> TYPE: DNA
<213> ORGANISM: Homo sapiens
<220> FEATURE:
<221> NAME/KEY: CDS
<222> LOCATION: (1)..(897)

<400> SEQUENCE: 5

```
atg gag gga tat tcc aac aag aaa ttg gat aat atg tct ttg gat gat        48
Met Glu Gly Tyr Ser Asn Lys Lys Leu Asp Asn Met Ser Leu Asp Asp
  1               5                  10                  15 gct gtt tgc caa ggc act gcg ggc agg aaa ggc aaa cga aga atg agg        96
Ala Val Cys Gln Gly Thr Ala Gly Arg Lys Gly Lys Arg Arg Met Arg
```

|  |  |  |  |  |  |  |  |  |  |  |  |  |  |  |  |
|---|---|---|---|---|---|---|---|---|---|---|---|---|---|---|---|
|  |  |  | 20 |  |  |  |  | 25 |  |  |  |  | 30 |  |  |

```
tac gca ggc aac tgg agg gtg aac aag atg aag agg agc ttt att gag      144
Tyr Ala Gly Asn Trp Arg Val Asn Lys Met Lys Arg Ser Phe Ile Glu
             35                  40                  45 tgt tac aac agc tta gag gag acc cac agg agg acg gcg gac ctg ctc      192
Cys Tyr Asn Ser Leu Glu Glu Thr His Arg Arg Thr Ala Asp Leu Leu
 50                  55                  60 tcc gtg gtc atg gcc cag cag agg gga agc gca gct cag tgt cca agt      240
Ser Val Val Met Ala Gln Gln Arg Gly Ser Ala Ala Gln Cys Pro Ser
 65                  70                  75                  80 tac aca gac tcg cag aat ctc aca ggt gtc tta gaa ttt ctc ttc ctg      288
Tyr Thr Asp Ser Gln Asn Leu Thr Gly Val Leu Glu Phe Leu Phe Leu
                 85                  90                  95 gga ctc tca gag gat cca gaa ctg cag ccc gtc ctc gtt ggg ctg ttc      336
Gly Leu Ser Glu Asp Pro Glu Leu Gln Pro Val Leu Val Gly Leu Phe
                100                 105                 110 ctg tcc atg tac ctg atc acg gtg ctg ggg aac ctg ctc atc atc ctg      384
Leu Ser Met Tyr Leu Ile Thr Val Leu Gly Asn Leu Leu Ile Ile Leu
            115                 120                 125 gcc gtc agc tgt gac tcc cac ctc cac acc ccc atg tac ttc ttc ctc      432
Ala Val Ser Cys Asp Ser His Leu His Thr Pro Met Tyr Phe Phe Leu
        130                 135                 140 tcc aac ttg tcc ttg gct gac atc gga ctc acc tct gcc acc atc cct      480
Ser Asn Leu Ser Leu Ala Asp Ile Gly Leu Thr Ser Ala Thr Ile Pro
145                 150                 155                 160 aag atg att gtt gat atg caa tct cac agc aga atc atc tcc tat gag      528
Lys Met Ile Val Asp Met Gln Ser His Ser Arg Ile Ile Ser Tyr Glu
                165                 170                 175 ggc tgc ctg atg cag atg tct tta tct att ttg aag ggt gcg gtc acc      576
Gly Cys Leu Met Gln Met Ser Leu Ser Ile Leu Lys Gly Ala Val Thr
            180                 185                 190 tca gtg atg tac act gtg gtc atc cct atg ctg aac ccc ttc atc tac      624
Ser Val Met Tyr Thr Val Val Ile Pro Met Leu Asn Pro Phe Ile Tyr
        195                 200                 205 agc ctg aga aac agg gac att aaa atc tcc aag atg att gtg gac atc      672
Ser Leu Arg Asn Arg Asp Ile Lys Ile Ser Lys Met Ile Val Asp Ile
    210                 215                 220 cag tct cac agc aga gtc atc tcc tat gcg ggc tgc ctg act cag gta      720
Gln Ser His Ser Arg Val Ile Ser Tyr Ala Gly Cys Leu Thr Gln Val
225                 230                 235                 240 tct ctt ttt gcc gtt ttt gga tgc atg gaa gac atg ctt ctg agt gtg      768
Ser Leu Phe Ala Val Phe Gly Cys Met Glu Asp Met Leu Leu Ser Val
                245                 250                 255 atg gct tat gac cga aaa ggt gca gtg gcc tca gtg atg tac acg gtg      816
Met Ala Tyr Asp Arg Lys Gly Ala Val Ala Ser Val Met Tyr Thr Val
            260                 265                 270 gtt act ccc atg ctg aac ccc ttc atc tac agc cta aca ggg aaa tta      864
Val Thr Pro Met Leu Asn Pro Phe Ile Tyr Ser Leu Thr Gly Lys Leu
        275                 280                 285 aaa gtg ccc tgc ggc agc tgc act gca gaa tag                          897
Lys Val Pro Cys Gly Ser Cys Thr Ala Glu *
    290                 295

<210> SEQ ID NO 6
<211> LENGTH: 3396
<212> TYPE: DNA
<213> ORGANISM: Homo sapiens
<220> FEATURE:
<221> NAME/KEY: CDS
<222> LOCATION: (27)..(2375)
```

```
<400> SEQUENCE: 6
aatttaggtg acactataga agagct atg acg tcg cat gca cgc gta cgt aag        53
                             Met Thr Ser His Ala Arg Val Arg Lys
                              1               5 ctt gga tcc tct aga gcg gcc gcg tcg ccg ctg agg atg tcc cga aag        101
Leu Gly Ser Ser Arg Ala Ala Ala Ser Pro Leu Arg Met Ser Arg Lys
 10              15                  20                  25 ggg ccg cga gcg gag gtg tgt gcg gac tgc agc gcc ccg gac cct ggc        149
Gly Pro Arg Ala Glu Val Cys Ala Asp Cys Ser Ala Pro Asp Pro Gly
             30                  35                  40 tgg gca tcc atc agc agg ggt gtg ctg gtg tgt gac gag tgc tgc agc        197
Trp Ala Ser Ile Ser Arg Gly Val Leu Val Cys Asp Glu Cys Cys Ser
                 45                  50                  55 gtg cac cgg agc ctg gga cgc cac atc tcc att gtc aag cac ctt cgc        245
Val His Arg Ser Leu Gly Arg His Ile Ser Ile Val Lys His Leu Arg
         60                  65                  70 cac agc gcc tgg cct ccc acg ctg ctg cag atg gtg cac acg ctt gcc        293
His Ser Ala Trp Pro Pro Thr Leu Leu Gln Met Val His Thr Leu Ala
     75                  80                  85 agc aac ggg gcc aac tcc atc tgg gag cac tcc ctg ctg gac ccc gca        341
Ser Asn Gly Ala Asn Ser Ile Trp Glu His Ser Leu Leu Asp Pro Ala
 90              95                 100                 105 caa gtg cag agc ggc cgg cgt aaa gcc aac ccc caa gac aaa gtc cac        389
Gln Val Gln Ser Gly Arg Arg Lys Ala Asn Pro Gln Asp Lys Val His
            110                 115                 120 ccc atc aag tca gag ttc atc agg gcc aag tac cag atg ctg gca ttt        437
Pro Ile Lys Ser Glu Phe Ile Arg Ala Lys Tyr Gln Met Leu Ala Phe
        125                 130                 135 gtg cac aag ctt ccc tgc cgg gac gat gat gga gtc acc gcc aaa gac        485
Val His Lys Leu Pro Cys Arg Asp Asp Asp Gly Val Thr Ala Lys Asp
    140                 145                 150 ctc agc aag caa cta cac tcg agc gtg cgg aca ggc aac ctg gag aca        533
Leu Ser Lys Gln Leu His Ser Ser Val Arg Thr Gly Asn Leu Glu Thr
155                 160                 165 tgt ctg cgc ctg ctc tcc ctg ggt gcc cag gcc aac ttc ttc cac cca        581
Cys Leu Arg Leu Leu Ser Leu Gly Ala Gln Ala Asn Phe Phe His Pro
170                 175                 180                 185 gag aag ggc acc aca cct ctg cac gtg gct gcc aag gca gga cag aca        629
Glu Lys Gly Thr Thr Pro Leu His Val Ala Ala Lys Ala Gly Gln Thr
                190                 195                 200 ctg cag gcc gag ctg ctt gta gtg tat ggg gct gac cct ggc tcc cct        677
Leu Gln Ala Glu Leu Leu Val Val Tyr Gly Ala Asp Pro Gly Ser Pro
            205                 210                 215 gat gtt aat ggc cgc aca ccc att gac tat gcc agg cag gcg ggg cac        725
Asp Val Asn Gly Arg Thr Pro Ile Asp Tyr Ala Arg Gln Ala Gly His
        220                 225                 230 cat gag ctg gcg gaa agg ctg gtt gag tgc caa tat gag ctc act gac        773
His Glu Leu Ala Glu Arg Leu Val Glu Cys Gln Tyr Glu Leu Thr Asp
    235                 240                 245 cgg ctg gcc ttc tac ctc tgt gga cgc aag ccg gat cac aag aat ggg        821
Arg Leu Ala Phe Tyr Leu Cys Gly Arg Lys Pro Asp His Lys Asn Gly
250                 255                 260                 265 cat tac atc atc cca cag atg gct gac agc ctt gac tta tcc gaa ttg        869
His Tyr Ile Ile Pro Gln Met Ala Asp Ser Leu Asp Leu Ser Glu Leu
                270                 275                 280 gcc aaa gct gct aag aag aag ctg cag gcg ctc agc aac cgg ctt ttt        917
Ala Lys Ala Ala Lys Lys Lys Leu Gln Ala Leu Ser Asn Arg Leu Phe
            285                 290                 295 gag gaa ctc gcc atg gac gtg tat gac gag gtg gat cga aga gaa aat        965
```

```
                Glu Glu Leu Ala Met Asp Val Tyr Asp Glu Val Asp Arg Arg Glu Asn
                                300                 305                 310 gat gca gtg tgg ctg gct acc caa aac cac agc act ctg gtg aca gag        1013
Asp Ala Val Trp Leu Ala Thr Gln Asn His Ser Thr Leu Val Thr Glu
315                 320                 325 cgc agt gct gtg ccc ttc ctg cct gtt aac ccg gaa tac tca gcc acg        1061
Arg Ser Ala Val Pro Phe Leu Pro Val Asn Pro Glu Tyr Ser Ala Thr
330                 335                 340                 345 cgg aat cag ggg cga caa aag ctg gcc cgc ttt aat gcc cga gag ttt        1109
Arg Asn Gln Gly Arg Gln Lys Leu Ala Arg Phe Asn Ala Arg Glu Phe
                350                 355                 360 gcc acc ttg atc atc gac att ctc agt gag gcc aag cgg aga cag cag        1157
Ala Thr Leu Ile Ile Asp Ile Leu Ser Glu Ala Lys Arg Arg Gln Gln
            365                 370                 375 ggc aag agc ctg agc agc ccc aca gac aac ctc gag ctg tct ctg cgg        1205
Gly Lys Ser Leu Ser Ser Pro Thr Asp Asn Leu Glu Leu Ser Leu Arg
        380                 385                 390 agc cag agt gac ctc gac gac caa cac gac tac gac agc gtg gcc tct        1253
Ser Gln Ser Asp Leu Asp Asp Gln His Asp Tyr Asp Ser Val Ala Ser
    395                 400                 405 gac gag gac aca gac cag gag ccc ctg cgc agc acc ggc gcc act cgg        1301
Asp Glu Asp Thr Asp Gln Glu Pro Leu Arg Ser Thr Gly Ala Thr Arg
410                 415                 420                 425 agc aac cgg gcc cgg agc atg gac tcc tcg gac ttg tct gac ggg gct        1349
Ser Asn Arg Ala Arg Ser Met Asp Ser Ser Asp Leu Ser Asp Gly Ala
                430                 435                 440 gtg acg ctg cag gag tac ctg gag ctg aag aag gcc ctg gct aca tcg        1397
Val Thr Leu Gln Glu Tyr Leu Glu Leu Lys Lys Ala Leu Ala Thr Ser
            445                 450                 455 gag gca aag gtg cag cag ctc atg aag gtc aac agt agc ctg agc gac        1445
Glu Ala Lys Val Gln Gln Leu Met Lys Val Asn Ser Ser Leu Ser Asp
        460                 465                 470 gag ctc cgg agg ctg cag cga gag atc cac aag ctg cag gcg gag aac        1493
Glu Leu Arg Arg Leu Gln Arg Glu Ile His Lys Leu Gln Ala Glu Asn
    475                 480                 485 ctg cag ctc cgg cag cct cca ggg ccg gtg ccc aca cct cca ctc ccc        1541
Leu Gln Leu Arg Gln Pro Pro Gly Pro Val Pro Thr Pro Pro Leu Pro
490                 495                 500                 505 agt gaa cgg gcg gaa cac aca ccc atg gcg cca ggc ggg agc aca cac        1589
Ser Glu Arg Ala Glu His Thr Pro Met Ala Pro Gly Gly Ser Thr His
                510                 515                 520 cgc agg gat cgc cag gcc ttt tcc atg tat gaa cct ggc tct gcc ctg        1637
Arg Arg Asp Arg Gln Ala Phe Ser Met Tyr Glu Pro Gly Ser Ala Leu
            525                 530                 535 aag ccc ttt ggg ggc cac ctt ggg gac gag ctc act acg cgg ctg cag        1685
Lys Pro Phe Gly Gly His Leu Gly Asp Glu Leu Thr Thr Arg Leu Gln
        540                 545                 550 cct ttc cac agc act gag cta gag gac gac gcc atc tat tca gtg cac        1733
Pro Phe His Ser Thr Glu Leu Glu Asp Asp Ala Ile Tyr Ser Val His
    555                 560                 565 gtc cct gct ggc ctt tac cgg atc cgg aaa ggg gtg tct gcc tca gct        1781
Val Pro Ala Gly Leu Tyr Arg Ile Arg Lys Gly Val Ser Ala Ser Ala
570                 575                 580                 585 gtg ccc ttc act ccc tcc tcc ccg ctg ctg tcc tgc tcc cag gag gga        1829
Val Pro Phe Thr Pro Ser Ser Pro Leu Leu Ser Cys Ser Gln Glu Gly
                590                 595                 600 agc cgc cac acg agc aag ctt tcc cgc cac ggc agt gga gcc gac agt        1877
Ser Arg His Thr Ser Lys Leu Ser Arg His Gly Ser Gly Ala Asp Ser
            605                 610                 615
```

| | | |
|---|---|---|
| gac tat gag aac acg caa agt ggg gac cca ctg ctg ggg ctg gaa ggg<br>Asp Tyr Glu Asn Thr Gln Ser Gly Asp Pro Leu Leu Gly Leu Glu Gly<br>        620                625                630 | 1925 |
| aag agg ttt cta gag ctg ggc aaa gag gaa gac ttc cac cca gag ctg<br>Lys Arg Phe Leu Glu Leu Gly Lys Glu Glu Asp Phe His Pro Glu Leu<br>635                640                645 | 1973 |
| gaa agc ctg gat gga gac cta gat cct ggg ctt ccc agc aca gag gat<br>Glu Ser Leu Asp Gly Asp Leu Asp Pro Gly Leu Pro Ser Thr Glu Asp<br>650                655                660              665 | 2021 |
| gtc atc ttg aag aca gag cag gtc acc aag aac att cag gaa ctg ttg<br>Val Ile Leu Lys Thr Glu Gln Val Thr Lys Asn Ile Gln Glu Leu Leu<br>        670                675                680 | 2069 |
| cgg gca gcc cag gag ttc aag cat gac agc ttc gtg ccc tgc tca gag<br>Arg Ala Ala Gln Glu Phe Lys His Asp Ser Phe Val Pro Cys Ser Glu<br>                685                690              695 | 2117 |
| aag atc cat ttg gct gtg acc gag atg gcc tcc ctc ttc cca aag agg<br>Lys Ile His Leu Ala Val Thr Glu Met Ala Ser Leu Phe Pro Lys Arg<br>        700                705                710 | 2165 |
| cca gcc ctg gag cca gtg cgg agc tca ctg cgg ctg ctc aac gcc agc<br>Pro Ala Leu Glu Pro Val Arg Ser Ser Leu Arg Leu Leu Asn Ala Ser<br>715                720                725 | 2213 |
| gcc tac cgg ctg cag agt gag tgc cgg aag aca gtg ccc cca gag ccc<br>Ala Tyr Arg Leu Gln Ser Glu Cys Arg Lys Thr Val Pro Pro Glu Pro<br>730                735                740              745 | 2261 |
| ggc gcc cca gtg gac ttc cag ctg ctg act cag cag gtg atc cag tgc<br>Gly Ala Pro Val Asp Phe Gln Leu Leu Thr Gln Gln Val Ile Gln Cys<br>                750                755              760 | 2309 |
| gcc tat gac atc gcc aag gct gcc aag cag ctg gtc acc atc acc acc<br>Ala Tyr Asp Ile Ala Lys Ala Ala Lys Gln Leu Val Thr Ile Thr Thr<br>        765                770                775 | 2357 |
| cga gag aag aag cag tga cctctc tccccacacc ctcacctgca ccctaggacc<br>Arg Glu Lys Lys Gln *<br>780 | 2411 |
| tcactggcca taggagctgg gccactccag acattaatcc ccaccccaac agagccactg | 2471 |
| gcacaagtgc ccttagtgct gccacactcc ctggcagcca ggtgccctgg tgcccacccc | 2531 |
| tgtcgagccc ctaaggatgg ggaggtgggg gggcaggagc ttctgtcccc cacattccat | 2591 |
| gcacctcccc tctgtatata gcatctcccc cctcctagtg agcaggggcc tgcaaggcat | 2651 |
| cactcccagc ccctcgcctt ctagggcacc ctcagcaaag gggcaggtgg ggacactcca | 2711 |
| agtggggcag ctctccgtac atgcgcccca ccccatgag ccagttcagc cctactgggg | 2771 |
| gctgagcggg ggcatcccct cctttgtaca tagtctccat ggatgtccct gccctgtagc | 2831 |
| caccagcccc ttgctgctct ccctttaatg ccatatggcc cctgcctagg cacaggccc | 2891 |
| caacctgtgt gctgggtcc ccagcagcaa acactggaaa gtctgttttt tttttttctt | 2951 |
| tcttcttccc cacccttaa ttttaacttt gtggtaactg agtgcccccg cgtgcctgcg | 3011 |
| tgttgagtgt gtggggcggc agtgccgttc cggaggcctg gtccatctgg agttttgagg | 3071 |
| ggtgagggga ccagagcagt gggaccagca tggggatcag cttcccttcc ccacctggga | 3131 |
| gccagggact gtccgggtag ccagtttttgg tcctgccagc tgcctccctg atccctcccc | 3191 |
| actctcgccc cttctctatg aacttaaatc aaaaaccact tccctccatc tcctcctgct | 3251 |
| cctgcgtgga gggggaatgt gtgctggcta aggtggagga ctgagcagct gagcctgggg | 3311 |
| ctggctcccc gggggtctcg actcagctgg tggcttttga actgagtccc tcccgtaaac | 3371 |
| tcttcaagcc agcaccacca taatt | 3396 |

-continued

```
<210> SEQ ID NO 7
<211> LENGTH: 3423
<212> TYPE: DNA
<213> ORGANISM: Homo sapiens
<220> FEATURE:
<221> NAME/KEY: CDS
<222> LOCATION: (27)..(2402)

<400> SEQUENCE: 7
aatttaggtg acactataga agagct atg acg tcg cat gca cgc gta cgt aag        53
                             Met Thr Ser His Ala Arg Val Arg Lys
                              1               5 ctt gga tcc tct aga gcg gcc gcg tcg ccg ctg agg atg tcc cga aag        101
Leu Gly Ser Ser Arg Ala Ala Ala Ser Pro Leu Arg Met Ser Arg Lys
 10              15                  20                  25 ggg ccg cga gcg gag gtg tgt gcg gac tgc agc gcc ccg gac cct ggc        149
Gly Pro Arg Ala Glu Val Cys Ala Asp Cys Ser Ala Pro Asp Pro Gly
             30                  35                  40 tgg gca tcc atc agc agg ggt gtg ctg gtg tgt gac gag tgc tgc agc        197
Trp Ala Ser Ile Ser Arg Gly Val Leu Val Cys Asp Glu Cys Cys Ser
                 45                  50                  55 gtg cac cgg agc ctg gga cgc cac atc tcc att gtc aag cac ctt cgc        245
Val His Arg Ser Leu Gly Arg His Ile Ser Ile Val Lys His Leu Arg
         60                  65                  70 cac agc gcc tgg cct ccc acg ctg ctg cag atg gtg cac acg ctt gcc        293
His Ser Ala Trp Pro Pro Thr Leu Leu Gln Met Val His Thr Leu Ala
     75                  80                  85 agc aac ggg gcc aac tcc atc tgg gag cac tcc ctg ctg gac ccc gca        341
Ser Asn Gly Ala Asn Ser Ile Trp Glu His Ser Leu Leu Asp Pro Ala
 90                  95                 100                 105 caa gtg cag agc ggc cgg cgt aaa gcc aac ccc caa gac aaa gtc cac        389
Gln Val Gln Ser Gly Arg Arg Lys Ala Asn Pro Gln Asp Lys Val His
                110                 115                 120 ccc atc aag tca gag ttc atc agg gcc aag tac cag atg ctg gca ttt        437
Pro Ile Lys Ser Glu Phe Ile Arg Ala Lys Tyr Gln Met Leu Ala Phe
            125                 130                 135 gtg cac aag ctt ccc tgc cgg gac gat gat gga gtc acc gcc aaa gac        485
Val His Lys Leu Pro Cys Arg Asp Asp Asp Gly Val Thr Ala Lys Asp
        140                 145                 150 ctc agc aag caa cta cac tcg agc gtg cgg aca ggc aac ctg gag aca        533
Leu Ser Lys Gln Leu His Ser Ser Val Arg Thr Gly Asn Leu Glu Thr
    155                 160                 165 tgt ctg cgc ctg ctc tcc ctg ggt gcc cag gcc aac ttc ttc cac cca        581
Cys Leu Arg Leu Leu Ser Leu Gly Ala Gln Ala Asn Phe Phe His Pro
170                 175                 180                 185 gag aag ggc acc aca cct ctg cac gtg gct gcc aag gca gga cag aca        629
Glu Lys Gly Thr Thr Pro Leu His Val Ala Ala Lys Ala Gly Gln Thr
                190                 195                 200 ctg cag gcc gag ctg ctt gta gtg tat ggg gct gac cct ggc tcc cct        677
Leu Gln Ala Glu Leu Leu Val Val Tyr Gly Ala Asp Pro Gly Ser Pro
            205                 210                 215 gat gtt aat ggc cgc aca ccc att gac tat gcc agg cag gcg ggg cac        725
Asp Val Asn Gly Arg Thr Pro Ile Asp Tyr Ala Arg Gln Ala Gly His
        220                 225                 230 cat gag ctg gcg gaa agg ctg gtt gag tgc caa tat gag ctc act gac        773
His Glu Leu Ala Glu Arg Leu Val Glu Cys Gln Tyr Glu Leu Thr Asp
    235                 240                 245 cgg ctg gcc ttc tac ctc tgt gga cgc aag ccg gat cac aag aat ggg        821
Arg Leu Ala Phe Tyr Leu Cys Gly Arg Lys Pro Asp His Lys Asn Gly
250                 255                 260                 265 cat tac atc atc cca cag atg gct gac aga tct cgg caa aag tgc atg        869
```

```
                His Tyr Ile Ile Pro Gln Met Ala Asp Arg Ser Arg Gln Lys Cys Met
                                275                 280
tct cag agc ctt gac tta tcc gaa ttg gcc aaa gct gct aag aag aag           917
Ser Gln Ser Leu Asp Leu Ser Glu Leu Ala Lys Ala Ala Lys Lys Lys
            285                 290                 295 ctg cag gcg ctc agc aac cgg ctt ttt gag gaa ctc gcc atg gac gtg           965
Leu Gln Ala Leu Ser Asn Arg Leu Phe Glu Glu Leu Ala Met Asp Val
        300                 305                 310 tat gac gag gtg gat cga aga gaa aat gat gca gtg tgg ctg gct acc          1013
Tyr Asp Glu Val Asp Arg Arg Glu Asn Asp Ala Val Trp Leu Ala Thr
    315                 320                 325 caa aac cac agc act ctg gtg aca gag cgc agt gct gtg ccc ttc ctg          1061
Gln Asn His Ser Thr Leu Val Thr Glu Arg Ser Ala Val Pro Phe Leu
330                 335                 340                 345 cct gtt aac ccg gaa tac tca gcc acg cgg aat cag ggg cga caa aag          1109
Pro Val Asn Pro Glu Tyr Ser Ala Thr Arg Asn Gln Gly Arg Gln Lys
                350                 355                 360 ctg gcc cgc ttt aat gcc cga gag ttt gcc acc ttg atc atc gac att          1157
Leu Ala Arg Phe Asn Ala Arg Glu Phe Ala Thr Leu Ile Ile Asp Ile
            365                 370                 375 ctc agt gag gcc aag cgg aga cag cag ggc aag agc ctg agc agc ccc          1205
Leu Ser Glu Ala Lys Arg Arg Gln Gln Gly Lys Ser Leu Ser Ser Pro
        380                 385                 390 aca gac aac ctc gag ctg tct ctg cgg agc cag agt gac ctc gac gac          1253
Thr Asp Asn Leu Glu Leu Ser Leu Arg Ser Gln Ser Asp Leu Asp Asp
    395                 400                 405 caa cac gac tac gac agc gtg gcc tct gac gag gac aca gac cag gag          1301
Gln His Asp Tyr Asp Ser Val Ala Ser Asp Glu Asp Thr Asp Gln Glu
410                 415                 420                 425 ccc ctg cgc agc acc ggc gcc act cgg agc aac cgg gcc cgg agc atg          1349
Pro Leu Arg Ser Thr Gly Ala Thr Arg Ser Asn Arg Ala Arg Ser Met
                430                 435                 440 gac tcc tcg gac ttg tct gac ggg gct gtg acg ctg cag gag tac ctg          1397
Asp Ser Ser Asp Leu Ser Asp Gly Ala Val Thr Leu Gln Glu Tyr Leu
            445                 450                 455 gag ctg aag aag gcc ctg gct aca tcg gag gca aag gtg cag cag ctc          1445
Glu Leu Lys Lys Ala Leu Ala Thr Ser Glu Ala Lys Val Gln Gln Leu
        460                 465                 470 atg aag gtc aac agt agc ctg agc gac gag ctc cgg agg ctg cag cga          1493
Met Lys Val Asn Ser Ser Leu Ser Asp Glu Leu Arg Arg Leu Gln Arg
    475                 480                 485 gag atc cac aag ctg cag gcg gag aac ctg cag ctc cgg cag cct cca          1541
Glu Ile His Lys Leu Gln Ala Glu Asn Leu Gln Leu Arg Gln Pro Pro
490                 495                 500                 505 ggg ccg gtg ccc aca cct cca ctc ccc agt gaa cgg gcg gaa cac aca          1589
Gly Pro Val Pro Thr Pro Pro Leu Pro Ser Glu Arg Ala Glu His Thr
                510                 515                 520 ccc atg gcg cca ggc ggg agc aca cac cgc agg gat cgc cag gcc ttt          1637
Pro Met Ala Pro Gly Gly Ser Thr His Arg Arg Asp Arg Gln Ala Phe
            525                 530                 535 tcc atg tat gaa cct ggc tct gcc ctg aag ccc ttt ggg ggc cac ctt          1685
Ser Met Tyr Glu Pro Gly Ser Ala Leu Lys Pro Phe Gly Gly His Leu
        540                 545                 550 ggg gac gag ctc act acg cgg ctg cag cct ttc cac agc act gag cta          1733
Gly Asp Glu Leu Thr Thr Arg Leu Gln Pro Phe His Ser Thr Glu Leu
    555                 560                 565 gag gac gac gcc atc tat tca gtg cac gtc cct gct ggc ctt tac cgg          1781
Glu Asp Asp Ala Ile Tyr Ser Val His Val Pro Ala Gly Leu Tyr Arg
570                 575                 580                 585
```

-continued

```
atc cgg aaa ggg gtg tct gcc tca gct gtg ccc ttc act ccc tcc tcc    1829
Ile Arg Lys Gly Val Ser Ala Ser Ala Val Pro Phe Thr Pro Ser Ser
            590                 595                 600 ccg ctg ctg tcc tgc tcc cag gag gga agc cgc cac acg agc aag ctt    1877
Pro Leu Leu Ser Cys Ser Gln Glu Gly Ser Arg His Thr Ser Lys Leu
            605                 610                 615 tcc cgc cac ggc agt gga gcc gac agt gac tat gag aac acg caa agt    1925
Ser Arg His Gly Ser Gly Ala Asp Ser Asp Tyr Glu Asn Thr Gln Ser
            620                 625                 630 ggg gac cca ctg ctg ggg ctg gaa ggg aag agg ttt cta gag ctg ggc    1973
Gly Asp Pro Leu Leu Gly Leu Glu Gly Lys Arg Phe Leu Glu Leu Gly
            635                 640                 645 aaa gag gaa gac ttc cac cca gag ctg gaa agc ctg gat gga gac cta    2021
Lys Glu Glu Asp Phe His Pro Glu Leu Glu Ser Leu Asp Gly Asp Leu
650                 655                 660                 665 gat cct ggg ctt ccc agc aca gag gat gtc atc ttg aag aca gag cag    2069
Asp Pro Gly Leu Pro Ser Thr Glu Asp Val Ile Leu Lys Thr Glu Gln
                670                 675                 680 gtc acc aag aac att cag gaa ctg ttg cgg gca gcc cag gag ttc aag    2117
Val Thr Lys Asn Ile Gln Glu Leu Leu Arg Ala Ala Gln Glu Phe Lys
            685                 690                 695 cat gac agc ttc gtg ccc tgc tca gag aag atc cat ttg gct gtg acc    2165
His Asp Ser Phe Val Pro Cys Ser Glu Lys Ile His Leu Ala Val Thr
            700                 705                 710 gag atg gcc tcc ctc ttc cca aag agg cca gcc ctg gag cca gtg cgg    2213
Glu Met Ala Ser Leu Phe Pro Lys Arg Pro Ala Leu Glu Pro Val Arg
715                 720                 725 agc tca ctg cgg ctg ctc aac gcc agc gcc tac cgg ctg cag agt gag    2261
Ser Ser Leu Arg Leu Leu Asn Ala Ser Ala Tyr Arg Leu Gln Ser Glu
730                 735                 740                 745 tgc cgg aag aca gtg ccc cca gag ccc ggc gcc cca gtg gac ttc cag    2309
Cys Arg Lys Thr Val Pro Pro Glu Pro Gly Ala Pro Val Asp Phe Gln
                750                 755                 760 ctg ctg act cag cag gtg atc cag tgc gcc tat gac atc gcc aag gct    2357
Leu Leu Thr Gln Gln Val Ile Gln Cys Ala Tyr Asp Ile Ala Lys Ala
            765                 770                 775 gcc aag cag ctg gtc acc atc acc acc cga gag aag aag cag tga cct    2405
Ala Lys Gln Leu Val Thr Ile Thr Thr Arg Glu Lys Lys Gln *
            780                 785                 790 ctctccccac accctcacct gcaccctagg acctcactgg ccataggagc tgggccactc    2465
cagacattaa tccccacccc aacagagcca ctggcacaag tgcccttagt gctgccacac    2525
tccctggcag ccaggtgccc tggtgcccac ccctgtcgag cccctaagga tggggaggtg    2585
ggggggcagg agcttctgtc ccccacattc catgcacctc ccctctgtat atagcatctc    2645 cccctccta gtgagcaggg gcctgcaagg catcactccc agccctcgc cttctagggc    2705 accctcagca aagggcagg tggggacact ccaagtgggg cagctctccg tacatgcgcc    2765 ccaccccat gagccagttc agccctactg ggggctgagc ggggcatcc cctcctttgt    2825 acatagtctc catggatgtc cctgccctgt agccaccagc cccttgctgc tctccttta    2885 atgccatatg gcccctgcct agggcacagg ccccaacctg tgtgctgggg tcccagcag    2945 caaaactgg aaagtctgtt ttttttttt ctttcttctt ccccacccct taattttaac    3005
tttgtggtaa ctgagtgccc ccgcgtgcct gcgtgttgag tgtgtgggc ggcagtgccg    3065 ttccggaggc ctggtccatc tggagttttg aggggtgagg ggaccagagc agtgggacca    3125
gcatggggat cagcttccct tccccacctg ggagccaggg actgtccggg tagccagttt    3185
tggtcctgcc agctgcctcc ctgatccctc cccactctcg cccctttctct atgaacttaa    3245
```

-continued

```
atcaaaaacc acttccctcc atctcctcct gctcctgcgt ggaggggggaa tgtgtgctgg      3305 ctaaggtgga ggactgagca gctgagcctg gggctggctc cccggggggtc tcgactcagc      3365 tggtggcttt tgaactgagt ccctcccgta aactcttcaa gccagcacca ccataatt        3423

<210> SEQ ID NO 8
<211> LENGTH: 2763
<212> TYPE: DNA
<213> ORGANISM: Homo sapiens
<220> FEATURE:
<221> NAME/KEY: CDS
<222> LOCATION: (180)..(1742)

<400> SEQUENCE: 8
atcgacgact tgaacgcctg cggtaccggt ccggaattcc cgggtcgacg atttcgtccg        60
agccctgctc atggcagtga ggtgggctcc cagctgctga ggccacccag cactagtgag      120
tgacttggca ttttattttt tgttcagatc acaagaatgg gcattacatc atcccacag      179 atg gct gac aga tct cgg caa aag tgc atg tct cag agc ctt gac tta        227
Met Ala Asp Arg Ser Arg Gln Lys Cys Met Ser Gln Ser Leu Asp Leu
 1               5                  10                  15 tcc gaa ttg gcc aaa gct gct aag aag aag ctg cag gcg ctc agc aac        275
Ser Glu Leu Ala Lys Ala Ala Lys Lys Lys Leu Gln Ala Leu Ser Asn
                 20                  25                  30 cgg ctt ttt gag gaa ctc gcc atg gac gtg tat gac gag gtg gat cga        323
Arg Leu Phe Glu Glu Leu Ala Met Asp Val Tyr Asp Glu Val Asp Arg
             35                  40                  45 aga gaa aat gat gca gtg tgg ctg gct acc caa aac cac agc act ctg        371
Arg Glu Asn Asp Ala Val Trp Leu Ala Thr Gln Asn His Ser Thr Leu
         50                  55                  60 gtg aca gag cgc agt gct gtg ccc ttc ctg cct gtt aac ccg gaa tac        419
Val Thr Glu Arg Ser Ala Val Pro Phe Leu Pro Val Asn Pro Glu Tyr
 65                  70                  75                  80 tca gcc acg cgg aat cag ggg cga caa aag ctg gcc cgc ttt aat gcc        467
Ser Ala Thr Arg Asn Gln Gly Arg Gln Lys Leu Ala Arg Phe Asn Ala
                 85                  90                  95 cga gag ttt gcc acc ttg atc atc gac att ctc agt gag gcc aag cgg        515
Arg Glu Phe Ala Thr Leu Ile Ile Asp Ile Leu Ser Glu Ala Lys Arg
                100                 105                 110 aga cag cag ggc aag agc ctg agc agc ccc aca gac aac ctc gag ctg        563
Arg Gln Gln Gly Lys Ser Leu Ser Ser Pro Thr Asp Asn Leu Glu Leu
            115                 120                 125 tct ctg cgg agc cag agt gac ctc gac gac caa cac gac tac gac agc        611
Ser Leu Arg Ser Gln Ser Asp Leu Asp Asp Gln His Asp Tyr Asp Ser
        130                 135                 140 gtg gcc tct gac gag gac aca gac cag gag ccc ctg cgc agc acc ggc        659
Val Ala Ser Asp Glu Asp Thr Asp Gln Glu Pro Leu Arg Ser Thr Gly
145                 150                 155                 160 gcc act cgg agc aac cgg gcc cgg agc atg gac tcc tcg gac ttg tct        707
Ala Thr Arg Ser Asn Arg Ala Arg Ser Met Asp Ser Ser Asp Leu Ser
                165                 170                 175 gac ggg gct gtg acg ctg cag gag tac ctg gag ctg aag aag gcc ctg        755
Asp Gly Ala Val Thr Leu Gln Glu Tyr Leu Glu Leu Lys Lys Ala Leu
                180                 185                 190 gct aca tcg gag gca aag gtg cag cag ctc atg aag gtc aac agt agc        803
Ala Thr Ser Glu Ala Lys Val Gln Gln Leu Met Lys Val Asn Ser Ser
            195                 200                 205 ctg agc gac gag ctc cgg agg ctg cag cga gag atc cac aag ctg cag        851
Leu Ser Asp Glu Leu Arg Arg Leu Gln Arg Glu Ile His Lys Leu Gln
        210                 215                 220
```

```
gcg gag aac ctg cag ctc cgg cag cct cca ggg ccg gtg ccc aca cct    899
Ala Glu Asn Leu Gln Leu Arg Gln Pro Pro Gly Pro Val Pro Thr Pro
225                 230                 235                 240 cca ctc ccc agt gaa cgg gcg gaa cac aca ccc atg gcg cca ggc ggg    947
Pro Leu Pro Ser Glu Arg Ala Glu His Thr Pro Met Ala Pro Gly Gly
                245                 250                 255 agc aca cac cgc agg gat cgc cag gcc ttt tcc atg tat gaa cct ggc    995
Ser Thr His Arg Arg Asp Arg Gln Ala Phe Ser Met Tyr Glu Pro Gly
            260                 265                 270 tct gcc ctg aag ccc ttt ggg ggc cac ctt ggg gac gag ctc act acg   1043
Ser Ala Leu Lys Pro Phe Gly Gly His Leu Gly Asp Glu Leu Thr Thr
                275                 280                 285 cgg ctg cag cct ttc cac agc act gag cta gag gac gac gcc atc tat   1091
Arg Leu Gln Pro Phe His Ser Thr Glu Leu Glu Asp Asp Ala Ile Tyr
        290                 295                 300 tca gtg cac gtc cct gct ggc ctt tac cgg atc cgg aaa ggg gtg tct   1139
Ser Val His Val Pro Ala Gly Leu Tyr Arg Ile Arg Lys Gly Val Ser
305                 310                 315                 320 gcc tca gct gtg ccc ttc act ccc tcc tcc ccg ctg ctg tcc tgc tcc   1187
Ala Ser Ala Val Pro Phe Thr Pro Ser Ser Pro Leu Leu Ser Cys Ser
                325                 330                 335 cag gag gga agc cgc cac acg agc aag ctt tcc cgc cac ggc agt gga   1235
Gln Glu Gly Ser Arg His Thr Ser Lys Leu Ser Arg His Gly Ser Gly
            340                 345                 350 gcc gac agt gac tat gag aac acg caa agt ggg gac cca ctg ctg ggg   1283
Ala Asp Ser Asp Tyr Glu Asn Thr Gln Ser Gly Asp Pro Leu Leu Gly
                355                 360                 365 ctg gaa ggg aag agg ttt cta gag ctg ggc aaa gag gaa gac ttc cac   1331
Leu Glu Gly Lys Arg Phe Leu Glu Leu Gly Lys Glu Glu Asp Phe His
370                 375                 380 cca gag ctg gaa agc ctg gat gga gac cta gat cct ggg ctt ccc agc   1379
Pro Glu Leu Glu Ser Leu Asp Gly Asp Leu Asp Pro Gly Leu Pro Ser
385                 390                 395                 400 aca gag gat gtc atc ttg aag aca gag cag gtc acc aag aac att cag   1427
Thr Glu Asp Val Ile Leu Lys Thr Glu Gln Val Thr Lys Asn Ile Gln
                405                 410                 415 gaa ctg ttg cgg gca gcc cag gag ttc aag cat gac agc ttc gtg ccc   1475
Glu Leu Leu Arg Ala Ala Gln Glu Phe Lys His Asp Ser Phe Val Pro
            420                 425                 430 tgc tca gag aag atc cat ttg gct gtg acc gag atg gcc tcc ctc ttc   1523
Cys Ser Glu Lys Ile His Leu Ala Val Thr Glu Met Ala Ser Leu Phe
                435                 440                 445 cca aag agg cca gcc ctg gag cca gtg cgg agc tca ctg cgg ctg ctc   1571
Pro Lys Arg Pro Ala Leu Glu Pro Val Arg Ser Ser Leu Arg Leu Leu
450                 455                 460 aac gcc agc gcc tac cgg ctg cag agt gag tgc cgg aag aca gtg ccc   1619
Asn Ala Ser Ala Tyr Arg Leu Gln Ser Glu Cys Arg Lys Thr Val Pro
465                 470                 475                 480 cca gag ccc ggc gcc cca gtg gac ttc cag ctg ctg act cag cag gtg   1667
Pro Glu Pro Gly Ala Pro Val Asp Phe Gln Leu Leu Thr Gln Gln Val
                485                 490                 495 atc cag tgc gcc tat gac atc gcc aag gct gcc aag cag ctg gtc acc   1715
Ile Gln Cys Ala Tyr Asp Ile Ala Lys Ala Ala Lys Gln Leu Val Thr
            500                 505                 510 atc acc acc cga gag aag aag cag tga cctct ctccccacac cctcacctgc   1767
Ile Thr Thr Arg Glu Lys Lys Gln  *
            515                 520 accctaggac ctcactggcc ataggagctg ggccactcca gacattaatc cccaccccaa  1827
```

-continued

```
cagagccact ggcacaagtg cccttagtgc tgccacactc cctggcagcc aggtgccctg     1887
gtgcccaccc ctgtcgagcc cctaaggatg gggaggtggg ggggcaggag cttctgtccc     1947
ccacattcca tgcacctccc ctctgtatat agcatctccc ccctcctagt gagcagggc      2007 ctgcaaggca tcactcccag cccctcgcct tctagggcac cctcagcaaa ggggcaggtg     2067
gggacactcc aagtggggca gctctccgta catgcgcccc accccatga gccagttcag      2127 ccctactggg ggctgagcgg gggcatcccc tcctttgtac atagtctcca tggatgtccc     2187
tgccctgtag ccaccagccc cttgctgctc tcccttaat gccatatggc ccctgcctag      2247
ggcacaggcc caacctgtg tgctggggtc cccagcagca aacactggaa agtctgtttt      2307 tttttttct tcttcttcc ccacccctta attttaactt tgtggtaact gagtgccccc      2367
gcgtgcctgc gtgttgagtg tgtggggcgg cagtgccgtt ccggaggcct ggtccatctg     2427
gagttttgag gggtgagggg accagagcag tgggaccagc atggggatca gcttcccttc    2487
cccacctggg agccagggac tgtccgggta gccagttttg gtcctgccag ctgcctccct    2547
gatccctccc cactctcgcc ccttctctat gaacttaaat caaaaaccac ttccctccat    2607
ctcctcctgc tcctgcgtgg aggggaatg tgtgctggct aaggtggagg actgagcagc    2667
tgagcctggg gctggctccc cgggggtctc gactcagctg gtggcttttg aactgagtcc    2727
ctcccgtaaa ctcttcaagc cagcaccacc ataatt                              2763
```

<210> SEQ ID NO 9
<211> LENGTH: 1080
<212> TYPE: DNA
<213> ORGANISM: Homo sapiens
<220> FEATURE:
<221> NAME/KEY: CDS
<222> LOCATION: (178)..(1080)

<400> SEQUENCE: 9

```
atgttcaaag ccatccttgg ccatgtgtgg cccaaagacc atgggttgga caagcttgtt     60
gtaaggtgtc caagacacac agagccatgg aatctcacag gtatctcaga attcctcctc    120
ctgggactct cagaggatcc agaactgcag cccgtcctcc ctgggctgtc cctgtcc       177 atg tac ctg gtc acg gtg ctg agg aac ctg ctc atc atc ctg gct gtc     225
Met Tyr Leu Val Thr Val Leu Arg Asn Leu Leu Ile Ile Leu Ala Val
  1               5                  10                  15 agc tct gac tcc cac ctc cac acc ccc atg tgc ttc ttc ctc tcc aac     273
Ser Ser Asp Ser His Leu His Thr Pro Met Cys Phe Phe Leu Ser Asn
             20                  25                  30 ctg tgc tgg gct gac atc ggt ttc acc tcg gcc atg gtt ccc aag atg     321
Leu Cys Trp Ala Asp Ile Gly Phe Thr Ser Ala Met Val Pro Lys Met
         35                  40                  45 att gtg gac atg cag tcg cat agc aga gtc atc tct tat gcg ggc tgc     369
Ile Val Asp Met Gln Ser His Ser Arg Val Ile Ser Tyr Ala Gly Cys
     50                  55                  60 ctg aca cag atg tct ttc ttt gtc ctt ttt gca tgt ata gaa gac atg     417
Leu Thr Gln Met Ser Phe Phe Val Leu Phe Ala Cys Ile Glu Asp Met
 65                  70                  75                  80 ctc ctg aca gtg atg gcc tat gac cga ttt gtg gcc atc tgt cac ccc     465
Leu Leu Thr Val Met Ala Tyr Asp Arg Phe Val Ala Ile Cys His Pro
                 85                  90                  95 ctg cac tac cca gtc atc atg aat cct cac ctt ggt gtc ttc tta gtt     513
Leu His Tyr Pro Val Ile Met Asn Pro His Leu Gly Val Phe Leu Val
            100                 105                 110 ttg gtg tcc ttt ttc ctc agc ctg ttg gat tcc cag ctg cac agt tgg     561
Leu Val Ser Phe Phe Leu Ser Leu Leu Asp Ser Gln Leu His Ser Trp
```

|  |  |  |  |  |  |  |  |  |  |  |  |  |  |  |  |  |
|---|---|---|---|---|---|---|---|---|---|---|---|---|---|---|---|---|
|  |  |  | 115 |  |  |  | 120 |  |  |  |  | 125 |  |  |  |  |
| att | gtg | tta | caa | ttc | acc | ttc | ttc | aag | aat | gtg | gaa | atc | tcc | aat | ttt | 609 |
| Ile | Val | Leu | Gln | Phe | Thr | Phe | Phe | Lys | Asn | Val | Glu | Ile | Ser | Asn | Phe |  |
|  | 130 |  |  |  | 135 |  |  |  | 140 |  |  |  |  |  |  |  |
| gtc | tgt | gac | cca | tct | caa | ctt | ctc | aac | ctt | gcc | tgt | tct | gac | agt | gtc | 657 |
| Val | Cys | Asp | Pro | Ser | Gln | Leu | Leu | Asn | Leu | Ala | Cys | Ser | Asp | Ser | Val |  |
| 145 |  |  |  |  | 150 |  |  |  |  | 155 |  |  |  |  | 160 |  |
| atc | aat | agc | ata | ttc | ata | tat | tta | gat | agt | att | atg | ttt | ggt | ttt | ctt | 705 |
| Ile | Asn | Ser | Ile | Phe | Ile | Tyr | Leu | Asp | Ser | Ile | Met | Phe | Gly | Phe | Leu |  |
|  |  |  |  | 165 |  |  |  |  | 170 |  |  |  |  | 175 |  |  |
| ccc | att | tca | ggg | atc | ctt | ttg | tct | tac | gct | aac | aat | gtc | ccc | tcc | att | 753 |
| Pro | Ile | Ser | Gly | Ile | Leu | Leu | Ser | Tyr | Ala | Asn | Asn | Val | Pro | Ser | Ile |  |
|  |  |  | 180 |  |  |  |  | 185 |  |  |  |  | 190 |  |  |  |
| cta | aga | att | tca | tca | tca | gat | agg | aag | tct | aaa | gcc | ttc | tcc | acc | tgt | 801 |
| Leu | Arg | Ile | Ser | Ser | Ser | Asp | Arg | Lys | Ser | Lys | Ala | Phe | Ser | Thr | Cys |  |
|  | 195 |  |  |  |  | 200 |  |  |  |  | 205 |  |  |  |  |  |
| ggc | tct | cac | ctg | gca | gtt | gtt | tgc | tta | ttt | tat | gga | aca | ggc | att | ggc | 849 |
| Gly | Ser | His | Leu | Ala | Val | Val | Cys | Leu | Phe | Tyr | Gly | Thr | Gly | Ile | Gly |  |
| 210 |  |  |  |  | 215 |  |  |  |  | 220 |  |  |  |  |  |  |
| gtg | tac | ctg | act | tca | gct | gtg | tca | cca | ccc | ccc | agg | aat | ggt | gtg | gtg | 897 |
| Val | Tyr | Leu | Thr | Ser | Ala | Val | Ser | Pro | Pro | Pro | Arg | Asn | Gly | Val | Val |  |
| 225 |  |  |  |  | 230 |  |  |  |  | 235 |  |  |  |  | 240 |  |
| gca | tca | gtg | atg | tac | gct | gtg | gtc | acc | ccc | atg | ctg | aac | cct | ttc | atc | 945 |
| Ala | Ser | Val | Met | Tyr | Ala | Val | Val | Thr | Pro | Met | Leu | Asn | Pro | Phe | Ile |  |
|  |  |  |  | 245 |  |  |  |  | 250 |  |  |  |  | 255 |  |  |
| tac | agc | ctg | aga | aat | agg | gac | att | caa | agt | gcc | ctg | tgg | agg | ctg | cgc | 993 |
| Tyr | Ser | Leu | Arg | Asn | Arg | Asp | Ile | Gln | Ser | Ala | Leu | Trp | Arg | Leu | Arg |  |
|  |  |  | 260 |  |  |  |  | 265 |  |  |  |  | 270 |  |  |  |
| agc | aga | aca | gtc | gaa | tct | cat | gat | ctg | tta | tct | caa | gat | ctg | ctc | cat | 1041 |
| Ser | Arg | Thr | Val | Glu | Ser | His | Asp | Leu | Leu | Ser | Gln | Asp | Leu | Leu | His |  |
|  | 275 |  |  |  |  | 280 |  |  |  |  | 285 |  |  |  |  |  |
| cct | ttt | tct | tgt | gtg | ggt | gag | aaa | ggt | caa | cca | cat | taa |  |  |  | 1080 |
| Pro | Phe | Ser | Cys | Val | Gly | Glu | Lys | Gly | Gln | Pro | His | * |  |  |  |  |
| 290 |  |  |  |  | 295 |  |  |  |  | 300 |  |  |  |  |  |  |

```
<210> SEQ ID NO 10
<211> LENGTH: 1062
<212> TYPE: DNA
<213> ORGANISM: Homo sapiens
<220> FEATURE:
<221> NAME/KEY: CDS
<222> LOCATION: (1)..(1062)

<400> SEQUENCE: 10
```

|  |  |  |  |  |  |  |  |  |  |  |  |  |  |  |  |  |
|---|---|---|---|---|---|---|---|---|---|---|---|---|---|---|---|---|
| atg | gct | ttt | atc | gtg | ccc | gat | gtt | aat | gca | cgt | tct | ttt | ttg | aca | ata | 48 |
| Met | Ala | Phe | Ile | Val | Pro | Asp | Val | Asn | Ala | Arg | Ser | Phe | Leu | Thr | Ile |  |
| 1 |  |  |  | 5 |  |  |  |  | 10 |  |  |  |  | 15 |  |  |
| aat | tca | tgg | cca | tca | gat | aat | atc | aat | ttg | aca | tac | acg | gca | tca | ggg | 96 |
| Asn | Ser | Trp | Pro | Ser | Asp | Asn | Ile | Asn | Leu | Thr | Tyr | Thr | Ala | Ser | Gly |  |
|  |  |  | 20 |  |  |  |  | 25 |  |  |  |  | 30 |  |  |  |
| cct | tca | cag | cca | cca | tac | atc | agc | tac | atg | gaa | gca | gga | aac | caa | aca | 144 |
| Pro | Ser | Gln | Pro | Pro | Tyr | Ile | Ser | Tyr | Met | Glu | Ala | Gly | Asn | Gln | Thr |  |
|  |  | 35 |  |  |  |  | 40 |  |  |  |  | 45 |  |  |  |  |
| gga | ttt | tta | gag | ttt | atc | ctt | ctc | gga | ctc | tct | gag | gat | cca | gaa | cta | 192 |
| Gly | Phe | Leu | Glu | Phe | Ile | Leu | Leu | Gly | Leu | Ser | Glu | Asp | Pro | Glu | Leu |  |
|  | 50 |  |  |  |  | 55 |  |  |  |  | 60 |  |  |  |  |  |
| cag | ccg | ttc | ata | ttt | ggg | ctg | ttc | ctg | tcc | atg | tac | ctg | ggg | acg | gtg | 240 |
| Gln | Pro | Phe | Ile | Phe | Gly | Leu | Phe | Leu | Ser | Met | Tyr | Leu | Gly | Thr | Val |  |
| 65 |  |  |  |  | 70 |  |  |  |  | 75 |  |  |  |  | 80 |  |
| ctg | gga | aac | ctg | ctc | atc | atc | ctg | gcc | atc | agc | tct | gac | tcc | cac | ctc | 288 |
| Leu | Gly | Asn | Leu | Leu | Ile | Ile | Leu | Ala | Ile | Ser | Ser | Asp | Ser | His | Leu |  |

|  |  |  |  |  |  |  |  |  |  |  |  |  |  |  |  |
|---|---|---|---|---|---|---|---|---|---|---|---|---|---|---|---|
|  |  |  |  |  | 85 |  |  |  |  | 90 |  |  |  |  | 95 |

```
cac acc ccc atg tac ttc ttc ctc tcc aac ctg tcc tgg gtt gac atc      336
His Thr Pro Met Tyr Phe Phe Leu Ser Asn Leu Ser Trp Val Asp Ile
            100                 105                 110 tgt ttc agc act tgc atc gtc ccc aag atg ctg gtc aac atc cag acc      384
Cys Phe Ser Thr Cys Ile Val Pro Lys Met Leu Val Asn Ile Gln Thr
            115                 120                 125 gag aac aaa gcc atc tcc tac atg gac tgc ctc aca cag gtc tat ttc      432
Glu Asn Lys Ala Ile Ser Tyr Met Asp Cys Leu Thr Gln Val Tyr Phe
130                 135                 140 tcc atg ttt ttt cct att ctg gac acg cta ctc ctg acc gtg atg gcc      480
Ser Met Phe Phe Pro Ile Leu Asp Thr Leu Leu Leu Thr Val Met Ala
145                 150                 155                 160 tat gac cgg ttt gtg gct gtc tgc cac cct ctg cac tat atg atc atc      528
Tyr Asp Arg Phe Val Ala Val Cys His Pro Leu His Tyr Met Ile Ile
                165                 170                 175 atg aac ccc cac ctc tgt ggc ctc ctg gtt ttt gtc acc tgg ctc att      576
Met Asn Pro His Leu Cys Gly Leu Leu Val Phe Val Thr Trp Leu Ile
            180                 185                 190 ggt gtc atg aca tcc ctc ctc cat att tct ctg atg atg cat cta atc      624
Gly Val Met Thr Ser Leu Leu His Ile Ser Leu Met Met His Leu Ile
            195                 200                 205 ttc tgt aaa gat ttt gaa att cca cat ttt ttc tgc gaa ctg acg tac      672
Phe Cys Lys Asp Phe Glu Ile Pro His Phe Phe Cys Glu Leu Thr Tyr
210                 215                 220 atc ctc cag ctg gcc tgc tct gat acc ttc ctg aac agc acg ttg ata      720
Ile Leu Gln Leu Ala Cys Ser Asp Thr Phe Leu Asn Ser Thr Leu Ile
225                 230                 235                 240 tac ttt atg acg ggt gtg ctg ggc gtt ttt ccc ctc ctt ggg atc att      768
Tyr Phe Met Thr Gly Val Leu Gly Val Phe Pro Leu Leu Gly Ile Ile
                245                 250                 255 ttc tct tat tca cga att gct tca tcc ata agg aag atg tcc tca tct      816
Phe Ser Tyr Ser Arg Ile Ala Ser Ser Ile Arg Lys Met Ser Ser Ser
            260                 265                 270 ggg gga aaa caa aaa gca ctt tcc acc tgt ggg tct cac ctc tcc gtc      864
Gly Gly Lys Gln Lys Ala Leu Ser Thr Cys Gly Ser His Leu Ser Val
            275                 280                 285 gtt tct tta ttt tat ggg aca ggc att ggg gtc cac ttc act tct gcg      912
Val Ser Leu Phe Tyr Gly Thr Gly Ile Gly Val His Phe Thr Ser Ala
            290                 295                 300 gtg act cac tct tcc cag aaa atc tcc gtg gcc tcg gtg atg tac act      960
Val Thr His Ser Ser Gln Lys Ile Ser Val Ala Ser Val Met Tyr Thr
305                 310                 315                 320 gtg gtc acc ccc atg ttg aac ccc ttc atc tac agc ctg agg aac aag     1008
Val Val Thr Pro Met Leu Asn Pro Phe Ile Tyr Ser Leu Arg Asn Lys
                325                 330                 335 gat gtg aag gga gcc ctg ggg agt ctc ctc agc agg gca gcc tct tgt     1056
Asp Val Lys Gly Ala Leu Gly Ser Leu Leu Ser Arg Ala Ala Ser Cys
            340                 345                 350 ttg tga                                                             1062
Leu *

<210> SEQ ID NO 11
<211> LENGTH: 1297
<212> TYPE: DNA
<213> ORGANISM: Homo sapiens
<220> FEATURE:
<221> NAME/KEY: CDS
<222> LOCATION: (225)..(1091)

<400> SEQUENCE: 11
```

-continued

```
gaactcggca cgaggcggcc caggagaagc agttcctgcc ggcgctgctg agtttcttca        60
tctacaaccc gcgcttctgg ccgcgggaag gagaggttgt tcggaatcct ataattgaaa       120
aacagtaaag atggaaaacc agttattgaa tatcaagagg aggagttgtt gaagtctcag       180
gggatccaga actgcagcca gtccttgctg ggctgttcct gtcc atg tgc ctg gtc       236
                                                 Met Cys Leu Val
                                                   1 acg gtg ctg ggg aac ctg ctc atc atc ctg gcc atc agc cct gac tcc        284
Thr Val Leu Gly Asn Leu Leu Ile Ile Leu Ala Ile Ser Pro Asp Ser
  5              10                  15                  20 cac ctc cac acc ccc atg tac ttc ttc ctc tcc aac ctg tcc ttg gct        332
His Leu His Thr Pro Met Tyr Phe Phe Leu Ser Asn Leu Ser Leu Ala
                 25                  30                  35 gac atc ggt ttc acc tcc acc acg gtc ccc aag atg att gtg gac atg        380
Asp Ile Gly Phe Thr Ser Thr Thr Val Pro Lys Met Ile Val Asp Met
             40                  45                  50 caa act cac agc aga gtc atc tcc tat gaa ggc tgc ctg act cag atg        428
Gln Thr His Ser Arg Val Ile Ser Tyr Glu Gly Cys Leu Thr Gln Met
         55                  60                  65 tct ttt ttt gtc ctt ttt gca tgt atg gat gac atg ctc ctg agt gtg        476
Ser Phe Phe Val Leu Phe Ala Cys Met Asp Asp Met Leu Leu Ser Val
     70                  75                  80 atg gcc tat gac cgg ttt gtg gcc atc tgt cac ccc ctg cac tac cga        524
Met Ala Tyr Asp Arg Phe Val Ala Ile Cys His Pro Leu His Tyr Arg
 85                  90                  95                 100 atc atc atg aac cca cgc ctc tgt ggc ttc tta atc ttg ttg tct ttt        572
Ile Ile Met Asn Pro Arg Leu Cys Gly Phe Leu Ile Leu Leu Ser Phe
                105                 110                 115 ttt att agt ctt ttg gac tcc cag ttg cac aat ttg att atg tta cag        620
Phe Ile Ser Leu Leu Asp Ser Gln Leu His Asn Leu Ile Met Leu Gln
            120                 125                 130 ctc acc tgc ttc aag gat gtg gac att tct aat ttc ttc tgt gac cct        668
Leu Thr Cys Phe Lys Asp Val Asp Ile Ser Asn Phe Phe Cys Asp Pro
        135                 140                 145 tct caa ctc ctc cac ctt agg tgt tcc gac acc ttc atc aat gaa atg        716
Ser Gln Leu Leu His Leu Arg Cys Ser Asp Thr Phe Ile Asn Glu Met
    150                 155                 160 gtc ata tat ttc atg ggt gcc ata ttt ggc tgt ctc cct atc tca ggg        764
Val Ile Tyr Phe Met Gly Ala Ile Phe Gly Cys Leu Pro Ile Ser Gly
165                 170                 175                 180 atc ctt ttc tct tac tat aaa att gtt tcc ccc att ctg aga gtt cca        812
Ile Leu Phe Ser Tyr Tyr Lys Ile Val Ser Pro Ile Leu Arg Val Pro
                185                 190                 195 aca tca gat ggg aag tat aaa gcc ttc tcc acc tgt ggc tct cac ctg        860
Thr Ser Asp Gly Lys Tyr Lys Ala Phe Ser Thr Cys Gly Ser His Leu
            200                 205                 210 gca gtt gtt tgc tta ttt tat gga aca ggg ctt gta ggg tac ctc agt        908
Ala Val Val Cys Leu Phe Tyr Gly Thr Gly Leu Val Gly Tyr Leu Ser
        215                 220                 225 tca gct gtg tta cca tcc ccc agg aag agt atg gtg gct tca gtg atg        956
Ser Ala Val Leu Pro Ser Pro Arg Lys Ser Met Val Ala Ser Val Met
    230                 235                 240 tac act gtg gtc acc ccc atg ctg aac ccc ttc atc tac agc ctg agg       1004
Tyr Thr Val Val Thr Pro Met Leu Asn Pro Phe Ile Tyr Ser Leu Arg
245                 250                 255                 260 aac aag gac att caa agt gcc ctg tgc agg ctg cat ggc aga atc atc       1052
Asn Lys Asp Ile Gln Ser Ala Leu Cys Arg Leu His Gly Arg Ile Ile
                265                 270                 275
```

-continued

```
aaa tct cat cat ctc cat cct ttt tgt tat atg gga tag aaatggcagc      1101
Lys Ser His His Leu His Pro Phe Cys Tyr Met Gly *
            280                 285 aaaatttaac acctaggcct gcaaattctg cctccttggt cacattattt tggttgcttg   1161
atggctttca ttcctctctg ggtttcgtat gtgaatattg cttgctttgt tttgtcttta   1221
attgcaatgg gtgagtattc tggtatcctt tgttcatcat acacatcatg aatgattcca   1281
atataaaaaa aaaaaa                                                   1297

<210> SEQ ID NO 12
<211> LENGTH: 1535
<212> TYPE: DNA
<213> ORGANISM: Homo sapiens
<220> FEATURE:
<221> NAME/KEY: CDS
<222> LOCATION: (1)..(1338)

<400> SEQUENCE: 12 atg aac cgc acc ggg gca tgt cga ctt caa ggg gct ggt ggg ccg tcc     48
Met Asn Arg Thr Gly Ala Cys Arg Leu Gln Gly Ala Gly Gly Pro Ser
 1               5                  10                  15 ctg tcc ttg gag act cct ctc tgc ctc aat tgc tct gtc ctc cct gga    96
Leu Ser Leu Glu Thr Pro Leu Cys Leu Asn Cys Ser Val Leu Pro Gly
                20                  25                  30 gac ctg tac cca ggg ggt gca agg aac ccc atg gct tgc aat ggc agt   144
Asp Leu Tyr Pro Gly Gly Ala Arg Asn Pro Met Ala Cys Asn Gly Ser
            35                  40                  45 gcg gcc agg ggg cac ttt gac cct gag gac ttg aac ctg act gac gag   192
Ala Ala Arg Gly His Phe Asp Pro Glu Asp Leu Asn Leu Thr Asp Glu
        50                  55                  60 gca ctg aga ctc aag tac ctg ggg ccc cag cag aca gag ctg ttc atg   240
Ala Leu Arg Leu Lys Tyr Leu Gly Pro Gln Gln Thr Glu Leu Phe Met
 65                  70                  75                  80 ccc atc tgt gcc aca tac ctg ctg atc ttc gtg gtg ggc gct gtg ggc   288
Pro Ile Cys Ala Thr Tyr Leu Leu Ile Phe Val Val Gly Ala Val Gly
                85                  90                  95 aat ggg ctg acc tgt ctg gtc atc ctg cgc cac aag gcc atg cgc acg   336
Asn Gly Leu Thr Cys Leu Val Ile Leu Arg His Lys Ala Met Arg Thr
            100                 105                 110 cct acc aac tac tac ctc ttc agc ctg gcc gtg tcg gac ctg ctg gtg   384
Pro Thr Asn Tyr Tyr Leu Phe Ser Leu Ala Val Ser Asp Leu Leu Val
        115                 120                 125 ctg ctg gtg ggc ctg ccc ctg gag ctc tat gag atg tgg cac aac tac   432
Leu Leu Val Gly Leu Pro Leu Glu Leu Tyr Glu Met Trp His Asn Tyr
130                 135                 140 ccc ttc ctg ctg ggc gtt ggt ggc tgc tat ttc cgc acg cta ctg ttt   480
Pro Phe Leu Leu Gly Val Gly Gly Cys Tyr Phe Arg Thr Leu Leu Phe
145                 150                 155                 160 gag atg gtc tgc ctg gcc tca gtg ctc aac gtc act gcc ctg agc gtg   528
Glu Met Val Cys Leu Ala Ser Val Leu Asn Val Thr Ala Leu Ser Val
                165                 170                 175 gaa cgc tat gtg gcc gtg gtg cac cca ctc cag gcc agg tcc atg gtg   576
Glu Arg Tyr Val Ala Val Val His Pro Leu Gln Ala Arg Ser Met Val
            180                 185                 190 acg cgg gcc cat gtg cgc cga gtg ctt ggg gcc gtc tgg ggt ctt gcc   624
Thr Arg Ala His Val Arg Arg Val Leu Gly Ala Val Trp Gly Leu Ala
        195                 200                 205 atg ctc tgc tcc ctg ccc aac acc agc ctg cac ggc atc cgg cag ctg   672
Met Leu Cys Ser Leu Pro Asn Thr Ser Leu His Gly Ile Arg Gln Leu
            210                 215                 220
```

```
cac gtg ccc tgc cgg ggc cca gtg cca gac tca gct gtt tgc atg ctg      720
His Val Pro Cys Arg Gly Pro Val Pro Asp Ser Ala Val Cys Met Leu
225                 230                 235                 240 gtc ccg cca cgg gcc ctc tac aac atg gta gtg cag acc acc gcg ctg      768
Val Pro Pro Arg Ala Leu Tyr Asn Met Val Val Gln Thr Thr Ala Leu
            245                 250                 255 ctc ttc ttc tgc ctg ccc atg gcc atc atg agc gtg ctc tac ctg ctc      816
Leu Phe Phe Cys Leu Pro Met Ala Ile Met Ser Val Leu Tyr Leu Leu
                260                 265                 270 att ggg ctg cga ctg cgg cgg gag agg ctg ctc atg cag gag gcc          864
Ile Gly Leu Arg Leu Arg Arg Glu Arg Leu Leu Leu Met Gln Glu Ala
            275                 280                 285 aag ggc agg ggc tct gca gca gcc agg tcc aga tac acc tgc agg ctc      912
Lys Gly Arg Gly Ser Ala Ala Ala Arg Ser Arg Tyr Thr Cys Arg Leu
290                 295                 300 cag cag cac gat cgg ggc cgg aga caa gtg acc aag atg ctg ttt gtc      960
Gln Gln His Asp Arg Gly Arg Arg Gln Val Thr Lys Met Leu Phe Val
305                 310                 315                 320 ctg gtc gtg gtg ttt ggc atc tgc tgg gcc ccg ttc cac gcc gac cgc     1008
Leu Val Val Val Phe Gly Ile Cys Trp Ala Pro Phe His Ala Asp Arg
                325                 330                 335 gtc atg tgg agc gtc gtg tca cag tgg aca gat ggc ctg cac ctg gcc     1056
Val Met Trp Ser Val Val Ser Gln Trp Thr Asp Gly Leu His Leu Ala
            340                 345                 350 ttc cag cac gtg cac gtc atc tcc ggc atc ttc ttc tac ctg ggc tcg     1104
Phe Gln His Val His Val Ile Ser Gly Ile Phe Phe Tyr Leu Gly Ser
        355                 360                 365 gcg gcc aac ccc gtg ctc tat agc ctc atg tcc agc cgc ttc cga gag     1152
Ala Ala Asn Pro Val Leu Tyr Ser Leu Met Ser Ser Arg Phe Arg Glu
370                 375                 380 acc ttc cag gag gcc ctg tgc ctc ggg gcc tgc tgc cat cgc ctc aga     1200
Thr Phe Gln Glu Ala Leu Cys Leu Gly Ala Cys Cys His Arg Leu Arg
385                 390                 395                 400 ccc cgc cac agc tcc cac agc ctc agc agg atg acc aca ggc agc acc     1248
Pro Arg His Ser Ser His Ser Leu Ser Arg Met Thr Thr Gly Ser Thr
                405                 410                 415 ctg tgt gat gtg ggc tcc ctg ggc agc tgg gtc cac ccc ctg gct ggg     1296
Leu Cys Asp Val Gly Ser Leu Gly Ser Trp Val His Pro Leu Ala Gly
            420                 425                 430 aac gat ggc cca gag gcg cag caa gag acc gat cca tcc tga gtggagc     1345
Asn Asp Gly Pro Glu Ala Gln Gln Glu Thr Asp Pro Ser *
        435                 440                 445 cttaaagtgg cttcacctgg aggggccaga gggtcacctg gagctgggga gacacatctg  1405
ccttcctctg cagggatgcc ttcacgtact gtccctagtt cagcctagaa attctgacca  1465
gcacctcagt ttccctcaga gggaaacagc aggaggaggg atccctgact gctgaggact  1525
cacactgacc                                                         1535

<210> SEQ ID NO 13
<211> LENGTH: 1539
<212> TYPE: DNA
<213> ORGANISM: Homo sapiens
<220> FEATURE:
<221> NAME/KEY: CDS
<222> LOCATION: (130)..(1539)

<400> SEQUENCE: 13
gcacgaggtg gaggacgcgg ctgcttcaag tccttggctc tgatccaggc cacagattcc    60
aggattctac aggcaggaaa catcttagaa atcagggttg ggcaggcagg agccaggaga   120
```

-continued

```
gtagctaca   atg act tca cca gta ctg gtg gac ata cga gaa gag gtg        168
            Met Thr Ser Pro Val Leu Val Asp Ile Arg Glu Glu Val
              1               5                  10 acc tgc cct atc tgc ctg gag ctc cta aca gaa ccc ctg agc ata gac        216
Thr Cys Pro Ile Cys Leu Glu Leu Leu Thr Glu Pro Leu Ser Ile Asp
         15                  20                  25 tgt ggc cac agc ttc tgc caa gcc tgc atc aca cca aat ggc agg gaa        264
Cys Gly His Ser Phe Cys Gln Ala Cys Ile Thr Pro Asn Gly Arg Glu
 30                  35                  40                  45 tca gtg att ggt caa gaa ggg gaa aga agc tgc cct gtg tgc cag acc        312
Ser Val Ile Gly Gln Glu Gly Glu Arg Ser Cys Pro Val Cys Gln Thr
                 50                  55                  60 agc tac cag cca ggg aac ctg cgg cct aat cgg cat ctg gcc aac ata        360
Ser Tyr Gln Pro Gly Asn Leu Arg Pro Asn Arg His Leu Ala Asn Ile
             65                  70                  75 gtg agg cgg ctc aga gag gta gtg ttg ggc cct ggg aag cag ctg aaa        408
Val Arg Arg Leu Arg Glu Val Val Leu Gly Pro Gly Lys Gln Leu Lys
         80                  85                  90 gca gtt ctt tgt gca gac cat gga gaa aaa ctg cag ctc ttc tgt cag        456
Ala Val Leu Cys Ala Asp His Gly Glu Lys Leu Gln Leu Phe Cys Gln
 95                 100                 105 gag gat ggg aag gag aag ttt cag gag tct cta aag aag ctg aag aac        504
Glu Asp Gly Lys Glu Lys Phe Gln Glu Ser Leu Lys Lys Leu Lys Asn
110                 115                 120                 125 gag gag cag gaa gct gag aag cta aca gct ttt atc aga gag aag aag        552
Glu Glu Gln Glu Ala Glu Lys Leu Thr Ala Phe Ile Arg Glu Lys Lys
                130                 135                 140 aca tcc tgg aag gca agg gag act ttt tct gaa gat gtc ctg ggg cag        600
Thr Ser Trp Lys Ala Arg Glu Thr Phe Ser Glu Asp Val Leu Gly Gln
            145                 150                 155 gaa tca tgg cag agt aca aat gca agg gaa aat gca ggg atc cca ggg        648
Glu Ser Trp Gln Ser Thr Asn Ala Arg Glu Asn Ala Gly Ile Pro Gly
        160                 165                 170 ctg gag gct gcc cac ttc tgg att gcc atc cct ttc tgt gcc atg tat        696
Leu Glu Ala Ala His Phe Trp Ile Ala Ile Pro Phe Cys Ala Met Tyr
175                 180                 185 ctt gta gca ctg gtt gga aat gct gcc ctc atc ctg gtc att gcc atg        744
Leu Val Ala Leu Val Gly Asn Ala Ala Leu Ile Leu Val Ile Ala Met
190                 195                 200                 205 gac aat gct ctt cat gca cct atg tac ctc ttc ctc tgc ctt ctc tca        792
Asp Asn Ala Leu His Ala Pro Met Tyr Leu Phe Leu Cys Leu Leu Ser
                210                 215                 220 ctc aca gac ctg gct ctc agt tct acc act gtg ccc aag atg ctg gcc        840
Leu Thr Asp Leu Ala Leu Ser Ser Thr Thr Val Pro Lys Met Leu Ala
            225                 230                 235 att ttg tgg ctc cat gct ggt gag att tcc ttt ggt gga tgc ctg gcc        888
Ile Leu Trp Leu His Ala Gly Glu Ile Ser Phe Gly Gly Cys Leu Ala
        240                 245                 250 cag atg ttt tgt gtc cat tct atc tat gct ctg gag tcc tcg att cta        936
Gln Met Phe Cys Val His Ser Ile Tyr Ala Leu Glu Ser Ser Ile Leu
255                 260                 265 ctt gcc atg gcc ttt gat agg tat gtg gct atc tgt aac cca tta agg        984
Leu Ala Met Ala Phe Asp Arg Tyr Val Ala Ile Cys Asn Pro Leu Arg
270                 275                 280                 285 tat aca acc att ctc aac cat gct gtc ata ggc aga att ggc ttt gtt       1032
Tyr Thr Thr Ile Leu Asn His Ala Val Ile Gly Arg Ile Gly Phe Val
                290                 295                 300 ggg cta ttc cgt agt gtg gct att gtc tcc ccc ttc atc ttc ttg ctg       1080
Gly Leu Phe Arg Ser Val Ala Ile Val Ser Pro Phe Ile Phe Leu Leu
            305                 310                 315
```

```
agg cga ctc ccc tac tgt ggt cac cgt gtc atg aca cac aca tac tgt      1128
Arg Arg Leu Pro Tyr Cys Gly His Arg Val Met Thr His Thr Tyr Cys
        320                 325                 330 gag cat atg ggc atc gcc cga ctg gcc tgt gcc aac atc act gtc aat      1176
Glu His Met Gly Ile Ala Arg Leu Ala Cys Ala Asn Ile Thr Val Asn
    335                 340                 345 att gtc tat ggg cta act gtg gct ctg ctg gcc atg gga ctg gat tcc      1224
Ile Val Tyr Gly Leu Thr Val Ala Leu Leu Ala Met Gly Leu Asp Ser
350                 355                 360                 365 att ctc att gcc att tcc tat ggc ttt atc ctc cat gca gtc ttt cac      1272
Ile Leu Ile Ala Ile Ser Tyr Gly Phe Ile Leu His Ala Val Phe His
            370                 375                 380 ctt cca tct cat gat gcc cag cac aaa gct ctg agt acc tgt ggc tcc      1320
Leu Pro Ser His Asp Ala Gln His Lys Ala Leu Ser Thr Cys Gly Ser
        385                 390                 395 cac att ggc atc atc ctg gtt ttc tac atc cct gcc ttc ttc tcc ttc      1368
His Ile Gly Ile Ile Leu Val Phe Tyr Ile Pro Ala Phe Phe Ser Phe
            400                 405                 410 ctc acc cac cgc ttt ggt cac cac gaa gtc ccc aag cat gtg cac atc      1416
Leu Thr His Arg Phe Gly His His Glu Val Pro Lys His Val His Ile
    415                 420                 425 ttt ctg gct aat ctc tat gtg ctg gtg cct cct gta ctc aat cct att      1464
Phe Leu Ala Asn Leu Tyr Val Leu Val Pro Pro Val Leu Asn Pro Ile
430                 435                 440                 445 ctc tat gga gct aga acc aag gag att cgg agt cga ctt cta aaa ctg      1512
Leu Tyr Gly Ala Arg Thr Lys Glu Ile Arg Ser Arg Leu Leu Lys Leu
            450                 455                 460 ctt cac ctg ggg aag act tca ata tga                                  1539
Leu His Leu Gly Lys Thr Ser Ile *
        465                 470
```